US007141592B2

(12) United States Patent
Gopalsamy et al.

(10) Patent No.: US 7,141,592 B2
(45) Date of Patent: Nov. 28, 2006

(54) SUBSTITUTED OXADIAZOLIDINEDIONES

(75) Inventors: Ariamala Gopalsamy, Mahwah, NJ (US); Scott Lee Kincaid, Middletown, NY (US)

(73) Assignee: Wyeth, Madison, NJ (US)

( * ) Notice: Subject to any disclaimer, the term of this patent is extended or adjusted under 35 U.S.C. 154(b) by 64 days.

(21) Appl. No.: 10/947,810

(22) Filed: Sep. 23, 2004

(65) Prior Publication Data

US 2005/0113428 A1     May 26, 2005

Related U.S. Application Data

(60) Provisional application No. 60/505,782, filed on Sep. 25, 2003.

(51) Int. Cl.
    A61K 31/4245     (2006.01)
    C07D 271/07     (2006.01)

(52) U.S. Cl. ............................. 514/364; 548/132
(58) Field of Classification Search ................ 514/364; 548/132
See application file for complete search history.

(56) References Cited

U.S. PATENT DOCUMENTS

| | | | |
|---|---|---|---|
| 3,026,325 A | 3/1962 | Heinzelman et al. ....... 548/496 |
| 3,476,770 A | 11/1969 | Scherrer ..................... 548/494 |
| 3,557,142 A | 1/1971 | Bell .......................... 548/516 |
| 3,843,683 A | 10/1974 | Bell .......................... 548/493 |
| 4,478,819 A | 10/1984 | Hercelin et al. ............ 424/457 |
| 4,736,043 A | 4/1988 | Michel et al. ............... 548/492 |
| 4,851,406 A | 7/1989 | Martens et al. ......... 514/217.04 |
| 5,164,372 A | 11/1992 | Matsuo et al. ................ 514/19 |
| 5,420,146 A | 5/1995 | Malamas et al. ........... 514/364 |
| 5,420,289 A | 5/1995 | Musser et al. .............. 548/159 |
| 5,468,762 A | 11/1995 | Malamas et al. ........... 514/376 |
| 5,480,896 A | 1/1996 | Malamas et al. ........... 514/364 |
| 5,482,960 A | 1/1996 | Berryman .................... 514/414 |
| 5,502,187 A | 3/1996 | Ayer et al. .................. 544/117 |
| 5,532,256 A | 7/1996 | Malamas et al. ........... 514/361 |
| 5,541,343 A | 7/1996 | Himmelsbach et al. ..... 514/424 |
| 5,612,360 A | 3/1997 | Boyd et al. ................. 514/381 |
| 5,859,044 A | 1/1999 | Dow et al. .................. 514/419 |
| 6,048,875 A | 4/2000 | De Nanteuil et al. ....... 514/314 |
| 6,110,963 A | 8/2000 | Malamas ..................... 514/443 |
| 6,166,069 A | 12/2000 | Malamas et al. ........... 514/469 |
| 6,232,322 B1 | 5/2001 | Malamas et al. ........... 514/303 |
| 6,251,936 B1 | 6/2001 | Wrobel et al. .............. 514/443 |
| 6,302,837 B1 | 10/2001 | De Nanteuil et al. ....... 514/337 |
| 6,479,524 B1 | 11/2002 | Priepke et al. .............. 514/352 |
| 6,599,929 B1 | 7/2003 | Cho et al. ................... 514/415 |
| 6,787,556 B1 | 9/2004 | Hargreaves et al. ........ 514/311 |
| 6,800,645 B1 | 10/2004 | Cox et al. ................... 514/314 |
| 6,800,654 B1 | 10/2004 | Mayer et al. ............... 514/381 |
| 6,844,358 B1 | 1/2005 | Malamas et al. ........... 514/336 |
| 2003/0013732 A1 | 1/2003 | Elokdah ..................... 514/301 |
| 2003/0018067 A1 | 1/2003 | Elokdah et al. ............. 514/469 |
| 2003/0060497 A1 | 3/2003 | Gerlach et al. ............. 514/414 |
| 2003/0125371 A1 | 7/2003 | Elokdah et al. ............. 514/419 |
| 2004/0116488 A1 | 6/2004 | Jennings et al. ............ 514/374 |
| 2004/0116504 A1 | 6/2004 | Elokdah et al. ............. 514/419 |
| 2004/0122070 A1 | 6/2004 | Jennings ..................... 514/374 |
| 2004/0138283 A1 | 7/2004 | Jennings et al. ............ 514/414 |
| 2004/0204417 A1 | 10/2004 | Perez et al. ................. 514/249 |
| 2005/0070584 A1 | 3/2005 | Havran et al. .............. 514/357 |
| 2005/0070585 A1 | 3/2005 | Elokdah et al. ............. 514/364 |
| 2005/0070587 A1 | 3/2005 | Elokdah et al. ............. 514/381 |
| 2005/0070592 A1 | 3/2005 | Gundersen .................. 514/415 |
| 2005/0096377 A1 | 5/2005 | Hu ............................. 514/419 |
| 2005/0113428 A1 | 5/2005 | Gopalsamy et al. ........ 514/364 |
| 2005/0113436 A1 | 5/2005 | Elokdah et al. ............. 514/411 |
| 2005/0113438 A1 | 5/2005 | Hu et al. ..................... 514/414 |
| 2005/0113439 A1 | 5/2005 | Hu ............................. 514/414 |
| 2005/0119296 A1 | 6/2005 | Elokdah et al. ............. 514/300 |
| 2005/0119326 A1 | 6/2005 | Havran et al. .............. 514/414 |
| 2005/0119327 A1 | 6/2005 | Hu ............................. 514/414 |
| 2005/0215626 A1 | 9/2005 | Havran et al. .............. 514/469 |
| 2006/0020003 A1 | 1/2006 | Commons et al. .......... 514/374 |
| 2006/0052348 A1 | 3/2006 | Commons et al. ............ 514/92 |
| 2006/0052349 A1 | 3/2006 | Commons et al. ............ 514/95 |
| 2006/0052420 A1 | 3/2006 | Commons ................... 514/340 |

FOREIGN PATENT DOCUMENTS

| | | |
|---|---|---|
| DE | 3147276 A1 | 6/1983 |
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |

(Continued)

OTHER PUBLICATIONS

Gopalsamy, A. et al., "Design and synthesis of oxadizolidinediones as inhibitors of plasminogen activator inhibitor-1," *Bioorganic & Medicinal Chemistry Letters*, 2004, 14:3477-3480.

(Continued)

*Primary Examiner*—Kamal A. Saeed
*Assistant Examiner*—Michael Barker
(74) *Attorney, Agent, or Firm*—Woodcock Washburn LLP

(57) ABSTRACT

The present invention relates generally to substituted oxadiazolidinediones and methods of using them.

42 Claims, No Drawings

FOREIGN PATENT DOCUMENTS

| | | | |
|---|---|---|---|
| EP | 0 955 299 A1 | 11/1999 | |
| EP | 1 156 045 A1 | 11/2001 | |
| FR | 2 244 499 A1 | 4/1975 | |
| FR | 2 777 886 A1 | 10/1999 | |
| FR | 2 799 756 A1 | 4/2001 | |
| GB | 1 321 433 | 6/1973 | |
| WO | 94/13637 A1 | 6/1994 | |
| WO | 94/14434 A1 | 7/1994 | |
| WO | 94/26738 A1 | 11/1994 | |
| WO | WO 9425448 A1 | 11/1994 | * |
| WO | 95/10513 A1 | 4/1995 | |
| WO | 96/06840 A1 | 3/1996 | |
| WO | 96/21656 A1 | 7/1996 | |
| WO | 96/26207 A1 | 8/1996 | |
| WO | 96/32379 A1 | 10/1996 | |
| WO | 97/09308 A1 | 3/1997 | |
| WO | 97/43260 A1 | 11/1997 | |
| WO | 97/48697 A1 | 12/1997 | |
| WO | 98/08818 A1 | 3/1998 | |
| WO | 99/28297 A1 | 6/1999 | |
| WO | 99/43651 A2 | 9/1999 | |
| WO | 99/43654 A2 | 9/1999 | |
| WO | 99/43672 A1 | 9/1999 | |
| WO | 99/46260 A1 | 9/1999 | |
| WO | 99/50268 A1 | 10/1999 | |
| WO | 99/58519 A1 | 11/1999 | |
| WO | 99/61435 A1 | 12/1999 | |
| WO | 00/32180 A2 | 6/2000 | |
| WO | 00/35919 A1 | 6/2000 | |
| WO | 00/46195 A1 | 8/2000 | |
| WO | 00/46197 A1 | 8/2000 | |
| WO | 00/64876 A1 | 11/2000 | |
| WO | 00/64888 A1 | 11/2000 | |
| WO | 01/12187 A2 | 2/2001 | |
| WO | 02/030895 A1 | 4/2002 | |
| WO | 02/072549 A1 | 9/2002 | |
| WO | 03/000253 A1 | 1/2003 | |
| WO | 03/031409 A1 | 4/2003 | |
| WO | 03/068742 A1 | 8/2003 | |
| WO | 03/087087 A2 | 10/2003 | |
| WO | 2004/052854 A2 | 6/2004 | |

OTHER PUBLICATIONS

U.S. Appl. No. 10/947,856, filed Sep. 23, 2004, Elokdah et al.

Krishnamurti, C. et al., "Plasminogen Activator Inhibitor: A Regulator of Ancrod-Induced Fibrin Deposition in Rabbits," *Blood*, 69(3): 798-803 (Mar. 1987).

Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).

Carmeliet, P. et al., "Plasminogen Activator Inhibitor-1 Gene-deficient Mice," *Journal of Clinical Investigation*, 92: 2756-2760 (Dec. 1993).

Rocha, E. et al., "The Relationship Between Impaired Fibrinolysis and Coronary Heart Disease," *Fibrinolysis*, 8: 294-303 (1994).

Aznar, J. et al., "Role of Plasminogen Activator Inhibitor Type 1 in the Pathogenesis of Coronary Artery Diseases," *Haemostasis* 24: 243-251 (1994).

Biemond, B. J. et al., "Thrombolysis and Reocclusion in Experimental Jugular Vein and Coronary Artery Thrombosis," *Circulation*, 91: 1175-1181 (1995).

Levi, M. et al., "Inhibition of Plasminogen Activator Inhibitor-1 Activity Results in Promotion of Endogenous Thrombolysis and Inhibition of Thrombus Experimental Thrombosis," *Circulation* 85:305-312 (1992).

Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).

Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).

Schneiderman J. et. al., "Increased type 1 plasminogen activator inhibitor gene expression in atherosclerotic human arteries," *Proc Natl Acad Sci* 89: 6998-7002 (Aug. 1992).

Juhan-Vague, I. et. al., "Deficient t-PA Release and Elevated PA Inhibitor Levels in Patients with Spontaneous or Recurrent Deep Venous Thrombosis," *Thromb Haemost* 57: 67-72 (1987).

Juhan-Vague, I. et. al., "PAI-1, Obesity, Insulin Resistance and Risk of Cardiovascular Events," *Thromb Haemost* 78: 565-660 (1997).

Hamsten, A. et. al., "Plasminogen Activator Inhibitor in Plasma: Risk Factor For Recurrent Myocardial Infarction," *Lancet* 2: 3-9 (Jul. 4, 1987).

Siemens, H. J. et. al., "Course of Molecular Hemostatic Markers During and After Different Surgical Procedures," *J Clin Anesthesia* 11: 622-629 (Dec. 1999).

Koh, K. et. al., "Effects of Hormone-Replacement Therapy on Fibrinolysis in Postmenopausal Women," *N Engl J Med* 336(10): 683-690 (Mar. 6, 1997).

Malamas, M. S. et al., "New Azolidinediones as Inhibitors of Protein Tyrosine Phosphatase 1B with Antihyperglycemic Properties," *J. Med. Chem.*, 2000, 43:995-1010.

Malamas, M. S. et al., "Antihyperglycemic activity of new 1,2,4-oxadiazolidine-3,5-diones," *Eur. J. Med. Chem.*, 2001, 36:31-42.

U.S. Appl. No. 10/947,711, filed Sep. 23, 2004, Gopalsamy et al.

Aggarwal et al., "A catalytic antibody programmed for torsional activation of amide bond hydrolysis, " *Chem. Eur. J.*, Jan. 25, 2003, 9(13), 3132-3142.

Ballantine, J.A., "The Chemistry of Bacteria," *Journal of the Chemical Society Abstracts*, 1957, 2222-2227.

Charlton, Peter, "The status of plasminogen activator inhibitor-1 as a therapeutic target," *Expert Opinion On Investigational Drugs*, May 1997, 6(5), 539-554.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2, 1422-1428.

Da Settimo, A. et al., "Reaction of indole derivatives with bromine, substitution, oxidation, and dimerization, " *J Org Chem*, 1970, 35(8):2546-2551.

Delgado et al., *Journal of Organic Chemistry* (1993), 58(10), pp. 2862-2866.

Dillard R. D. et al., "Indole Inhibitors of Human Nonpancreatic Secretory Phospholipase $A_2$ 1. Indole-3-Acetamides", *Journal of Medicinal Chemistry*, American Chemical Society, 39(26), 5119-5136, 1996.

Guzzo, P.R. et al., "Synthesis of a conformationally constrained threonin-valine dipeptide mimetic: design of a potential inhibitor of plasminogen activator inhibitor-1," *Tetrahedron Letters*, 2002 43(1), 41-43.

Hipskind, P. A. et al., "Potent and selective 1,2,3-trisubstituted indole NPY Y-1 antagonists, " *J Med Chem*, 1997, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 31-42.

Malamas, M.S. et al. "Novel benzofuran and benzothiophene biphenyls as inhibitors of protein tyrosine phosphatase 1 B with antihyperglycemic properties," *Journal of Medicinal Chemistry*, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," *Zhurnal Organicheskoi Khimii*, 1986, 22(9), 1868-1873.

\* cited by examiner

SUBSTITUTED OXADIAZOLIDINEDIONES

CROSS-REFERENCE TO RELATED APPLICATIONS

This application claims the benefit of U.S. Provisional Application No. 60/505,782 filed Sep. 25, 2003, the entire disclosure of which is incorporated herein by reference.

BACKGROUND

The present invention relates generally to substituted oxadiazolidinediones and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main responsibilities in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood*, 69, 798 (1987); Reilly, Arteriosclerosis and Thrombosis, 11, 1276 (1991); Carmeliet, *Journal of Clinical Investigation*, 92, 2756 (1993), Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism*, 85, 4, 1563 (2000)), bone loss induced by estrogen deficiency (Daci, *Journal of Bone and Mineral Research*, 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for the identification of inhibitors of PAI-1 activity and for methods of using the identified inhibitors to modulate PAI-1 expression or activity in a subject in order to treat disorders associated with elevated PAI-1 levels.

SUMMARY

The present invention provides substituted oxadiazolidinediones and methods of using them. In certain embodiments, substituted oxadiazolidinediones of the invention include those of the following formula:

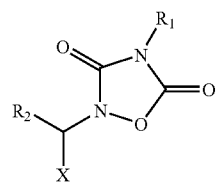

wherein:
$R_1$ is hydrogen or $-(CH_2)_n COOH$;
n is an integer from 1 to 3;
X is

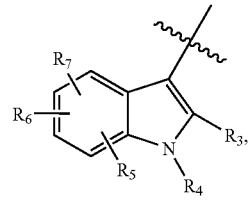
Formula A

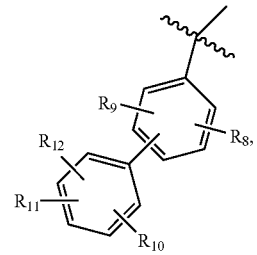
Formula B

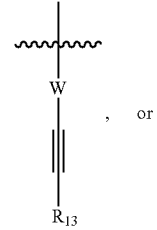
Formula C , or

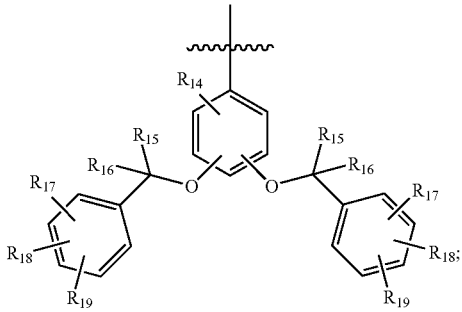
Formula D $R_2$ is hydrogen, $C_1$–$C_8$ alkyl, $C_3$–$C_6$ cycloalkyl, $-CH_2$–$C_3$–$C_6$ cycloalkyl, aryl, benzyl, heteroaryl or $-CH_2$-heteroaryl;

$R_3$ is hydrogen, $C_1$–$C_8$ alkyl, $C_3$–$C_6$ cycloalkyl, $-CH_2$–$C_3$–$C_6$ cycloalkyl, phenyl, benzyl, heteroaryl or $-CH_2$-heteroaryl;

$R_4$ is hydrogen, $C_1$–$C_8$ alkyl, $-(CH_2)_q-CH=CH_2$, $-(CH_2)_q-CH=CH$-alkyl, $-(CH_2)_q C\equiv CH$, —$(CH_2)_qC\equiv C$-alkyl, aryl, $(CH_2)_q$-aryl, heteroaryl, $(CH_2)_q$-heteroaryl, —CO-aryl, —CO-heteroaryl, —CO-alkyl, —$SO_2$-alkyl, —$SO_2$-aryl, or —$SO_2$-heteroaryl;

$R_5$, $R_6$, $R_7$, $R_8$, $R_9$, $R_{10}$, $R_{11}$, $R_{12}$, $R_{14}$, $R_{17}$, $R_{18}$ and $R_{19}$ are, independently, hydrogen, halogen, $C_1$–$C_6$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —$O(CH_2)_q$-aryl, —$O(CH_2)_q$-heteroaryl, aryl, or heteroaryl;

$R_{13}$ is hydrogen, $C_1$–$C_8$ alkyl, $C_2$–$C_8$ alkenyl, $C_2$–$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl;

q is an integer from 0 to 5;

m is an integer from 0 to 5;

$R_{15}$ and $R_{16}$ are, independently, hydrogen, $C_1$–$C_8$ alkyl, $C_3$–$C_6$ cycloalkyl, —$CH_2$—$C_3$–$C_6$ cycloalkyl, aryl, benzyl, heteroaryl or —$CH_2$-heteroaryl;

W is aryl or heteroaryl; and p is an integer from 1 to 5.

Accordingly, the present invention provides, inter alia, substituted indolylmethyl oxadiazolidinediones of the following formula:

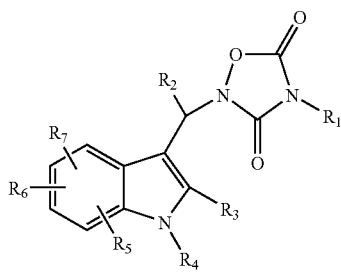

Formula 2 wherein $R_1$, $R_2$, $R_3$, $R_4$, $R_5$, $R_6$, and $R_7$ are defined as above.

In certain exemplary embodiments, $R_1$ is H; $R_2$ is H; $R_3$ is H; $R_4$ is $C_1$–$C_6$ alkyl, alkenyl (allyl), alkynyl (propargyl) or arylalkyl (benzyl); $R_5$ is H, $R_6$ is benzyloxy where the benzyl group is optionally substituted with one or more groups selected from halogen, $C_1$–$C_6$ straight chain alkyl or $C_1$–$C_6$ branched alkyl, $C_1$–$C_3$ perfluoroalkyl, —O—$C_1$–$C_3$ perfluoroalkyl, $C_1$–$C_6$ alkoxy, or naphthyl; and $R_7$ is H.

The present invention also provides, inter alia, substituted biphenylmethyl oxadiazolidinediones of the following formula:

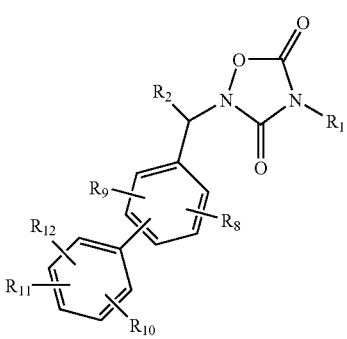

Formula 6 wherein $R_1$, $R_2$, $R_8$, $R_9$, $R_{10}$, $R_{11}$, and $R_{12}$ are defined as above.

In certain exemplary embodiments, $R_1$ is H; $R_2$ is H; $R_8$ is H; $R_9$ is H; $R_{10}$ is H; $R_{11}$ is benzyloxy where the benzyl group is optionally substituted with one or more groups selected from halogen, $C_1$–$C_6$ straight chain alkyl or $C_1$–$C_6$ branched alkyl, $C_1$–$C_3$ perfluoroalkyl, —O—$C_1$–$C_3$ perfluoroalkyl, $C_1$–$C_6$ alkoxy, or naphthyl; and $R_{12}$ is H.

The present invention also provides, inter alia, substituted acetylenic oxadiazolidinediones of the following formula:

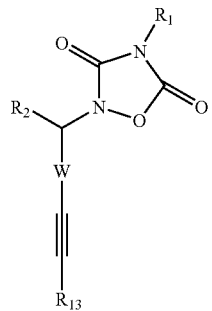

Formula 9 wherein $R_1$, $R_2$, $R_{13}$, and W are defined as above.

In certain exemplary embodiments, $R_1$ is H; $R_2$ is H; $R_{13}$ is $C_1$–$C_6$ is straight chain alkyl, $C_1$–$C_6$ branched alkyl, phenyl or —$(CH_2)$—O-aryl where the aryl group is optionally substituted with one or more groups selected from halogen, $C_1$–$C_6$ straight chain alkyl, $C_1$–$C_6$ branched alkyl, $C_1$–$C_3$ perfluoroalkyl, —O—$C_1$–$C_3$ perfluoroalkyl, $C_1$–$C_6$ alkoxy, or naphthyl; and W is aryl or heteroaryl.

The present invention also provides, inter alia, substituted bisbenzyloxybenzyl oxadiazolidinediones of the following formula:

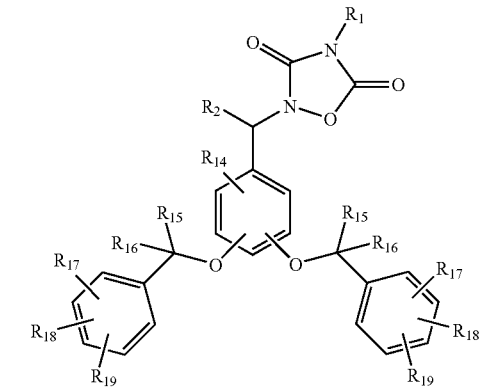

Formula 11 wherein $R_1$, $R_2$, $R_{14}$, $R_{15}$, $R_{16}$, $R_{17}$, $R_{18}$, and $R_{19}$ are defined as above.

In certain exemplary embodiments, $R_1$ is H; $R_2$ is H; $R_{14}$ is H or alkoxy; $R_{15}$ is H, $R_{16}$ is H, $R_{17}$, $R_{18}$ and $R_{19}$ are independently H, halogen, $C_1$–$C_6$ alkyl, $C_1$–$C_6$ alkoxy, $C_1$–$C_3$ perfluoroalkyl, or —O—$C_1$–$C_3$ perfluoroalkyl.

The present invention also provides, inter alia, pharmaceutically acceptable salt or ester forms of formulas 1–12.

The present invention further provides, inter alia, methods of using substituted oxadiazolidinediones. In one aspect of the present invention, a therapeutically effective amount of one or more substituted oxadiazolidinediones is administered to a subject in order to treat a PAI-1 related disorder, e.g., by inhibiting PAI-1 activity in the subject. PAI-1 activity is associated with a number of diseases and conditions. For example, in one embodiment of the present invention, PAI-1 activity is associated with impairment of the fibrinolytic system. In other embodiments, PAI-1 activity is associated with thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds in medical therapies. The compounds have properties that are useful for the treatment, including the prevention and inhibition, of a wide variety of diseases and disorders involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to about 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one double bond. Preferably, the alkenyl moiety has 1 or 2 double bonds. Such alkenyl moieties can exist in the E or Z conformations and the compounds of this invention include both conformations. Specifically included within the definition of "alkenyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond.

The term "alkynyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one triple bond. Preferably, the alkynyl moiety has 3 to about 6 carbon atoms. In certain embodiments, the alkynyl can contain more than one triple bond and, in such cases, the alknyl group must contain at least three carbon atoms. Specifically included within the definition of "alkynyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to about 20 carbon atoms (unless explicitly specified otherwise), preferably 3 to 8 carbon atoms. Specifically included within the definition of "cycloalkyl" are those alicyclic hydrocarbon groups that are optionally substituted. For example, in certain embodiments of the present invention, the rings of the cycloalkyl are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —CN, —COOH, —COOR wherein R is alkyl, or —$CONH_2$.

The term "aryl", as used herein, whether used alone or as part of another group, is defined as a substituted or unsubstituted aromatic hydrocarbon ring group having 5 to about 50 carbon atoms with from 6 to 14 carbon atoms being preferred. The "aryl" group can have a single ring or multiple condensed rings. The term "aryl" includes, but is not limited to phenyl, α-naphthyl, β-naphthyl, biphenyl, anthryl, tetrahydronaphthyl, phenanthryl, fluorenyl, indanyl, biphenylenyl, and acenaphthenyl. Specifically included within the definition of "aryl" are those aromatic groups that are optionally substituted. Accordingly, the aryl groups (e.g., phenyl) described herein refer to both unsubstituted or substituted groups. For example, in representative embodiments of the present invention, the, "aryl" groups are optionally substituted with from 1 to 5 substituents selected from the group consisting of acyloxy, hydroxy, acyl, aryl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Exemplary substituents on the aryl groups herein include alkyl, alkoxy, halo, cyano, nitro, trihalomethyl, and thioalkoxy. In certain embodiments of the present invention, the rings of the aryl groups are optionally substituted by 1 to 3 groups selected from halogen, $C_1$–$C_6$ alkyl, $C_1$–$C_3$ perfluoroalkyl, —O—$C_1$–$C_3$ perfluoroalkyl, $C_1$–$C_6$ alkoxy, naphthyl, —OH, —NH$_2$, —CN, or —NO$_2$.

The term "heteroaryl" as used herein is defined as a substituted or unsubstituted aromatic heterocyclic ring system (monocyclic or bicyclic). Heteroaryl groups can have, for example, from about 3 to about 50 carbon atoms (unless explicitly specified otherwise) with from 4 to 10 being preferred. In some embodiments, heteroaryl groups are aromatic heterocyclic rings systems having 4 to 14 ring atoms including carbon atoms and 1, 2, 3, or 4 heteroatoms independently selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl goups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic groups that are optionally substituted. Accordingly, the heteroaryl groups (e.g., pyridinyl) described herein refer to both unsubstituted or substituted groups. In representative embodiments of the present invention, the, "heteroaryl" groups are optionally substituted with 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In exemplary embodiments of the present invention, the rings of the heteroaryl group are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH$_2$, —CN, or —NO$_2$.

The term "alkoxy" as used herein, refers to the group $R_a$—O— wherein $R_a$ is an alkyl group as defined above. Specifically included within the definition of "alkoxy" are those alkoxy groups that are optionally substituted.

Exemplary substituents on the alkyl, alkenyl, alkynyl, thioalkoxy and alkoxy groups mentioned above include, but are not limited to, halogen, —O—$C_1$–$C_6$ alkyl, —NH—$C_1$–$C_6$ alkyl, —CN, —OH, amino groups, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

In exemplary embodiments of the present invention, the rings of the cycloalkyl, heteroaryl, phenyl and benzyl groups described herein are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —CN, —NH$_2$, or —NO$_2$.

The term "arylalkyl", as used herein, whether used alone or as part of another group, refers to the group -$R_a$-$R_b$, where $R_a$ is an alkyl group as defined above, substituted by $R_b$, an aryl group, as defined above. Examples of arylalkyl moieties include, but are not limited to, benzyl, 1-phenylethyl, 2-phenylethyl, 3-phenylpropyl, 2-phenylpropyl and the like.

The term "alkylheteroaryl", as used herein, whether used alone or as part of another group, refers to the group -$R_c$-$R_a$, where $R_c$ is a heteroaryl group as defined above, substituted with $R_a$, an alkyl group as defined above.

The term "heterocycle", as used herein, whether used alone or as part of another group, refers to a stable 3 to about 10-member ring containing carbons atoms and from 1 to 3 heteroatoms independently selected from the group consisting of nitrogen, phospohorus, oxygen, and sulfur. A heterocycle of this invention can be either a monocyclic or bicyclic ring system, and can be either saturated or partially saturated. Heterocycle groups include, but are not limited to, aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "perfluoroalkyl", as used herein, whether used alone or as part of another group, refers to a saturated aliphatic hydrocarbon having 1 to about 6 carbon atoms and two or more fluorine atoms and includes, but is not limited to, straight or branched chains, such as —CF$_3$, —CH$_2$CF$_3$, —CF$_2$CF$_3$ and —CH(CF$_3$)$_2$.

The term "halogen" or "halo" refers to chlorine, bromine, fluorine, and iodine.

The term "p" can be 1, 2, 3, 4, or 5. "q" can be 0, 1, 2, 3, 4, or 5. "m" can be 0, 1, 2, 3, 4, or 5.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1, e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Increased PAI-1 levels are indicative of disease. Accordingly, the present invention provides, inter alia, methods of administering a compound of the present invention to a subject and determining levels of PAI-1 in the subject. The level of PAI-1 in the subject can be determined before and/or after administration of the compound.

In healthy individuals, PAI-1 is found at low levels in the plasma (from about 5–26 ng/mL), but it is elevated in many PAI-1 related disorders, including, for example, atherosclerosis (Schneiderman J. et. al, *Proc Natl Acad Sci* 89: 6998–7002, 1992) deep vein thrombosis (Juhan-Vague I, et. al, *Thromb Haemost* 57: 67–72, 1987), and non-insulin dependent diabetes mellitus (Juhan-Vague I, et. al, *Thromb Haemost* 78: 565–660, 1997). PAI-1 stabilizes both arterial and venous thrombi, contributing respectively to coronary arterial occlusion in post-myocardial infarction (Hamsten A, et. al. *Lancet* 2:3–9, 1987), and venous thrombosis following post-operative recovery from orthopedic surgery. (Siemens H J, et. al, *J Clin Anesthesia* 11: 622–629, 1999). Plasma PAI-1 is also elevated, for example, in postmenopausal women, and has been proposed to contribute to the increased incidence of cardiovascular disease in this population (Koh K et. al, *N Engl J Med* 336: 683–690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression can include one or more of the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal or healthy subject is a subject not suffering from a PAI-1 related disorder or disease.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of basic moieties, such as amines, in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Inhibitors," "activators," and "modulators" of expression or of activity are used to refer to inhibitory, activating, or modulating molecules, respectively, identified using in vitro and in vivo assays for expression or activity. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means the amount that, when administered to a subject, produces effects for which it is administered. For example, a "therapeutically effective amount," when administered to a subject to inhibit PAI-1 activity, is sufficient to inhibit PAI-1 activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that can be associated with the targeted or suspected disease or condition. These and other routine methods allow the clinician to select patients in need of therapy using the methods and formulations of the present invention.

When any variable occurs more than one time in any constituent or in any formula, its definition in each occurrence is independent of its definition at every other occurrence. Combinations of substituents and/or variables are permissible only if such combinations result in stable compounds.

B. Substituted Oxadiazolidinediones

The present invention provides substituted oxadiazolidinediones. Such compounds are preferably administered to inhibit PAI-1 expression or activity in a subject and, ultimately, to treat diseases or conditions associated with increased PAI-1 activity in a subject, e.g., a PAI-1 related disorder.

Substituted oxadiazolidinediones include those of the following formula:

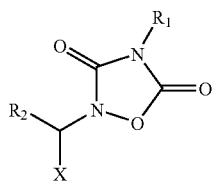

Formula 1 wherein:

$R_1$ is hydrogen or $—(CH_2)_n COOH$;

n is an integer from 1 to 3;

X is

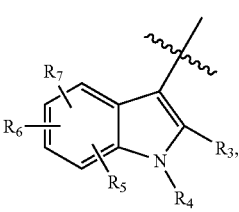

Formula A

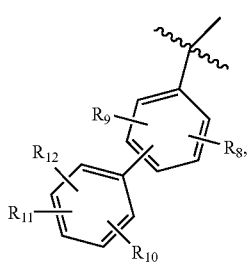

Formula B

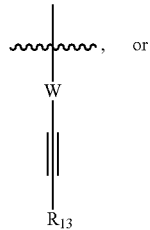

Formula C

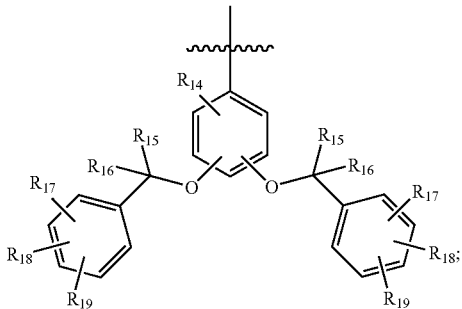

Formula D $R_2$ is hydrogen, $C_1–C_8$ alkyl, $C_3–C_6$ cycloalkyl, $—CH_2—C_3–C_6$ cycloalkyl, pyridin $—CH_2$-pyridinyl, aryl, benzyl, heteroaryl or $—CH_2$-heteroaryl;

$R_3$ is hydrogen, $C_1–C_8$ alkyl, $C_3–C_6$ cycloalkyl, $—CH_2—C_3–C_6$ cycloalkyl, pyridin $—CH_2$-pyridinyl, phenyl, benzyl, heteroaryl or $—CH_2$-heteroaryl;

$R_4$ is hydrogen, $C_1–C_8$ alkyl, $—(CH_2)_q—CH=CH_2$, $—(CH_2)_q—CH=CH$-alkyl, $—(CH_2)_q C\equiv CH$, $—(CH_2)_q C\equiv C$-alkyl, aryl, $(CH_2)_q$-aryl, heteroaryl, $(CH_2)_q$-heteroaryl, $—CO$-aryl, $—CO$-heteroaryl, $—CO$-alkyl, $—SO_2$-alkyl, $—SO_2$-aryl, or $—SO_2$-heteroaryl;

$R_5$, $R_6$, $R_7$, $R_8$, $R_9$, $R_{10}$, $R_{11}$, $R_{12}$, $R_{14}$, $R_{17}$, $R_{18}$ and $R_{19}$ are, independently, hydrogen, halogen, $C_1–C_6$ alkyl, $C_1–C_3$ perfluoroalkyl, $—O—C_1–C_3$ perfluoroalkyl, $C_1–C_3$ alkoxy, $—OH$, $—NH_2$, $—NO_2$, $—O(CH_2)_q$-aryl, $—O(CH_2)_q$-heteroaryl, aryl, or heteroaryl;

$R_{13}$ is hydrogen, $C_1–C_8$ alkyl, $C_1–C_8$ alkenyl, $C_1–C_8$ alkynyl, $—(CH_2)_p$-aryl, $—(CH_2)_p$-heteroaryl, $—(CH_2)_p—O$-aryl, $—(CH_2)_p—O$-heteroaryl, $—(CH_2)_p—O—(CH_2)_m$-aryl, $—(CH_2)_p—O—(CH_2)_m$-heteroaryl, aryl, or heteroaryl;

q is an integer from 0 to 5;

m is an integer from 0 to 5;

$R_{15}$ and $R_{16}$ are, independently, hydrogen, $C_1–C_8$ alkyl, $C_3–C_6$ cycloalkyl, $—CH_2—C_3–C_6$ cycloalkyl, pyridinyl, $—CH_2$-pyridinyl, aryl, benzyl, heteroaryl or $—CH_2$-heteroaryl;

W is aryl or heteroaryl; and p is an integer from 1 to 5.

Accordingly, in some embodiments, substituted oxadiazolidinediones of the present invention include substituted indolylmethyl oxadiazolidinediones of the following formula:

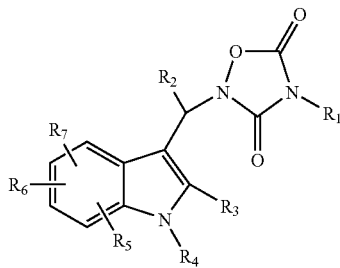

Formula 2 wherein $R_1$, $R_2$, $R_3$, $R_4$, $R_5$, $R_6$, $R_7$, n, and q are as defined above for Formula 1.

Compounds of the present invention also include prodrugs, stereoisomers, or pharmaceutically acceptable salts or ester forms of formula 2.

For use in the present invention, when the substituted oxadiazolidenedione is represented by Formula 2, $R_1$ can be hydrogen or —$(CH_2)_n$COOH and n can be 0, 1, 2, or 3. $R_2$, $R_3$, $R_4$, $R_5$, $R_6$, $R_7$, and q are as defined herein for Formula 2.

$R_2$ can be hydrogen, $C_1$–$C_8$ alkyl, $C_3$–$C_6$ cycloalkyl, —$CH_2$—$C_3$–$C_6$ cycloalkyl, aryl benzyl, heteroaryl or —$CH_2$-heteroaryl. In certain embodiments of compounds of formula 2, $R_2$ is $C_3$–$C_6$ cycloalkyl, —$CH_2$—$C_3$–$C_6$ cycloalkyl, pyridinyl, —$CH_2$-pyridinyl, phenyl or benzyl wherein the rings of the cycloalkyl, pyridinyl, aryl and/or benzyl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain compounds, $R_2$ is hydrogen, $C_3$–$C_6$ cycloalkyl, —$CH_2$—$C_3$–$C_6$ cycloalkyl, aryl, benzyl, heteroaryl or —$CH_2$-heteroaryl. In certain preferred embodiments, $R_2$ is alkyl or hydrogen. Most preferably, $R_2$ is hydrogen. In such embodiments, $R_1$, $R_3$, $R_4$, $R_5$, $R_6$, $R_7$, n, and q are as defined herein for Formula 2.

$R_3$ can be hydrogen, $C_1$–$C_8$ alkyl, $C_3$–$C_6$ cycloalkyl, —$CH_2$—$C_3$–$C_6$ cycloalkyl, phenyl, benzyl, heteroaryl or —$CH_2$-heteroaryl. In certain embodiments of compounds of formula 2, $R_3$ is $C_3$–$C_6$ cycloalkyl, —$CH_2$—$C_3$–$C_6$ cycloalkyl, pyridinyl, —$CH_2$-pyridinyl, phenyl or benzyl wherein the rings of the cycloalkyl, pyridinyl, phenyl and/or benzyl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments, $R_3$ is alkyl or hydrogen. Most preferably, $R_3$ is hydrogen. In such embodiments, $R_1$, $R_2$, $R_4$, $R_5$, $R_6$, $R_7$, n, and q are as defined herein for Formula 2.

$R_4$ can be hydrogen, $C_1$–$C_8$ alkyl, —$(CH_2)_q$—CH═CH, —$(CH_2)_q$—CH═C-alkyl, —$(CH_2)_q$C≡CH, —$(CH_2)_q$C≡C-alkyl, aryl, $(CH_2)_q$-aryl, heteroaryl, $(CH_2)_q$-heteroaryl, —CO-aryl, —CO-heteroaryl, —CO-alkyl, —$SO_2$-alkyl, —$SO_2$-aryl, or —$SO_2$-heteroaryl. In certain embodiments of compounds of formula 2, $R_4$ is aryl, $(CH_2)_q$-aryl, heteroaryl, $(CH_2)_q$-heteroaryl, —CO-aryl, —CO-heteroaryl, —CO-alkyl, $SO_2$-aryl, and $SO_2$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments, $R_4$ is aralkyl, alkyl, alkenyl, alkynyl, or $SO_2$ alkyl. Most preferably, $R_4$ is benzyl, allyl, ethyl, propargyl, or methyl. In such embodiments, $R_1$, $R_2$, $R_3$, $R_5$, $R_6$, $R_7$, n, and q are as defined herein for Formula 2.

For use in the present invention, $R_5$, $R_6$, $R_7$, $R_8$, $R_9$, $R_{10}$, $R_{11}$, $R_{12}$, $R_{14}$, $R_{17}$, $R_{18}$ and $R_{19}$ can be hydrogen, halogen, $C_1$–$C_6$ alkyl, $C_1$–$C_3$ perfluoroalkyl, —O—$C_{1-C3}$ perfluoroalkyl, $C_1$–$C_3$ alkoxy, —OH, —$NH_2$, —$NO_2$, —$O(CH_2)_q$-aryl, —$O(CH_2)_q$-heteroaryl, aryl, or heteroaryl.

In certain embodiments of compounds of formula 2, $R_5$ is aryl, —$O(CH_2)_q$-aryl, heteroaryl, —$O(CH_2)_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments $R_5$ is $C_1$–$C_6$ alkyl, halogen, $C_1$–$C_3$ perfluoroalkyl, —O—$C_1$–$C_3$ perfluoroalkyl, or $C_1$–$C_3$ alkoxy. Most preferably, $R_5$ is hydrogen. In such embodiments, $R_1$, $R_2$, $R_3$, $R_4$, $R_6$, $R_7$, n, and q are as defined herein for Formula 2.

In certain embodiments of compounds of formula 2, $R_6$ is aryl, —$O(CH_2)_q$-aryl, heteroaryl, —$O(CH_2)_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments, $R_6$ is —$O(CH_2)_q$-aryl wherein the ring of the aryl group is optionally substituted with 1 to 3 groups selected from alkyl, perfluoroalkyl, halogen, or aryl. Most preferably, $R_6$ is benzyloxy wherein the benzyl group is optionally substituted with 1 to 3 groups selected from butyl, $CF_3$, bromine, chlorine, methyl, and naphthyl. In such embodiments, $R_1$, $R_2$, $R_3$, $R_4$, $R_5$, $R_7$, n, and q are as defined herein for Formula 2.

In certain embodiments of compounds of formula 2, $R_7$ is aryl, —$O(CH_2)_q$-aryl, heteroaryl, —$O(CH_2)_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments, $R_7$ is $C_1$–$C_6$ alkyl, halogen, $C_1$–$C_3$ perfluoroalkyl, —O—$C_1$–$C_3$ perfluoroalkyl, or $C_1$–$C_3$ alkoxy. Most preferably $R_7$ is hydrogen. In such embodiments, $R_1$, $R_2$, $R_3$, $R_4$, $R_5$, $R_6$, n, and q are as defined herein for Formula 2.

In certain embodiments of the present invention, such substituted indolylmethyl oxadiazolidinediones include the following compounds:

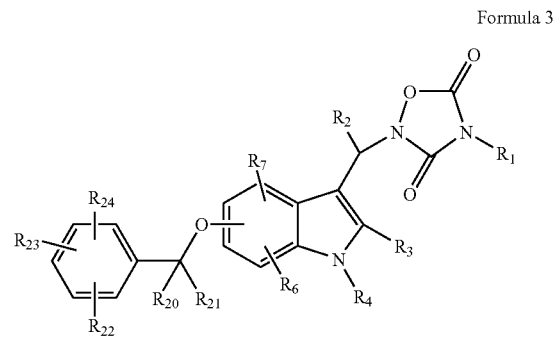

Formula 3

Formula 4

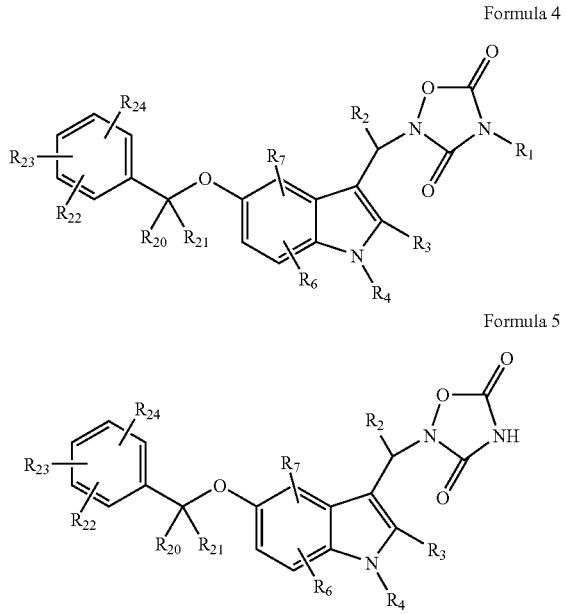

Formula 5 wherein R$_1$, R$_2$, R$_3$, R$_4$, R$_6$, and R$_7$ are defined as above, and

R$_{20}$ and R$_{21}$ can be hydrogen, C$_1$–C$_8$ alkyl, —CH$_2$—C$_3$–C$_6$ cycloalkyl, —CH$_2$-pyridinyl, phenyl, or benzyl;

R$_{22}$, R$_{23}$ and R$_{24}$ can be hydrogen, halogen, C$_1$–C$_6$ alkyl (preferably C$_1$–C$_3$ alkyl), C$_1$–C$_3$ perfluoroalkyl, —O—C$_1$–C$_3$ perfluoroalkyl, C$_1$–C$_6$ alkoxy (preferably C$_1$–C$_3$ alkoxy), —OH, —NH$_2$, —NO$_2$, —O(CH$_2$)$_q$-aryl, —O(CH$_2$)$_q$-heteroaryl, aryl, or heteroaryl;

and q is an integer from 0 to 5.

In certain exemplary embodiments, the rings of the aryl and heteroaryl groups represented by R$_{22}$, R$_{23}$ and R$_{24}$ are optionally substituted by 1 to 3 groups selected from halogen, C$_1$–C$_3$ alkyl, C$_1$–C$_3$ perfluoroalkyl, —O—C$_1$–C$_3$ perfluoroalkyl, C$_1$–C$_3$ alkoxy, —OH, —NH$_2$, or —NO$_2$ or a pharmaceutically acceptable salt or ester form thereof and/or the rings of the cycloalkyl, pyridinyl, phenyl, and benzyl groups represented by R$_{20}$ and R$_{21}$ are optionally substituted by 1 to 3 groups selected from halogen, C$_1$–C$_3$ alkyl, C$_1$–C$_3$ perfluoroalkyl, —O—C$_1$–C$_3$ perfluoroalkyl, C$_1$–C$_3$ alkoxy, —OH, —NH$_2$, or —NO$_2$.

In certain embodiments of the present invention,

R$_1$ is hydrogen or —(CH$_2$)$_n$COOH;

R$_2$ is hydrogen, C$_1$–C$_8$ alkyl, C$_3$–C$_6$ cycloalkyl, —CH$_2$—C$_3$–C$_6$ cycloalkyl, aryl, benzyl, pyridinyl or —CH$_2$-pyridinyl wherein the rings of the cycloalkyl, pyridinyl, aryl and/or benzyl groups are optionally substituted by 1 to 3 groups selected from halogen, unsubstituted C$_1$–C$_3$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, or —NO$_2$;

R$_3$ is hydrogen, unsubstituted C$_1$–C$_8$ alkyl, C$_3$–C$_6$ cycloalkyl, —CH$_2$—C$_3$–C$_6$ cycloalkyl, phenyl, benzyl, pyridinyl or —CH$_2$-pyridinyl wherein the rings of the cycloalkyl, pyridinyl, aryl and/or benzyl groups are optionally substituted by 1 to 3 groups selected from halogen, unsubstituted C$_1$–C$_3$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, or —NO$_2$;

R$_4$ is hydrogen, C$_1$–C$_8$ alkyl, —(CH$_2$)$_q$—CH═CH$_2$, -unsubstituted (CH$_2$)$_q$—CH═CH-alkyl, —(CH$_2$)$_q$C≡CH$_2$, unsubstituted —(CH$_2$)$_q$C≡C-alkyl, aryl, (CH$_2$)$_q$-aryl, heteroaryl, (CH$_2$)$_q$-heteroaryl, —CO-aryl, —CO-heteroaryl, unsubstituted —CO-alkyl, unsubstituted —SO$_2$-alkyl, —SO$_2$-aryl, or —SO$_2$-heteroaryl wherein the rings of the aryl and heteroaryl groups are optionally substituted by 1 to 3 groups selected from halogen, unsubstituted C$_1$–C$_3$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, or —NO$_2$;

R$_5$, R$_6$, R$_7$, are, independently, hydrogen, halogen, unsubstituted C$_1$–C$_6$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, —NO$_2$, —O(CH$_2$)$_q$-aryl, —O(CH$_2$)$_q$-heteroaryl, aryl, or heteroaryl wherein the rings of the aryl and heteroaryl groups are optionally substituted by 1 to 3 groups selected from halogen, unsubstituted C$_1$–C$_3$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, or —NO$_2$;

R$_{20}$ and R$_{21}$ are hydrogen, unsubstituted C$_1$–C$_8$ alkyl, —CH$_2$—C$_3$–C$_6$ cycloalkyl, —CH$_2$-pyridinyl, phenyl, or benzyl wherein the rings of the cycloalkyl, pyridinyl, aryl and/or benzyl groups are optionally substituted by 1 to 3 groups selected from halogen, unsubstituted C$_1$–C$_3$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, or —NO$_2$;

R$_{22}$, R$_{23}$ and R$_{24}$ are hydrogen, halogen, unsubstituted C$_1$–C$_6$ alkyl (preferably C$_1$–C$_3$ alkyl), unsubstituted C$_1$–C$_3$ perfluoroalkyl, unsubstituted —O—C$_1$–C$_3$ perfluoroalkyl, unsubstituted C$_1$–C$_6$ alkoxy (preferably C$_1$–C$_3$ alkoxy), —OH, —NH$_2$, —NO$_2$, —O(CH$_2$)$_q$-aryl, —O(CH$_2$)$_q$-heteroaryl, aryl, or heteroaryl wherein the rings of the aryl or heteroaryl groups are optionally substituted by 1 to 3 groups selected from halogen, unsubstituted C$_1$–C$_3$ alkyl, unsubstituted C$_1$–C$_3$ perfluoroalkyl, unsubstituted —O—C$_1$–C$_3$ perfluoroalkyl, unsubstituted C$_1$–C$_3$ alkoxy, —OH, —NH$_2$, or —NO$_2$.

Exemplary substituted indolylmethyl oxadiazolidinediones of the present invention include, but are not limited to, 2-({1-benzyl-5-[(4-tert-butylbenzyl)oxy]-1H-indol-3-yl}methyl)-1,2,4-oxadiazolidine-3,5-dione or a pharmaceutically acceptable salt or ester form thereof; 2-({1-allyl-5-[(4-tert-butylbenzyl)oxy]-1H-indol-3-yl}methyl)-1,2,4-oxadiazolidine-3,5-dione or a pharmaceutically acceptable salt or ester form thereof; 2-({5-[(4-tert-butylbenzyl)oxy]-1-ethyl-1H-indol-3-yl}methyl)-1,2,4-oxadiazolidine-3,5-dione or a pharmaceutically acceptable salt or ester form thereof; 2-[(1-allyl-5-{[4-(trifluoromethyl)benzyl]oxy}-1H-indol-3-yl)methyl]-1,2,4-oxadiazolidine-3,5-dione or a pharmaceutically acceptable salt or ester form thereof; 2-[(1-allyl-5-{[3,5-bis(trifluoromethyl)benzyl]oxy}-1H-indol-3-yl)methyl]-1,2,4-oxadiazolidine-3,5-dione or a pharmaceutically acceptable salt or ester form thereof; 2-[(5-{[3,5-bis(trifluoromethyl)benzyl]oxy}-1-ethyl-1H-indol-3-yl)methyl]-1,2,4-oxadiazolidine-3,5-dione or a pharmaceutically acceptable salt or ester form thereof; 2-[(1-benzyl-5-{[3,5-bis(trifluoromethyl)benzyl]oxy}-1H-indol-3-yl)methyl]-1,2,4-oxadiazolidine-3,5-dione or a pharmaceutically acceptable salt or ester form thereof; 2-({1-benzyl-5-[(3-bromobenzyl)oxy]-1H-indol-3-yl}methyl)-1,2,4-oxadiazolidine-3,5-dione or a pharmaceutically acceptable salt or ester form thereof; 2-({1-benzyl-5-[(3-chlorobenzyl)oxy]-1H-indol-3-yl}methyl)-1,2,4-oxadiazolidine-3,5-dione or a pharmaceutically acceptable salt or ester form thereof; 2-[(1-benzyl-5-{[3-(trifluoromethyl)benzyl]oxy}-1H-indol-3-yl)methyl]-1,2,4-oxadiazolidine-3,5- dione or a pharmaceutically acceptable salt or ester form thereof; 2-({1-benzyl-5-[(3-methylbenzyl)oxy]-1H-indol-3-yl}methyl)-1,2,4-oxadiazolidine-3,5-dione or a pharmaceutically acceptable salt or ester form thereof; 2-[(1-(2-propynyl)-5-{[4-(trifluoromethyl)benzyl]oxy}-1H-indol-3-yl) methyl]-1,2,4-oxadiazolidine-3,5-dione or a pharmaceutically acceptable salt or ester form thereof; 2-[(1-benzyl-5-{[4-(trifluoromethyl)benzyl]oxy}-1H-indol-3-yl) methyl]-1,2,4-oxadiazolidine-3,5-dione or a pharmaceutically acceptable salt or ester form thereof; 2-({1-benzyl-5-[(4-bromobenzyl)oxy]-1H-indol-3-yl}methyl)-1,2,4-oxadiazolidine-3,5-dione or a pharmaceutically acceptable salt or ester form thereof; 2-{[5-{[3,5-bis(trifluoromethyl)benzyl]oxy}-1-(2-propynyl)-1H-indol-3-yl]methyl}-1,2,4-oxadiazolidine-3,5-dione or a pharmaceutically acceptable salt or ester form thereof; 2-[(5-{[3,5-bis(trifluoromethyl)benzyl]oxy}-1-methyl-1H-indol-3-yl)methyl]-1,2,4-oxadiazolidine-3,5-dione or a pharmaceutically acceptable salt or ester form thereof; 2-{[5-[(2-chlorobenzyl)oxy]-1-(2-propynyl)-1H-indol-3-yl]methyl}-1,2,4-oxadiazolidine-3,5-dione or a pharmaceutically acceptable salt or ester form thereof; 2-{[5-[(3,4-dichlorobenzyl)oxy]-1-(2-propynyl)-1H-indol-3-yl]methyl}-1,2,4-oxadiazolidine-3,5-dione or a pharmaceutically acceptable salt or ester form thereof; 2-({1-benzyl-5-[(3,4-dichlorobenzyl)oxy]-1H-indol-3-yl}methyl)-1,2,4-oxadiazolidine-3,5-dione or a pharmaceutically acceptable salt or ester form thereof; 2-{[5-(2-naphthylmethoxy)-1-(2-propynyl)-1H-indol-3-yl]methyl}-1,2,4-oxadiazolidine-3,5-dione or a pharmaceutically acceptable salt or ester form thereof; 2-{[1-allyl-5-(2-naphthylmethoxy)-1H-indol-3-yl]methyl}-1,2,4-oxadiazolidine-3,5-dione or a pharmaceutically acceptable salt or ester form thereof; 2-{[1-benzyl-5-(2-naphthylmethoxy)-1H-indol-3-yl]methyl}-1,2,4-oxadiazolidine-3,5-dione or a pharmaceutically acceptable salt or ester form thereof; 2-{[5-[(4-tert-butylbenzyl)oxy]-1-(2-propynyl)-1H-indol-3-yl]methyl}-1,2,4-oxadiazolidine-3,5-dione or a pharmaceutically acceptable salt or ester form thereof; 2-{[5-[(4-bromobenzyl)oxy]-1-(2-propynyl)-1H-indol-3-yl]methyl}-1,2,4-oxadiazolidine-3,5-dione or a pharmaceutically acceptable salt or ester form thereof; 2-({1-allyl-5-[(4-bromobenzyl)oxy]-1H-indol-3-yl}methyl)-1,2,4-oxadiazolidine-3,5-dione or a pharmaceutically acceptable salt or ester form thereof; 2-{[5-[(3-bromobenzyl)oxy]-1-(2-propynyl)-1H-indol-3-yl]methyl}-1,2,4-oxadiazolidine-3,5-dione or a pharmaceutically acceptable salt or ester form thereof; 2-({1-allyl-5-[(3-bromobenzyl)oxy]-1H-indol-3-yl}methyl)-1,2,4-oxadiazolidine-3,5-dione or a pharmaceutically acceptable salt or ester form thereof; 2-{[5-[(3-chlorobenzyl)oxy]-1-(2propynyl)-1H-indol-3-yl]methyl}-1,2,4-oxadiazolidine-3,5-dione or a pharmaceutically acceptable salt or ester form thereof; 2-[(1-allyl-5-{[3-(trifluoromethyl)benzyl]oxy}-1H-indol-3-yl)methyl]-1,2,4-oxadiazolidine-3,5-dione or a pharmaceutically acceptable salt or ester form thereof; 2-{[5-[(4-chlorobenzyl)oxy]-1-(2-propynyl)-1H-indol-3-yl]methyl}-1,2,4-oxadiazolidine-3,5-dione or a pharmaceutically acceptable salt or ester form thereof; 2-({1-allyl-5-[(4-chlorobenzyl)oxy]-1H-indol-3-yl}methyl)-1,2,4-oxadiazolidine-3,5-dione or a pharmaceutically acceptable salt or ester form thereof; 2-({1-benzyl-5-[(4-chlorobenzyl)oxy]-1H-indol-3-yl}methyl)-1,2,4-oxadiazolidine-3,5-dione or a pharmaceutically acceptable salt or ester form thereof; 2-({1-allyl-5-[(2-chlorobenzyl)oxy]-1H-indol-3-yl}methyl)-1,2,4-oxadiazolidine-3,5-dione or a pharmaceutically acceptable salt or ester form thereof; 2-({1-allyl-5-[(3,4-dichlorobenzyl)oxy]-1H-indol-3-yl}methyl)-1,2,4-oxadiazolidine-3,5-dione or a pharmaceutically acceptable salt or ester form thereof; and 2-({5-[(3,4-dichlorobenzyl)oxy]-1-methyl-1H-indol-3-yl}methyl)-1,2,4-oxadiazolidine-3,5-dione or a pharmaceutically acceptable salt or ester form thereof.

In alternative embodiments of the present invention, substituted oxadiazolidinediones include substituted biphenylmethyl oxadiazolidinediones of the following formula:

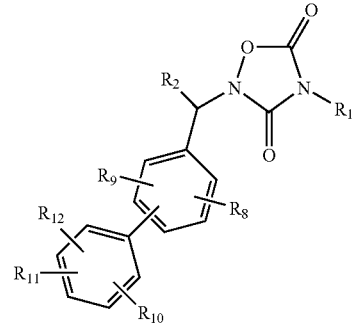

Formula 6 wherein $R_1$, $R_2$, $R_8$, $R_9$, $R_{10}$, $R_{11}$, $R_{12}$, n, and q are as defined above for Formula 1.

Compounds of the present invention also include prodrugs, stereoisomers, or pharmaceutically acceptable salts or ester forms of formula 6.

For use in the present invention, when the oxadiazolidenedione is represented by Formula 6, $R_1$ can be hydrogen or —$(CH_2)_n$COOH and n can be 0, 1, 2, or 3. In such embodiments, $R_2$, $R_8$, $R_9$, $R_{10}$, $R_{11}$, $R_{12}$, n, and q are as defined herein for Formula 6.

In certain embodiments of compounds of formula 6, $R_2$ is $C_3$–$C_6$ cycloalkyl, —$CH_2$—$C_3$–$C_6$ cycloalkyl, pyridinyl, —$CH_2$-pyridinyl, phenyl or benzyl wherein the rings of the cycloalkyl, pyridinyl, phenyl and/or benzyl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments $R_2$ is alkyl or hydrogen. Most preferably, $R_2$ is hydrogen. In such embodiments, $R_1$, $R_8$, $R_9$, $R_{10}$, $R_{11}$, $R_{12}$, n, and q are as defined herein for Formula 6.

In certain embodiments of compounds of formula 6, $R_8$ is aryl, —$O(CH_2)_q$-aryl, heteroaryl, or —$O(CH_2)_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments, $R_8$ is alkyl, halogen, $C_1$–$C_3$ perfluoroalkyl, —O—$C_1$–$C_3$ perfluoroalkyl, or $C_1$–$C_3$ alkoxy. Most preferably $R_8$ is hydrogen. In such embodiments, $R_1$, $R_2$, $R_9$, $R_{10}$, $R_{11}$, $R_{12}$, n, and q are as defined herein for Formula 6.

In certain embodiments of compounds of formula 6, $R_9$ is aryl, —$O(CH_2)_q$-aryl, heteroaryl, or —$O(CH_2)_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain preferred embodiments, $R_9$ is alkyl, halogen, $C_1$–$C_3$ perfluoroalkyl, —O—$C_1$–$C_3$ perfluoroalkyl, or $C_1$–$C_3$ alkoxy. Most preferably $R_9$ is hydrogen. In such embodiments, $R_1$, $R_2$, $R_8$, $R_{10}$, $R_{11}$, $R_{12}$, n, and q are as defined herein for Formula 6.

In certain embodiments of compounds of formula 6, $R_{10}$ is aryl, —O(CH$_2$)$_q$-aryl, heteroaryl, or —O(CH$_2$)$_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH$_2$, or —NO$_2$. In certain preferred embodiments, $R_{10}$ is alkyl, halogen, $C_1$–$C_3$ perfluoroalkyl, —O—$C_1$–$C_3$ perfluoroalkyl, or $C_1$–$C_3$ alkoxy. Most preferably $R_{10}$ is hydrogen. In such embodiments, $R_1$, $R_2$, $R_8$, $R_9$, $R_{11}$, $R_{12}$, n, and q are as defined herein for Formula 6.

In certain embodiments of compounds of formula 6, $R_{11}$, is aryl, —O(CH$_2$)$_q$-aryl, heteroaryl, or —O(CH$_2$)$_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH$_2$, or —NO$_2$. In certain preferred embodiments, $R_{11}$, is alkyl, halogen, $C_1$–$C_3$ perfluoroalkyl, —O—$C_1$–$C_3$ perfluoroalkyl, or $C_1$–$C_3$ alkoxy. Preferably $R_{11}$ is —O(CH$_2$)$_q$-aryl wherein the ring of the aryl group is optionally substituted with 1 to 3 groups selected from alkyl, oxadiazolidene, halogen, or aryl. Most preferably, $R_{11}$ is benzyloxy wherein the benzyl group is optionally substituted with 1 to 3 groups selected from butyl, CF$_3$, bromine, chlorine, methyl, and naphthyl. In such embodiments, $R_1$, $R_2$, $R_8$, $R_9$, $R_{10}$, $R_{12}$, n, and q are as defined herein for Formula 6.

In certain embodiments of compounds of formula 6, $R_{12}$ is aryl, —O(CH$_2$)$_q$-aryl, heteroaryl, or —O(CH$_2$)$_q$-heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH$_2$, or —NO$_2$. In certain preferred embodiments, $R_{12}$ is alkyl, halogen, $C_1$–$C_3$ perfluoroalkyl, —O—$C_1$–$C_3$ perfluoroalkyl, or $C_1$–$C_3$ alkoxy. Most preferably $R_{12}$ is hydrogen. In such embodiments, $R_1$, $R_2$, $R_8$, $R_9$, $R_{10}$, $R_{11}$, n, and q are as defined herein for Formula 6.

In certain embodiments, such substituted biphenylmethyl oxadiazolidenediones include the following compounds:

Formula 7

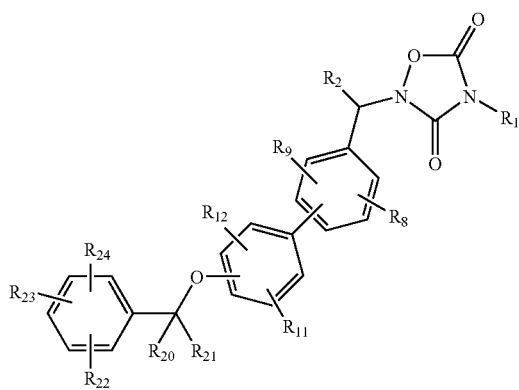

-continued

Formula 8

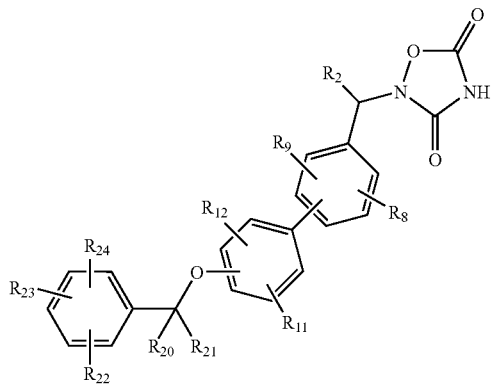

wherein $R_1$, $R_2$, $R_8$, $R_9$, $R_{11}$, $R_{12}$, $R_{20}$, $R_{21}$, $R_{22}$, $R_{23}$, and $R_{24}$ and Formulas 3–5.

In certain embodiments of the present invention $R_1$ is hydrogen or —(CH$_2$)$_n$COOH;

$R_2$ is hydrogen, $C_1$–$C_8$ alkyl, $C_3$–$C_6$ cycloalkyl, —CH$_2$—$C_3$–$C_6$ cycloalkyl, aryl, benzyl, pyridinyl or —CH$_2$-pyridinyl wherein the rings of the cycloalkyl, pyridinyl, aryl and/or benzyl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —NH$_2$, or —NO$_2$;

$R_8$, $R_9$, $R_{10}$, $R_{11}$, and $R_{12}$ are, independently, hydrogen, halogen, unsubstituted $C_1$–$C_6$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —NH$_2$, —NO$_2$, —O(CH$_2$)$_q$-aryl, —O(CH$_2$)$_q$-heteroaryl, aryl, or heteroaryl wherein the rings of the aryl and heteroaryl groups are optionally substituted by 1 to 3 groups selected from halogen, unsubstituted $C_{1–C3}$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —NH$_2$, or —NO$_2$ $R_{22}$, $R_{23}$ and $R_{24}$ are hydrogen, halogen, unsubstituted $C_1$–$C_6$ alkyl (preferably $C_1$–$C_3$ alkyl), unsubstituted $C_1$–$C_3$ perfluoroalkyl, unsubstituted —O—$C_1$–$C_3$ perfluoroalkyl, unsubstituted $C_1$–$C_6$ alkoxy (preferably $C_1$–$C_3$ alkoxy), —OH, —NH$_2$, —NO$_2$, —O(CH$_2$)$_q$-aryl, —O(CH$_2$)$_q$-heteroaryl, aryl, or heteroaryl wherein the rings of the aryl or heteroaryl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —NH$_2$, or —NO$_2$; and $R_{20}$ and $R_{21}$ are hydrogen, unsubstituted $C_1$–$C_8$ alkyl, —CH$_2$—$C_3$–$C_6$ cycloalkyl, —CH$_2$-pyridinyl, phenyl, or benzyl wherein the rings of the cycloalkyl, pyridinyl, aryl and/or benzyl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —NH$_2$, or —NO$_2$.

Exemplary substituted biphenylmethyl oxadiazolidenediones of the present invention include, but are not limited to, 2-({3'-[(2-chlorobenzyl)oxy]-1,1'-biphenyl-3-yl}methyl)-1, 2,4-oxadiazolidine-3,5-dione or a pharmaceutically acceptable salt or ester form thereof; 2-[(3'-{[4-(trifluoromethyl)benzyl]oxy}-1,1'-biphenyl-3-yl)methyl]-1,2,4-oxadiazolidine-3,5-dione or a pharmaceutically acceptable salt or ester form thereof; 2-[(3'-{[3,5-bis(trifluoromethyl)benzyl]oxy}-1,1'-biphenyl-3-yl)methyl]-1,2,4-oxadiazolidine-3,5-dione or a pharmaceutically acceptable salt or ester form thereof; 2-({3'-[(3-chlorobenzyl)oxy]-1,1'-biphenyl-3-yl}methyl)-1,2,4-oxadiazolidine-3,5-dione or a pharmaceutically acceptable salt or ester form thereof; 2-{[3'-(benzyloxy)-1,1'-biphenyl-3-yl]methyl}-1,2,4-oxadiazolidine-3,5-dione or a pharmaceutically acceptable salt or ester form thereof; 2-[(3'-{[3-(trifluoromethyl)benzyl]oxy}-1,1'-biphenyl-3-yl)methyl]-1,2,4-oxadiazolidine-3,5-dione or a pharmaceutically acceptable salt or ester form thereof; 2-({3'-[(4-chlorobenzyl)oxy]-1,1'-biphenyl-3-yl}methyl)-1,2,4-oxadiazolidine-3,5-dione or a pharmaceutically acceptable salt or ester form thereof; 2-({3'-[(3,4-dichlorobenzyl)oxy]-1,1'-biphenyl-3-yl}methyl)-1,2,4-oxadiazolidine-3,5-dione or a pharmaceutically acceptable salt or ester form thereof; 2-{[3'-(2-naphthylmethoxy)-1,1'-biphenyl-3-yl]methyl}-1,2,4-oxadiazolidine-3,5-dione or a pharmaceutically acceptable salt or ester form thereof; 2-({3'-[(4-methylbenzyl)oxy]-1,1'-biphenyl-3-yl}methyl)-1,2,4-oxadiazolidine-3,5-dione or a pharmaceutically acceptable salt or ester form thereof; 2-({3'-[(3-methylbenzyl)oxy]-1,1'-biphenyl-3-yl}methyl)-1,2,4-oxadiazolidine-3,5-dione or a pharmaceutically acceptable salt or ester form thereof; 2-({3'-[(2,6-dichlorobenzyl)oxy]-1,1'-biphenyl-3-yl}methyl)-1,2,4-oxadiazolidine-3,5-dione or a pharmaceutically acceptable salt or ester form thereof; 2-({4'-[(4-tert-butylbenzyl)oxy]-1,1'-biphenyl-3-yl}methyl)-1,2,4-oxadiazolidine-3,5-dione or a pharmaceutically acceptable salt or ester form thereof; 2-[(4'-{[4-(trifluoromethyl)benzyl]oxy}-1,1'-biphenyl-3-yl)methyl]-1,2,4-oxadiazolidine-3,5-dione or a pharmaceutically acceptable salt or ester form thereof; 2-({4'-[(4-bromobenzyl)oxy]-1,1'-biphenyl-3-yl}methyl)-1,2,4-oxadiazolidine-3,5-dione or a pharmaceutically acceptable salt or ester form thereof; 2-[(4'-{[3,5-bis(trifluoromethyl)benzyl]oxy}-1,1'-biphenyl-3-yl)methyl]-1,2,4-oxadiazolidine-3,5-dione or a pharmaceutically acceptable salt or ester form thereof; 2-({4'-[(3-bromobenzyl)oxy]-1,1'-biphenyl-3-yl}methyl)-1,2,4-oxadiazolidine-3,5-dione or a pharmaceutically acceptable salt or ester form thereof; 2-({3'-[(4-tert-butylbenzyl)oxy]-1,1'-biphenyl-4-yl}methyl)-1,2,4-oxadiazolidine-3,5-dione or a pharmaceutically acceptable salt or ester form thereof; 2-({3'-[(4-bromobenzyl)oxy]-1,1'-biphenyl-4-yl}methyl)-1,2,4-oxadiazolidine-3,5-dione or a pharmaceutically acceptable salt or ester form thereof; and 2-({4'-[(3-bromobenzyl)oxy]-1,1'-biphenyl-4-yl}methyl)-1,2,4-oxadiazolidine-3,5-dione or a pharmaceutically acceptable salt or ester form thereof.

In alternative embodiments of the present invention, substituted oxadiazolidenediones include substituted acetylenic oxadiazolidenediones of the following formula:

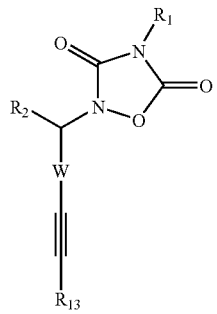

Formula 9 wherein $R_1$, $R_2$, $R_{13}$, W, n, m, and p are defined as above for Formula 1.

Compounds of the present invention also include prodrugs, stereoisomers, or pharmaceutically acceptable salt or ester forms of formula 9.

For use in the present invention, when the substituted oxadiazolidenedione is represented by Formula 9, $R_1$ can be hydrogen or —$(CH_2)_n$COOH and n can be 0, 1, 2, or 3. In such embodiments, $R_2$, $R_{13}$, W, n, m, and p are as defined herein for Formula 9.

In certain embodiments of compounds of formula 9, $R_2$ is $C_3$–$C_6$ cycloalkyl, —$CH_2$—$C_3$–$C_6$ cycloalkyl, pyridinyl, —$CH_2$-pyridinyl, aryl, benzyl or heteroaryl wherein the rings of the cycloalkyl, pyridinyl, aryl, benzyl, and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —CN, —COOH, —COOR wherein R is alkyl, or $CONH_2$. In other embodiments $R_2$ is alkyl or hydrogen. Most preferably $R_2$ is hydrogen. In such embodiments, $R_1$, $R_{13}$, W, n, m, and p are as defined herein for Formula 9.

$R_{13}$ can be hydrogen, $C_1$–$C_8$ alkyl, $C_1$–$C_8$ alkenyl, $C_1$–$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl. In certain embodiments of compounds of formula 9, $R_{13}$ is —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl wherein the rings of the aryl, and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, or —CN. In certain preferred embodiments, $R_{13}$ is aryl, alkyl, —$(CH_2)$—O-aryl where the aryl group is optionally substituted with one or more groups selected from halogen, perfluoroalkyl, alkyl or branched alkyl. Most preferably, $R_{13}$ is phenyl, ethyl, or —$(CH_2)$—O-phenyl where the phenyl group is optionally substituted with one or more groups selected from chlorine, bromine, $CF_3$, butyl or branched butyl. In such embodiments, $R_1$, $R_2$, W, n, m, and p are as defined herein for Formula 9.

W can be aryl or heteroaryl. In preferred embodiments of the present invention, W is phenyl or thiophene. In such embodiments, $R_1$, $R_2$, $R_{13}$, n, m, and p are as defined herein for Formula 9.

In certain embodiments, such substituted acetylenic oxadiazolidinediones include the following compounds:

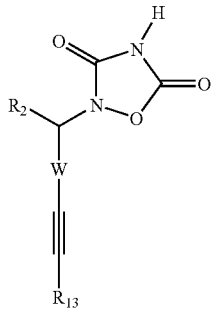

Formula 10 wherein $R_2$, $R_{13}$, W, m, p, and m are as described above for Formula 1.

In certain embodiments of the present invention $R_1$ is hydrogen or —$(CH_2)_n$COOH;

$R_2$ is hydrogen, unsubstituted $C_1$–$C_8$ alkyl, $C_3$–$C_6$ cycloalkyl, —$CH_2$—$C_3$–$C_6$ cycloalkyl, aryl, benzyl, pyridinyl or —$CH_2$-pyridinyl wherein the rings of the cycloalkyl, pyridinyl, aryl and/or benzyl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —CN, —COOH, COOR wherein R is unsubstituted alkyl, —$CONH_2$, —OH, —$NH_2$, or —$NO_2$;

$R_{13}$ is hydrogen, $C_1$–$C_8$ alkyl, $C_1$–$C_8$ alkenyl, $C_1$–$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl wherein the rings of the aryl and heteroaryl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —CN, —OH, —$NH_2$, or —$NO_2$; and W is unsubstituted aryl or unsubstituted heteroaryl.

Exemplary substituted acetylenic oxadiazolidinediones of the present invention include, but are not limited to, 2-[4-(phenylethynyl)benzyl]-1,2,4-oxadiazolidine-3,5-dione or a pharmaceutically acceptable salt or ester form thereof; 2-(4-hex-1-ynylbenzyl)-1,2,4-oxadiazolidine-3,5-dione or a pharmaceutically acceptable salt or ester form thereof; 2-{[4-(phenylethynyl)thien-2-yl]methyl}-1,2,4-oxadiazolidine-3,5-dione or a pharmaceutically acceptable salt or ester form thereof; 2-{[5-(phenylethynyl)thien-2-yl]methyl}-1,2,4-oxadiazolidine-3,5-dione or a pharmaceutically acceptable salt or ester form thereof; 2-[3-(phenylethynyl)benzyl]-1,2,4-oxadiazolidine-3,5-dione or a pharmaceutically acceptable salt or ester form thereof; 2-(4-{3-[3,5-bis(trifluoromethyl)phenoxy]prop-1-ynyl}benzyl)-1,2,4-oxadiazolidine-3,5-dione or a pharmaceutically acceptable salt or ester form thereof; 2-{4-[3-(3,5-dichlorophenoxy)prop-1-ynyl]benzyl}-1,2,4-oxadiazolidine-3,5-dione or a pharmaceutically acceptable salt or ester form thereof; 2-{4-[3-(3-chlorophenoxy)prop-1-ynyl]benzyl}-1,2,4-oxadiazolidine-3,5-dione or a pharmaceutically acceptable salt or ester form thereof; 2-{4-[3-(4-isobutylphenoxy)prop-1-ynyl]benzyl}-1,2,4-oxadiazolidine-3,5-dione or a pharmaceutically acceptable salt or ester form thereof; 2-{3-[3-(4-tert-butylphenoxy)prop-1-ynyl]benzyl}-1,2,4-oxadiazolidine-3,5-dione or a pharmaceutically acceptable salt or ester form thereof; 2-{3-[3-(4-bromophenoxy)prop-1-ynyl]benzyl}-1,2,4-oxadiazolidine-3,5-dione or a pharmaceutically acceptable salt or ester form thereof; 2-(3-{3-[3,5-bis(trifluoromethyl)phenoxy]prop-1-ynyl}benzyl)-1,2,4-oxadiazolidine-3,5-dione or a pharmaceutically acceptable salt or ester form thereof; 2-{3-[3-(3,5-dichlorophenoxy)prop-1-ynyl]benzyl}-1,2,4-oxadiazolidine-3,5-dione or a pharmaceutically acceptable salt or ester form thereof; 2-{3-[3-(3-chlorophenoxy)prop-1-ynyl]benzyl}-1,2,4-oxadiazolidine-3,5-dione or a pharmaceutically acceptable salt or ester form thereof; and 2-{3-[3-(4-isobutylphenoxy)prop-1-ynyl]benzyl}-1,2,4-oxadiazolidine-3,5-dione a pharmaceutically acceptable salt or ester form thereof.

In alternative embodiments of the present invention, substituted oxadiazolidinediones include substituted bisbenzyloxybenzyl oxadiazolidinediones of the following formula:

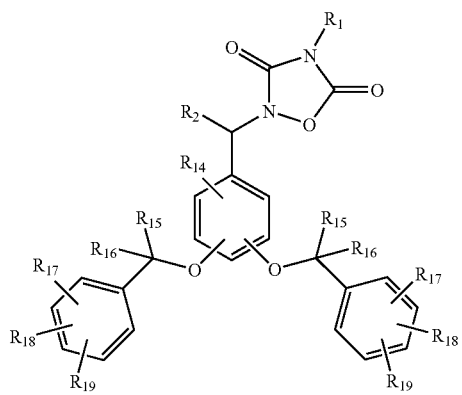

Formula 11

Wherein $R_1$, $R_2$, $R_{14}$, $R_{15}$, $R_{16}$, $R_{17}$, $R_{18}$, $R_{19}$, n and q are as defined above for Formula 1.

Compounds of the present invention also include prodrugs, stereoisomers, or pharmaceutically acceptable salts or ester forms of formula 11.

For use in the present invention, when the substituted oxadiazolidenedione is represented by Formula 11, $R_1$ can be hydrogen or —$(CH_2)_n$COOH and n can be 0, 1, 2, or 3. In such embodiments, $R_2$, $R_{14}$, $R_{15}$, $R_{16}$, $R_{17}$, $R_{18}$, $R_{19}$, n and q are as defined herein for Formula 11.

In certain embodiments of compounds of formula 11, $R_2$ is $C_3$–$C_6$ cycloalkyl, —$CH_2$—$C_3$–$C_6$ cycloalkyl, pyridinyl, —$CH_2$-pyridinyl, aryl, benzyl or heteroaryl wherein the rings of the cycloalkyl, pyridinyl, aryl, benzyl, and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —CN, —COOH, —COOR wherein R is alkyl, or $CONH_2$. In other embodiments, $R_2$ is alkyl or hydrogen. Most preferably $R_2$ is hydrogen. In such embodiments, $R_1$, $R_{14}$, $R_{15}$, $R_{16}$, $R_{17}$, $R_{18}$, $R_{19}$, n and q are as defined herein for Formula 11.

In certain embodiments of compounds of formula 11, $R_{14}$ is —$O(CH_2)_q$-aryl, —$O(CH_2)_q$-heteroaryl, aryl, or heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In preferred embodiments, $R_{14}$ is hydrogen, alkyl, alkoxy, or halogen. Most preferably, $R_{14}$ is hydrogen or methoxy. In such embodiments, $R_1$, $R_2$, $R_{15}$, $R_{16}$, $R_{17}$, $R_{18}$, $R_{19}$, n and q are as defined herein for Formula 11.

$R_{15}$ and $R_{16}$ can be hydrogen, $C_1$–$C_8$ alkyl, $C_3$–$C_6$ cycloalkyl, —$CH_2$—$C_3$–$C_6$ cycloalkyl, aryl, benzyl, heteroaryl or —$CH_2$-heteroaryl. In certain embodiments of compounds of formula 11, $R_{15}$ is $C_3$–$C_6$ cycloalkyl, —$CH_2$—$C_3$–$C_6$ cycloalkyl, pyridinyl, —$CH_2$-pyridinyl, aryl, benzyl or heteroaryl wherein the rings of the cycloalkyl, pyridinyl, aryl, benzyl, and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —CN, —COOH, —COOR wherein R is alkyl, or $CONH_2$. In other embodiments, $R_{15}$ is alkyl or hydrogen. Most preferably $R_{15}$ is hydrogen. In such embodiments, $R_1$, $R_2$, $R_{14}$, $R_{17}$, $R_{18}$, $R_{19}$, n and q are as defined herein for Formula 11.

In certain embodiments of compounds of formula 11, $R_{16}$ is $C_3$–$C_6$ cycloalkyl, —$CH_2$—$C_3$–$C_6$ cycloalkyl, pyridinyl, —$CH_2$-pyridinyl, aryl, benzyl or heteroaryl wherein the rings of the cycloalkyl, pyridinyl, aryl, benzyl, and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —CN, —COOH, —COOR wherein R is alkyl, or $CONH_2$. In other embodiments, $R_{15}$ is alkyl or hydrogen. Most preferably $R_{16}$ is hydrogen. In such embodiments, $R_1$, $R_2$, $R_{14}$, $R_{15}$, $R_{17}$, $R_{18}$, $R_{19}$, n and q are as defined herein for Formula 11.

In certain embodiments of compounds of formula 11, $R_{17}$ is —$O(CH_2)_q$-aryl, —$O(CH_2)_q$-heteroaryl, aryl, or heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain embodiments, $R_{17}$ is hydrogen or alkyl. Most preferably, $R_{17}$ is hydrogen. In such embodiments, $R_1$, $R_2$, $R_{14}$, $R_{15}$, $R_{16}$, $R_{18}$, $R_{19}$, n and q are as defined herein for Formula 11.

In certain embodiments of compounds of formula 11, $R_{18}$ is —$O(CH_2)_q$-aryl, —$O(CH_2)_q$-heteroaryl, aryl, or heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain embodiments, $R_{18}$ is hydrogen, alkyl, perfluoroalkyl, or halogen. Most preferably, $R_{18}$ is hydrogen. In such embodiments, $R_1$, $R_2$, $R_{14}$, $R_{15}$, $R_{16}$, $R_{17}$, $R_{19}$, n and q are as defined herein for Formula 11.

In certain embodiments of compounds of formula 11, $R_{19}$ is —$O(CH_2)_q$-aryl, —$O(CH_2)_q$-heteroaryl, aryl, or heteroaryl wherein the rings of the aryl and heteroaryl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$. In certain embodiments, $R_{19}$ is hydrogen, alkyl, perfluoroalkyl, or halogen. Most preferably, $R_{19}$ is chorine, $CF_3$, or bromine. In such embodiments, $R_1$, $R_2$, $R_{14}$, $R_{15}$, $R_{16}$, $R_{17}$, $R_{18}$, n and q are as defined herein for Formula 11.

In certain preferred embodiments, such substituted bisbenzyloxybenzyl oxadiazolidinediones include the following compounds:

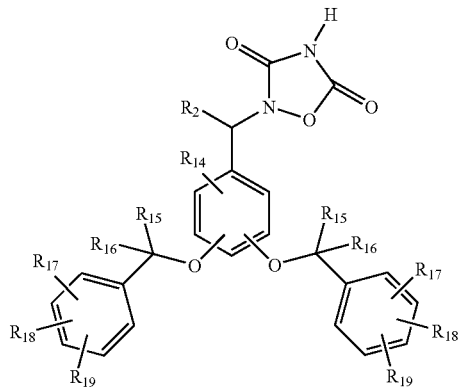

Formula 12 wherein $R_1$, $R_2$, $R_{14}$, $R_{15}$, $R_{16}$, $R_{17}$, $R_{18}$, $R_{19}$, n and q are as defined above for Formula 1.

In certain embodiments of the present invention, $R_1$ is hydrogen or —$(CH_2)_n$COOH;

$R_2$ is hydrogen, $C_1$–$C_8$ alkyl, $C_3$–$C_6$ cycloalkyl, —$CH_2$—$C_3$–$C_6$ cycloalkyl, aryl, benzyl, pyridinyl or —$CH_2$-pyridinyl wherein the rings of the cycloalkyl, pyridinyl, aryl and/or benzyl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —$NH_2$, or —$NO_2$;

$R_{14}$, $R_{17}$, $R_{18}$ and $R_{19}$ are, independently, hydrogen, halogen, unsubstituted $C_1$–$C_6$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —$NH_2$, —$NO_2$, —$O(CH_2)_q$-aryl, —$O(CH_2)_q$-heteroaryl, aryl, or heteroaryl wherein the rings of the aryl and heteroaryl groups are optionally substituted by 1 to 3 groups selected from halogen, unsubstituted $C_1$–$C_3$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —$NH_2$, or —$NO_2$;

$R_{15}$ and $R_{16}$ are, independently, hydrogen, unsubstituted $C_1$–$C_8$ alkyl, $C_3$–$C_6$ cycloalkyl, —$CH_2$—$C_3$–$C_6$ cycloalkyl, aryl, benzyl, pyridinyl or —$CH_2$-pyridinyl wherein the rings of the cycloalkyl, pyridinyl, aryl and/or benzyl groups are optionally substituted by 1 to 3 groups selected from halogen, unsubstituted $C_{1-C3}$ alkyl, unsubstituted $C_1$–$C_3$ perfluoroalkyl, unsubstituted —O—$C_1$–$C_3$ perfluoroalkyl, unsubstituted $C_1$–$C_3$ alkoxy, —OH, —$NH_2$, or —$NO_2$.

Exemplary substituted bisbenzyloxybenzyl oxadiazolidinediones of the present invention include, but are not limited to, 2-{(3,5-bis[(3-chlorobenzyl)oxy]benzyl}-1,2,4-oxadiazolidine-3,5-dione or a pharmaceutically acceptable salt or ester form thereof; 2-(3,5-bis{[4-(trifluoromethyl) benzyl]oxy}benzyl)-1,2,4-oxadiazolidine-3,5-dione or a pharmaceutically acceptable salt or ester form thereof; 2-{3, 5-bis[(3-methylbenzyl)oxy]benzyl}-1,2,4-oxadiazolidine-3, 5-dione or a pharmaceutically acceptable salt or ester form thereof; 2-{3,5-bis[(3-bromobenzyl)oxy]benzyl}-1,2,4-oxadiazolidine-3,5-dione or a pharmaceutically acceptable salt or ester form thereof; 2-{3,5-bis[(2-bromobenzyl)oxy]benzyl}-1,2,4-oxadiazolidine-3,5-dione or a pharmaceutically acceptable salt or ester form thereof; 2-(3-methoxy-4,5-bis{ [4-(trifluoromethyl)benzyl]oxy}benzyl)-1,2,4-oxadiazolidine-3,5-dione or a pharmaceutically acceptable salt or ester form thereof; 2-{3-methoxy-4,5-bis[(3-methylbenzyl)oxy} benzyl}-1,2,4-oxadiazolidine-3,5-dione or a pharmaceutically acceptable salt or ester form thereof; 2-{3,4-bis[(3-chlorobenzyl)oxy]-5-methoxybenzyl}-1,2,4-oxadiazolidine-3,5-dione or a pharmaceutically acceptable salt or ester form thereof; 2-{3,4-bis[(3-bromobenzyl)oxy]-5-methoxybenzyl}-1,2,4-oxadiazolidine-3,5-dione or a pharmaceutically acceptable salt or ester form thereof; 2-{(3,4-bis[(2-bromobenzyl)oxy]-5-methoxybenzyl}-1,2,4-oxadiazolidine-3,5-dione or a pharmaceutically acceptable salt or ester form thereof; 2-(2,3-bis {[4-(trifluoromethyl)benzyl]oxy}benzyl)-1,2,4-oxadiazolidine-3,5-dione or a pharmaceutically acceptable salt or ester form thereof; 2-{2,3-bis[(3-methylbenzyl)oxy]benzyl}-1,2,4-oxadiazolidine-3,5-dione or a pharmaceutically acceptable salt or ester form thereof; 2-{2,3-bis[(3-chlorobenzyl)oxy]benzyl}-1,2,4-oxadiazolidine-3,5-dione or a pharmaceutically acceptable salt or ester form thereof; 2-{2,3-bis[(3-bromobenzyl)oxy]benzyl}-1,2,4-oxadiazolidine-3,5-dione or a pharmaceutically acceptable salt or ester form thereof; 2-{2,3-bis[(2-bromobenzyl)oxy]benzyl}-1,2,4-oxadiazolidine-3,5-dione or a pharmaceutically acceptable salt or ester form thereof; 2-(3,4-bis{[4-(trifluoromethyl)benzyl]oxy}benzyl)-1,2,4-oxadiazolidine-3,5-dione or a pharmaceutically acceptable salt or ester form thereof; 2-{3,4-bis[(3-methylbenzyl)oxy]benzyl}-1,2,4-oxadiazolidine-3,5-dione or a pharmaceutically acceptable salt or ester form thereof; 2-{3,4-bis[(3-chlorobenzyl)oxy]benzyl}-1,2,4-oxadiazolidine-3,5-dione or a pharmaceutically acceptable salt or ester form thereof; 2-{3,4bis[(3-bromobenzyl)oxy]benzyl}-1,2,4-oxadiazolidine-3,5-dione or a pharmaceutically acceptable salt or ester form thereof; and 2-{3,4-bis[(2-bromobenzyl)oxy]benzyl}-1,2,4-oxadiazolidine-3,5-dione or a pharmaceutically acceptable salt or ester form thereof.

The present invention also provides compositions comprising substituted oxadiazolidinediones, including those compounds of formulas 1–12 or a stereoisomer or pharmaceutically acceptable salt thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more substituted oxadiazolidinediones.

Certain of the compounds of formulas 1–12 contain stereogenic carbon atoms or other chiral elements and thus give rise to stereoisomers, including enantiomers and diastereomers. The present invention includes all of the stereoisomers of formulas 1–12, as well as mixtures of the stereoisomers. Throughout this application, the name of the product, where the absolute configuration of an asymmetric center is not indicated, is intended to embrace the individual stereoisomers as well as mixtures of stereoisomers. When it is necessary to distinguish the enantiomers from one another and from the racemate, the sign of the optical rotation [(+), (−) and (±)] is utilized. Furthermore, throughout this application, the designations R* and S* are used to indicate relative stereochemistry, employing the Chemical Abstracts convention which automatically assigns R* to the lowest numbered asymmetric center.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium, potassium, lithium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms can be prepared using the acidic compound(s) of Formulas 1–12 and procedures known in the art.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer substituted oxadiazolidinediones, including those represented by formulas 1–12, to a subject suffering from any of the diseases associated with increased PAI-1 activity or expression, e.g., diabetes or cardiovascular disease, in order to effect treatment for that disease.

In one exemplary embodiment, substituted oxadiazolidinediones are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using substituted oxadiazolidinediones of the present invention. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins; diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; respiratory diseases, such as asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and II diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis of Substituted Oxadiazolidinediones

Compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps, which in themselves are well known in the art. $R_4$ is defined as above.

In certain embodiments of the present invention, representative substituted indolylmethyl oxadiazolidinediones can be prepared using scheme 1:

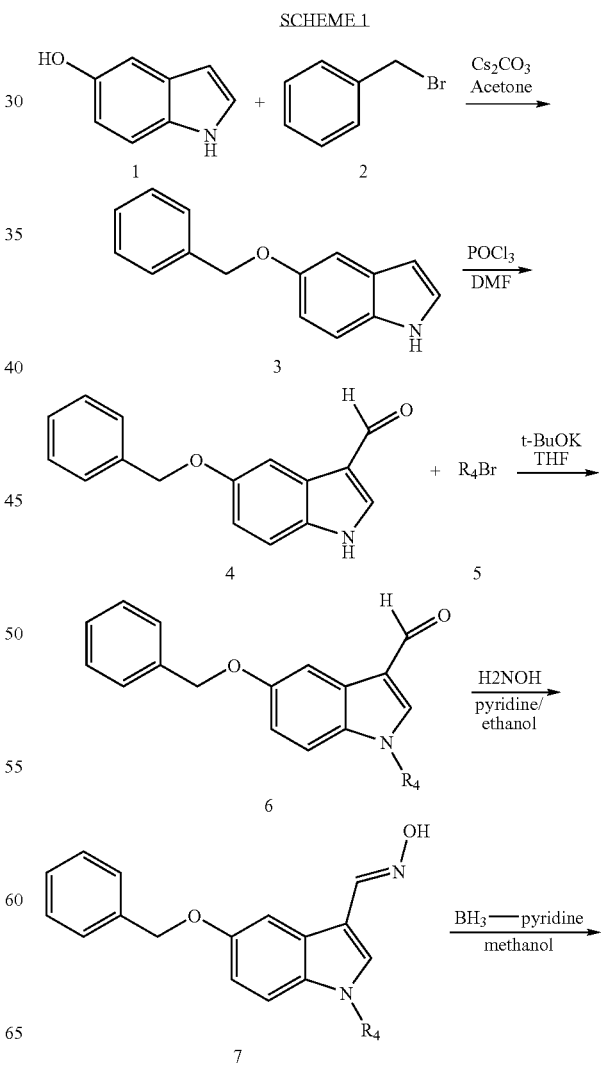

-continued

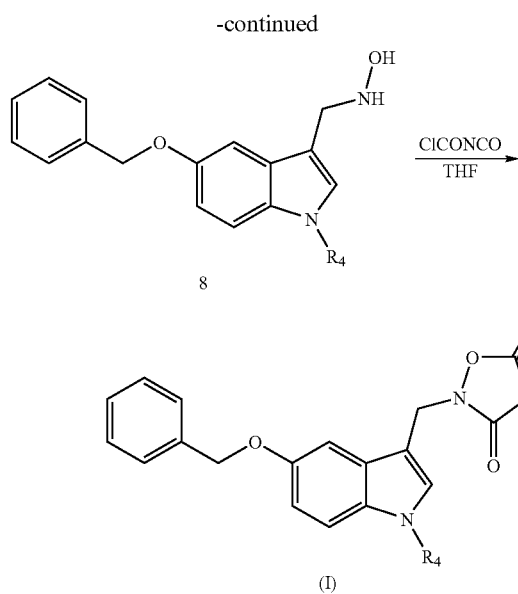

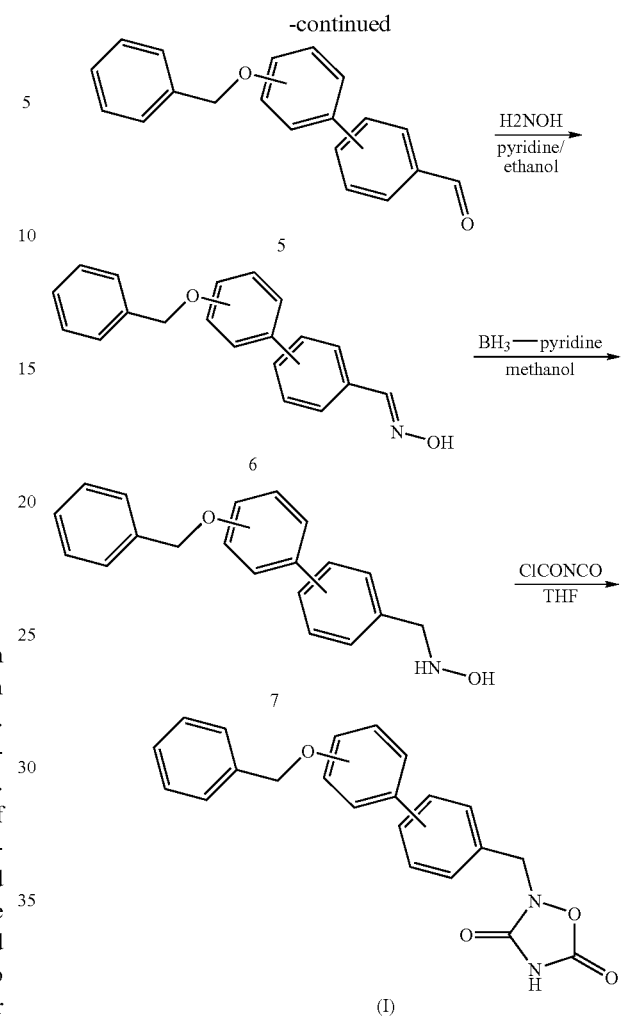

5-Hydroxyindole was reacted with benzyl bromide 2 in the presence of a base like cesium carbonate or potassium carbonate in a solvent like acetone to give benzyl ether 3. Benzyl ether 3 was formylated using phosphorus oxychloride in a solvent like dimethylformamide to give aldehyde 4. Aldehyde 4 was reacted with bromide 5 in the presence of a base like potassium t-butoxide in a solvent like tetrahydrofuran to give compound 6. The aldehyde 6 was reacted with hydroxylamine hydrochloride in a mixture of pyridine and ethanol to yield indole oxime 7. Oxime 7 was reduced using borane pyridine complex in a solvent like methanol to yield hydroxylamine 8. The hydroxylamine 8 was further cyclized using N-(chlorocarbonyl) isocyanate in a solvent like tetrahydrofuran to yield the indolylmethyl oxadiazolidinedione (I).

Representative substituted biphenylmethyl oxadiazolidinediones can be prepared using scheme 2.

SCHEME 2

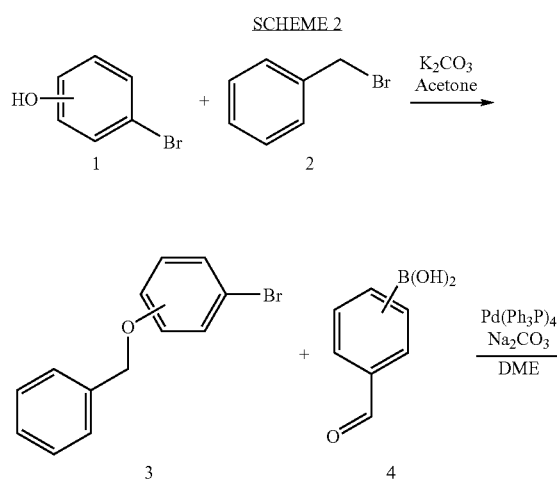

Bromophenol 1 was reacted with benzyl bromide 2 in the presence of a base potassium carbonate in a solvent like acetone to give benzyl ether 3. Benzyl ether 3 was reacted with boronic acid 4 using tetrakis(triphenylphosphine)palladium(0) and sodium carbonate in a solvent like (DME) to give aldehyde 5. The aldehyde 5 was reacted with hydroxylamine hydrochloride in a mixture of pyridine and ethanol to yield biphenyl oxime 6. Oxime 6 was reduced using borane pyridine complex in a solvent like methanol to yield hydroxylamine 7. The hydroxylamine 7 was further cyclized using N-(chlorocarbonyl) isocyanate in a solvent like tetrahydrofuran to yield the biphenylmethyl oxadiazolidinedione (I).

Representative substituted acetylenic oxadiazolidinediones can be prepared using scheme 3.

SCHEME 3

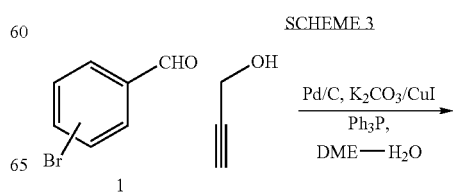

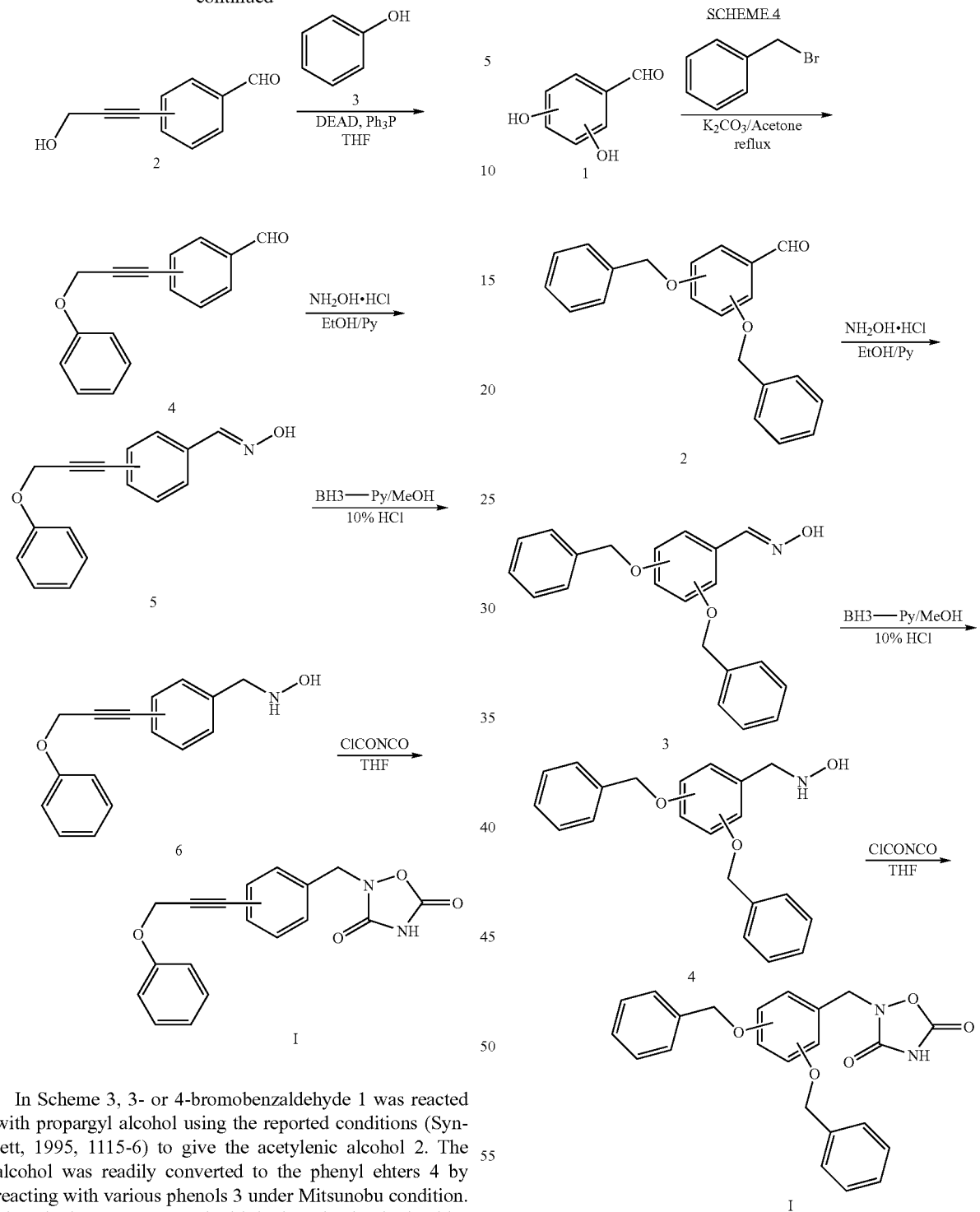

In Scheme 3, 3- or 4-bromobenzaldehyde 1 was reacted with propargyl alcohol using the reported conditions (Synlett, 1995, 1115-6) to give the acetylenic alcohol 2. The alcohol was readily converted to the phenyl ehters 4 by reacting with various phenols 3 under Mitsunobu condition. Phenyl ether 4 was reacted with hydroxylamine hydrochloride in a mixture of pyridine and ethanol to yield oxime 5. Oxime 5 was reduced using borane pyridine complex in a solvent like methanol and 10% HCl to yield hydroxylamine 6. The hydroxylamine 6 was further cyclized using N-(chlorocarbonyl) isocyanate in a solvent like tetrahydrofuran to yield the oxadiazolidinedione (I).

Representative substituted bisbenzyloxybenzyl oxadiazolidinediones can be prepared using scheme 4.

In Scheme 4 dihydroxybenzaldehyde 1 was reacted with benzyl bromide in the presence of a base like potassium carbonate in a solvent like acetone to give benzyl ether 2. Benzyl ether 2 was reacted with hydroxylamine hydrochloride in a mixture of pyridine and ethanol to yield oxime 3. Oxime 3 was reduced using borane pyridine complex in a solvent like methanol and 10% HCl to yield hydroxylamine 4. The hydroxylamine 4 was further cyclized using N-(chlorocarbonyl) isocyanate in a solvent like tetrahydrofuran to yield the bisbenzyloxybenzyl oxadiazolidinedione (I).

D. Substituted Oxadiazolidinediones as Pharmaceutical Compositions

The present invention provides substituted oxadiazolidinediones as pharmaceuticals. In a preferred embodiment, the substituted oxadiazolidinediones are formulated as pharmaceuticals to treat diseases associated with increased PAI-1 activity, e.g., by inhibiting PAI-1 activity in a subject.

In general, substituted oxadiazolidinediones can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, substituted oxadiazolidinediones suitable for use in the practice of this invention will be administered either singly or in combination with at least one other compound of this invention. Substituted oxadiazolidinediones suitable for use in the practice of the present invention can also be administered with at least one other conventional therapeutic agent for the disease being treated.

Aqueous suspensions of the invention can contain a substituted oxadiazolidinedione in admixture with excipients suitable for the manufacture of aqueous suspensions. Such excipients can include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a substituted oxadiazolidinedione in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93–102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of substituted oxadiazolidinediones in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3- butanediol. The formulations of commends can be presented in unit-dose or multi-dose sealed containers, such as ampules and vials.

Injection solutions and suspensions can be prepared from sterile powders, granules, and tablets of the kind previously described.

Substituted oxadiazolidinediones suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 10% w of the substituted oxadiazolidinedione, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethyl-cellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The substituted oxadiazolidinediones of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187–1193, 1995; Tjwa, Ann. Allergy Asthma Immunol. 75:107–111, 1995).

The substituted oxadiazolidinediones of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug-containing microspheres, which slowly release subcutaneously (see Rao, J. Biomater. Sci. Polym. Ed. 7:623–645, 1995; as biodegradable and injectable gel formulations (see, e.g., Gao, Pharm. Res. 12:857–863, 1995); or, as microspheres for oral administration (see, e.g., Eyles, J. Pharm. Pharmacol. 49:669–674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293–306, 1996; Chonn, Curr. Opin. Biotechnol. 6:698–708, 1995; Ostro, Am. J. Hosp. Pharm. 46:1576–1587, 1989).

In other cases, the preferred preparation can be a lyophilized powder which may contain, for example, any or all of the following: 1 mM–50 mM histidine, 0.1%–2% sucrose, 2%–7% mannitol, at a pH range of 4.5 to 5.5, that is combined with buffer prior to use.

A pharmaceutical composition of the invention can optionally contain, in addition to a substituted oxadiazolidinedione, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration

E. Determining Dosage Regimens for Substitued Oxadiazolidinediones

The present invention provides methods of inhibiting PAI-1 activity in a subject for the treatment of diseases and conditions associated with increased PAI-1 activity using substituted oxadiazolidinediones.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1–3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of, for example, from about one gram to about fifteen grams or more, for single or multiple daily administration, according to the particular need of the patient. By initiating the treatment regimen with a minimal daily dose of about one gram, the blood levels of PAI-1 and the patients symptomatic relief analysis can be used to determine whether a larger or smaller dose is indicated. Effective administration of the compounds of this invention can be given at an oral dose of, for example, from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day.

In certain embodiments, the present invention is directed to prodrugs of compounds of formulas 1–12. The term "prodrug," as used herein, means a compound that is convertible in vivo by metabolic means (e.g. by hydrolysis) to a compound of formulas 1–12. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., *Journal of Drug Delivery Reviews,* 8:1–38(1992), Bundgaard, *J. of Pharmaceutical Sciences,* 77:285 et seq. (1988); and Higuchi and Stella (eds.) Prodrugs as Novel Drug Delivery Systems, American Chemical Society (1975).

F. Kits

After a pharmaceutical comprising a substituted oxadiazolidinedione has been formulated in a suitable carrier, it can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. Alternatively, a single pharmaceutical comprising a substituted oxadiazolidinedione and at least one other therapeutic agent useful in the treatment of a PAI-1 related disorder can be placed in an appropriate container and labeled for treatment. For administration of pharmaceuticals comprising substituted oxadiazolidinediones and of pharmaceuticals comprising, in a single pharmaceutical, substituted oxadiazolidinediones and at least one other therapeutic agent useful in the treatment of a PAI-1 related disorder, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

The syntheses of compounds 1–90 are described in examples 1–90 respectively.

Example 1

Synthesis of 2-({1-benzyl-5-[(4-tert-butylbenzyl) oxy]-1H-indol-3-yl}methyl)-1,2,4-oxadiazolidine-3, 5-dione Step 1: To a solution of 5-hydroxyindole (66.3 mg, 0.5 mmol) in acetone was added cesium carbonate (651.6 mg, 2 mmol) and 4-t-butylbenzyl bromide (0.092 ml, 0.5 mmol). The reaction mixture was shaken at 60° C. overnight. The mixture was filtered and washed. The solvent was evaporated in vacuo.

Step 2: To a solution of crude benzyl ether (0.5 mmol) obtained from step 1 in DMF (0.2 ml) at 6° C. was added a $POCl_3$/DMF solution (0.2 ml) in a 1.1:4 molar ratio. The reaction mixture was shaken and allowed to warm to 12° C. for 1 hour. Another 0.1 ml of $POCl_3$/DMF solution was added and the reaction mixture was shaken for one more hour. The mixture was carefully quenched with water and the solid filtered. The solid was dissolved in 1:1 MeOH/THF (5 ml). To this solution was added concentrated HCl (0.2 ml) and the reaction was shaken at room temperature for 1 hour. The mixture was neutralized with 4N NaOH and the solvents concentrated. The crude residue was partitioned between EtOAc and water. The organic layer was dried with $MgSO_4$ and concentrated in vacuo.

Step 3: To a solution of aldehyde (0.5 mmol) obtained from step 2 in THF (0.5 ml) was added 1M solution of t-BuOKin THF (0.75 ml, 0.75 mmol) and benzylbromide (0.089 ml, 0.75 mmol). The reaction was shaken at room temperature overnight. The solvent was evaporated in vacuo.

Step 4: To a solution of aldehyde (0.5 mmol) obtained from step 3 dissolved in pyridine (0.5 ml) and EtOH (4.5 ml) was added hydroxylamine hydrochloride (17.4 mg, 0.25 mmol). The reaction was heated to 60 C for 2 hours. The solvent was evaporated in vacuo.

Step 5: To a solution of oxime (0.5 mmol) obtained from step 4 dissolved in MeOH (1 ml) was added 8M solution of borane/pyridine complex (0.313 ml, 2.5 mmol) and 10% HCl (0.5 ml). The reaction was shaken for 3 hours. The solvent was evaporated in vacuo. The residue was partitioned between EtOAc and water. The organic layer was dried with $MgSO_4$ and concentrated in vacuo.

Step 6: To a solution of hydroxylamine (0.5 mmol) obtained from step 5 in anhydrous THF (2 ml) was added N-(chlorocarbonyl) isocyanate (0.527 g, 5 mmol). The reaction was shaken at room temperature for 3 hours. To the reaction was added 10% HCl. The solvent was evaporated in vacuo. The crude product was purified by RP-HPLC to give example 303. $^1$H NMR (DMSO $d_6$, 300 MHz) δ 1.28 (s, 9H), 4.90 (s, 2H), 5.01 (s, 2H), 5.38 (s, 2H), 6.83 (dd, J=8.9, 2.3 Hz, 1H), 7.14 (d, J=6.5 Hz, 2H), 7.22–7.37 (m, 6H), 7.39 (s, 3H), 7.54 (s, 1H), 12.29 (s, 1H); MS: (M−H) 482.1.

Example 2

Synthesis of 2-({1-allyl-5-[(4-tert-butylbenzyl)oxy]-1H-indol-3-yl}methyl)-1,2,4-oxadiazolidine-3,5-dione 2-({1-allyl-5-[(4-tert-butylbenzyl)oxy]-1H-indol-3-yl}methyl)-1,2,4-oxadiazolidine-3,5-dione was synthesized using the procedure outlined for example 1 using 4-t-butylbenzyl bromide and the resulting ether was further alkylated using allyl bromide.

Example 3

Synthesis of 2-({5-[(4-tert-butylbenzyl)oxy]-1-ethyl-1H-indol-3-yl}methyl)-1,2,4-oxadiazolidine-3, 5-dione 2-({5-[(4-tert-butylbenzyl)oxy]-1-ethyl-1H-indol-3-yl}methyl)-1,2,4-oxadiazolidine-3,5-dione was synthesized using the procedure outlined for example 1 using 4-t-butylbenzyl bromide and the resulting ether was further alkylated using ethyl bromide.

Example 4

Synthesis of 2-[(1-allyl-5-{[4-(trifluoromethyl)benzyl]oxy}-1H-indol-3-yl)methyl]-1,2,4-oxadiazolidine-3,5-dione 2-[(1-allyl-5-{[4-(trifluoromethyl)benzyl]oxy}-1H-indol-3-yl)methyl]-1,2,4-oxadiazolidine-3,5-dione was synthesized using the procedure outlined for example 1 using 4-(trifluoromethyl)benzyl bromide and the resulting ether was further alkylated using allyl bromide.

Example 5

Synthesis of 2-[(1-allyl-5-{[3,5-bis(trifluoromethyl) benzyl]oxy}-1H-indol-3-yl)methyl]-1,2,4-oxadiazolidine-3,5-dione 2-[(1-allyl-5-{[3,5-bis(trifluoromethyl)benzyl]oxy}-1H-indol-3-yl)methyl]-1,2,4-oxadiazolidine-3,5-dione was synthesized using the procedure outlined for example 1 using 3,5-bis(trifluoromethyl)benzyl bromide and the resulting ether was further alkylated using allyl bromide.

Example 6

Synthesis of 2-[(5-{[3,5-bis(trifluoromethyl)benzyl] oxy}-1-ethyl-1H-indol-3-yl)methyl]-1,2,4-oxadiazolidine-3,5-dione 2-[(5-{[3,5-bis(trifluoromethyl)benzyl]oxy}-1-ethyl-1H-indol-3-yl)methyl]-1,2,4-oxadiazolidine-3,5-dione was synthesized using the procedure outlined for example 1 using 3,5bis(trifluoromethyl)benzyl bromide and the resulting ether was further alkylated using ethyl bromide.

Example 7

Synthesis of 2-[(1-benzyl-5-{[3,5-bis(trifluoromethyl)benzyl]oxy}-1H-indol-3-yl)methyl]-1,2,4-oxadiazolidine-3,5-dione 2-[(1-benzyl-5-{[3,5-bis(trifluoromethyl)benzyl]oxy}-1H-indol-3-yl)methyl]-1,2,4-oxadiazolidine-3,5-dione was synthesized using the procedure outlined for example 1 using 3,5-bis(trifluoromethyl)benzyl bromide and the resulting ether was further alkylated using benzyl bromide.

Example 8

Synthesis of 2-({1-benzyl-5-[(3-bromobenzyl)oxy]-1H-indol-3-yl}methyl)-1,2,4-oxadiazolidine-3,5-dione 2-({1-benzyl-5-[(3-bromobenzyl)oxy]-1H-indol-3-yl}methyl)-1,2,4-oxadiazolidine-3,5-dione was synthesized using the procedure outlined for example 1 using 3-bromobenzyl bromide and the resulting ether was further alkylated using benzyl bromide.

Example 9

Synthesis of 2-({1-benzyl-5-[(3-chlorobenzyl)oxy]-1H-indol-3-yl}methyl)-1,2,4-oxadiazolidine-3,5-dione 2-({1-benzyl-5-[(3-chlorobenzyl)oxy]-1H-indol-3-yl}methyl)-1,2,4-oxadiazolidine-3,5-dione was synthesized using the procedure outlined for example 1 using 3-chlorobenzyl bromide and the resulting ether was further alkylated using benzyl bromide.

Example 10

Synthesis of 2-[(1-benzyl-5-{[3-(trifluoromethyl)benzyl]oxy}-1H-indol-3-yl)methyl]-1,2,4-oxadiazolidine-3,5-dione 2-[(1-benzyl-5-{[3-(trifluoromethyl)benzyl]oxy}-1H-indol-3-yl)methyl]-1,2,4-oxadiazolidine-3,5-dione was synthesized using the procedure outlined for example 1 using 3-(trifluoromethyl)benzyl bromide and the resulting ether was further alkylated using benzyl bromide.

Example 11

Synthesis of 2-({1-benzyl-5-[(3-methylbenzyl)oxy]-1H-indol-3-yl}methyl)-1,2,4-oxadiazolidine-3,5-dione 2-({1-benzyl-5-[(3-methylbenzyl)oxy]-1H-indol-3-yl}methyl)-1,2,4-oxadiazolidine-3,5-dione was synthesized using the procedure outlined for example 1 using 3-methylbenzyl bromide and the resulting ether was further alkylated using benzyl bromide.

Example 12

Synthesis of 2-[(1-(2-propynyl)-5-{[4-(trifluoromethyl)benzyl]oxy}-1H-indol-3-yl)methyl]-1,2,4-oxadiazolidine-3,5-dione 2-[(1-(2-propynyl)-5-{[4-(trifluoromethyl)benzyl]oxy}-1H-indol-3-yl)methyl]-1,2,4-oxadiazolidine-3,5-dione was synthesized using the procedure outlined for example 1 using 4-(trifluoromethyl)benzyl bromide and the resulting ether was further alkylated using propargyl bromide.

Example 13

Synthesis of 2-[(1-benzyl-5-{[4-(trifluoromethyl)benzyl]oxy}-1H-indol-3-yl)methyl]-1,2,4-oxadiazolidine-3,5-dione 2-[(1-benzyl-5-{[4-(trifluoromethyl)benzyl]oxy}-1H-indol-3-yl)methyl]-1,2,4-oxadiazolidine-3,5-dione was synthesized using the procedure outlined for example 1 using 4-(trifluoromethyl)benzyl bromide and the resulting ether was further alkylated using benzyl bromide.

Example 14

Synthesis of 2-({1-benzyl-5-[(4-bromobenzyl)oxy]-1H-indol-3-yl}methyl)-1,2,4-oxadiazolidine-3,5-dione 2-({1-benzyl-5-[(4-bromobenzyl)oxy]-1H-indol-3-yl}methyl)-1,2,4-oxadiazolidine-3,5-dione was synthesized using the procedure outlined for example 1 using 4-bromobenzyl bromide and the resulting ether was further alkylated using benzyl bromide.

Examples 15

Synthesis of 2-{[5-{[3,5-bis(trifluoromethyl)benzyl]oxy}-1-(2-propynyl)-1H-indol-3-yl]methyl}-1,2,4-oxadiazolidine-3,5-dione 2-{[5-{[3,5-bis(trifluoromethyl)benzyl]oxy}-1-(2-propynyl)-1H-indol-3-yl]methyl}-1,2,4-oxadiazolidine-3,5-dione was synthesized using the procedure outlined for example 1 using 3,5-bis(trifluoromethyl)benzyl bromide and the resulting ether was further alkylated using propargyl bromide.

Example 16

Synthesis of 2-[(5-{[3,5-bis(trifluoromethyl)benzyl]oxy}-1-methyl-1H-indol-3-yl)methyl]-1,2,4-oxadiazolidine-3,5-dione 2-[(5-{[3,5-bis(trifluoromethyl)benzyl]oxy}-1-methyl-1H-indol-3-yl)methyl]-1,2,4-oxadiazolidine-3,5-dione was synthesized using the procedure outlined for example 1 using 3,5-bis(trifluoromethyl)benzyl bromide and the resulting ether was further alkylated using methyl bromide.

Example 17

Synthesis of 2-{[5-[(2-chlorobenzyl)oxy]-1-(2-propynyl)-1H-indol-3-yl]methyl}-1,2,4-oxadiazolidine-3,5-dione 2-{[5-[(2-chlorobenzyl)oxy]-1-(2-propynyl)-1H-indol-3-yl]methyl}-1,2,4-oxadiazolidine-3,5-dione was synthesized using the procedure outlined for example 1 using 2-chlorobenzyl bromide and the resulting ether was further alkylated using propargyl bromide.

Example 18

Synthesis of 2-{[5-[(3,4-dichlorobenzyl)oxy]-1-(2-propynyl)-1H-indol-3-yl]methyl}-1,2,4-oxadiazolidine-3,5-dione 2-{[5-[(3,4-dichlorobenzyl)oxy]-1-(2-propynyl)-1H-indol-3-yl]methyl}-1,2,4-oxadiazolidine-3,5-dione was synthesized using the procedure outlined for example 1 using 3,4-dichlorobenzyl bromide and the resulting ether was further alkylated using propargyl bromide.

Example 19

Synthesis of 2-({1-benzyl-5-[(3,4-dichlorobenzyl)oxy]-1H-indol-3-yl}methyl)-1,2,4-oxadiazolidine-3,5-dione 2-({1-benzyl-5-[(3,4-dichlorobenzyl)oxy]-1H-indol-3-yl}methyl)-1,2,4-oxadiazolidine-3,5-dione was synthesized using the procedure outlined for example 1 using 3,4-dichlorobenzyl bromide and the resulting ether was further alkylated using benzyl bromide.

Example 20

Synthesis of 2-{[5-(2-naphthylmethoxy)-1-(2-propynyl)-1H-indol-3-yl]methyl}-1,2,4-oxadiazolidine-3,5-dione 2-{[5-(2-naphthylmethoxy)-1-(2-propynyl)-1H-indol-3-yl]methyl}-1,2,4-oxadiazolidine-3,5-dione was synthesized using the procedure outlined for example 1 using 2-naphthyl bromide and the resulting ether was further alkylated using propargyl bromide.

Example 21

Synthesis of 2-{[1-allyl-5-(2-naphthylmethoxy)-1H-indol-3-yl]methyl}-1,2,4-oxadiazolidine-3,5-dione 2-{[1-allyl-5-(2-naphthylmethoxy)-1H-indol-3-yl]methyl}-1,2,4-oxadiazolidine-3,5-dione was synthesized using the procedure outlined for example 1 using 2-naphthyl bromide and the resulting ether was further alkylated using allyl bromide.

Example 22

Synthesis of 2-{[1-benzyl-5-(2-naphthylmethoxy)-1H-indol-3-yl]methyl}-1,2,4-oxadiazolidine-3,5-dione 2-{[1-benzyl-5-(2-naphthylmethoxy)-1H-indol-3-yl]methyl}-1,2,4-oxadiazolidine-3,5-dione was synthesized using the procedure outlined for example 1 using 2-naphthyl bromide and the resulting ether was further alkylated using benzyl bromide.

Example 23

Synthesis of 2-{[5-[(4-tert-butylbenzyl)oxy]-1-(2-propynyl)-1H-indol-3-yl]methyl}-1,2,4-oxadiazolidine-3,5-dione 2-{[5-[(4-tert-butylbenzyl)oxy]-1-(2-propynyl)-1H-indol-3-yl]methyl}-1,2,4-oxadiazolidine-3,5-dione was synthesized using the procedure outlined for example 1 using 4-t-butylbenzyl bromide and the resulting ether was further alkylated using propargyl bromide.

Example 24

Synthesis of 2-{[5-[(4-bromobenzyl)oxy]-1-(2-propynyl)-1H-indol-3-yl]methyl}-1,2,4-oxadiazolidine-3,5-dione 2-{[5-[(4-bromobenzyl)oxy]-1-(2-propynyl)-1H-indol-3-yl]methyl}-1,2,4-oxadiazolidine-3,5-dione was synthesized using the procedure outlined for example 1 using 4-bromobenzyl bromide and the resulting ether was further alkylated using propargyl bromide.

Example 25

Synthesis of 2-({1-allyl-5-[(4-bromobenzyl)oxy]-1H-indol-3-yl}methyl)-1,2,4-oxadiazolidine-3,5-dione 2-({1-allyl-5-[(4-bromobenzyl)oxy]-1H-indol-3-yl}methyl)-1,2,4-oxadiazolidine-3,5-dione was synthesized using the procedure outlined for example 1 using 4-bromobenzyl bromide and the resulting ether was further alkylated using allyl bromide.

Example 26

Synthesis of 2-{[5-[(3-bromobenzyl)oxy]-1-(2-propynyl)-1H-indol-3-yl]methyl}-1,2,4-oxadiazolidine-3,5-dione 2-{[5-[(3-bromobenzyl)oxy]-1-(2-propynyl)-1H-indol-3-yl]methyl}-1,2,4-oxadiazolidine-3,5-dione was synthesized using the procedure outlined for example 1 using 3-bromobenzyl bromide and the resulting ether was further alkylated using propargyl bromide.

Example 27

Synthesis of 2-({1-allyl-5-[(3-bromobenzyl)oxy]-1H-indol-3-yl}methyl)-1,2,4-oxadiazolidine-3,5-dione 2-({1-allyl-5-[(3-bromobenzyl)oxy]-1H-indol-3-yl}methyl)-1,2,4-oxadiazolidine-3,5-dione was synthesized using the procedure outlined for example 1 using 3-bromobenzyl bromide and the resulting ether was further alkylated using allyl bromide.

Example 28

Synthesis of 2-{[5-[(3-chlorobenzyl)oxy]-1-(2-propynyl)-1H-indol-3-yl]methyl}-1,2,4-oxadiazolidine-3,5-dione 2-{[5-[(3-chlorobenzyl)oxy]-1-(2-propynyl)-1H-indol-3-yl]methyl}-1,2,4-oxadiazolidine-3,5-dione was synthesized using the procedure outlined for example 1 using 3-chlorobenzyl bromide and the resulting ether was further alkylated using propargyl bromide.

Example 29

Synthesis of 2-[(1-allyl-5-{[3-(trifluoromethyl)benzyl]oxy}-1H-indol-3-yl)methyl]-1,2,4-oxadiazolidine-3,5-dione 2-[(1-allyl-5-{[3-(trifluoromethyl)benzyl]oxy}-1H-indol-3-yl)methyl]-1,2,4-oxadiazolidine-3,5-dione was synthesized using the procedure outlined for example 1 using 3-(trifluoromethyl)benzyl bromide and the resulting ether was further alkylated using allyl bromide.

Example 30

Synthesis of 2-{[5-[(4-chlorobenzyl)oxy]-1-(2-propynyl)-1H-indol-3-yl]methyl}-1,2,4-oxadiazolidine-3,5-dione 2-{[5-[(4-chlorobenzyl)oxy]-1-(2-propynyl)-1H-indol-3-yl]methyl}-1,2,4-oxadiazolidine-3,5-dione was synthesized using the procedure outlined for example 1 using 4-chlorobenzyl bromide and the resulting ether was further alkylated using propargyl bromide.

Example 31

Synthesis of 2-({1-allyl-5-[(4-chlorobenzyl)oxy]-1H-indol-3-yl}methyl)-1,2,4-oxadiazolidine-3,5-dione 2-({1-allyl-5-[(4-chlorobenzyl)oxy]-1H-indol-3-yl}methyl)-1,2,4-oxadiazolidine-3,5-dione was synthesized using the procedure outlined for example 1 using 4-chlorobenzyl bromide and the resulting ether was further alkylated using allyl bromide.

Example 32

Synthesis of 2-({1-benzyl-5-[(4-chlorobenzyl)oxy]-1H-indol-3-yl}methyl)-1,2,4-oxadiazolidine-3,5-dione 2-({1-benzyl-5-[(4-chlorobenzyl)oxy]-1H-indol-3-yl}methyl)-1,2,4-oxadiazolidine-3,5-dione was synthesized using the procedure outlined for example 1 using 4-chlorobenzyl bromide and the resulting ether was further alkylated using benzyl bromide.

Example 33

Synthesis of 2-({1-allyl-5-[(2-chlorobenzyl)oxy]-1H-indol-3-yl}methyl)-1,2,4-oxadiazolidine-3,5-dione 2-({1-allyl-5-[(2-chlorobenzyl)oxy]-1H-indol-3-yl}methyl)-1,2,4-oxadiazolidine-3,5-dione was synthesized using the procedure outlined for example 1 using 2-chlorobenzyl bromide and the resulting ether was further alkylated using allyl bromide.

Example 34

Synthesis of 2-({1-allyl-5-[(3,4-dichlorobenzyl)oxy]-1H-indol-3-yl}methyl)-1,2,4-oxadiazolidine-3,5-dione 2-({1-allyl-5-[(3,4-dichlorobenzyl)oxy]-1H-indol-3-yl}methyl)-1,2,4-oxadiazolidine-3,5-dione was synthesized using the procedure outlined for example 1 using 3,4-dichlorobenzyl bromide and the resulting ether was further alkylated using allyl bromide.

Example 35

Synthesis of 2-({5-[(3,4-dichlorobenzyl)oxy]-1-methyl-1H-indol-3-yl}methyl)-1,2,4-oxadiazolidine-3,5-dione 2-({5-[(3,4-dichlorobenzyl)oxy]-1-methyl-1H-indol-3-yl}methyl)-1,2,4-oxadiazolidine-3,5-dione was synthesized using the procedure outlined for example 1 using 3,4-dichlorobenzyl bromide and the resulting ether was further alkylated using methyl bromide.

Example 36

Synthesis of 2-({3'-[(2-chlorobenzyl)oxy]-1,1'-biphenyl-3-yl}methyl)-1,2,4-oxadiazolidine-3,5-dione Step 1. To a solution of 3-bromophenol (86.5 mg, 0.5 mmol) in acetone was added cesium carbonate (651.6 mg, 2 mmol) and 2-chlorobenzyl bromide (0.063 ml, 0.5 mmol). The reaction mixture was shaken at 60° C. overnight. The mixture was filtered and washed. The solvent was evaporated in vacuo.

Step 2. To a solution of crude benzyl ether (0.5 mmol) obtained from step 1 in ethylene glycol dimethyl ether (DME) (2 ml) was added 3-formylphenyl boronic acid (112.5 mg, 0.75 mmol), tetrakis(triphenylphosphine)palladium(0) (28.9 mg, 1.25 mmol), and 2M sodium carbonate solution (1.25 mmol). The reaction mixture was shaken at 80° C. overnight. The mixture was filtered and washed. The solvent was evaporated in vacuo.

Step 3. To a solution of aldehyde (0.25 mmol) obtained from step 2 dissolved in pyridine (0.5 ml) and EtOH (4.5 ml) was added hydroxylamine hydrochloride (17.4 mg, 0.25 mmol). The reaction was heated to 60° C. for 2 hours. The solvent was evaporated in vacuo.

Step 4. To a solution of oxime (0.5 mmol) obtained from step 3 dissolved in MeOH (1 ml) was added borane pyridine complex (2.5 mmol) and 10% HCl (0.5 ml). The reaction was shaken for 3 hours. The solvent was evaporated in vacuo. The residue was partitioned between EtOAc and water. The organic layer was dried with $MgSO_4$ and concentrated in vacuo.

Step 5. To a solution of hydroxylamine (0.5 mmol) obtained from step 4 in anhydrous THF (2 ml) was added N-(chlorocarbonyl) isocyanate (527 mg, 5 mmol). The reaction was shaken at room temperature for 3 hours. To the reaction was added 10% HCl. The solvent was evaporated in vacuo. The crude product was purified by RP-HPLC. $^1$H NMR (DMSO $d_6$, 300 MHz) δ 4.88 (s, 2H), 5.25 (s, 2H), 7.05 (d, J=9.0 Hz, 1H), 7.25–7.53 (m, 8H), 7.64 (s, 3H), 12.46 (s, 1H); MS: (M−H) 441.3

Example 37

Synthesis of 2-[(3'-{[4-(trifluoromethyl)benzyl]oxy}-1,1'-biphenyl-3-yl)methyl]-1,2,4-oxadiazolidine-3,5-dione 2-[(3'-{[4-(trifluoromethyl)benzyl]oxy}-1,1'-biphenyl-3-yl)methyl]-1,2,4-oxadiazolidine-3,5-dione was synthesized using the procedure outlined for example 36 using 4-(trifluoromethyl)benzyl bromide in step 1.

Example 38

2-[(3'-{[3,5-bis(trifluoromethyl)benzyl]oxy}-1,1'-biphenyl-3-yl)methyl]-1,2,4-oxadiazolidine-3,5-dione 2-[(3'-{[3,5-bis(trifluoromethyl)benzyl]oxy}-1,1'-biphenyl-3-yl)methyl]-1,2,4-oxadiazolidine-3,5-dione was synthesized using the procedure outlined for example 36 using 3,5-bis(trifluoromethyl)benzyl bromide in step 1.

Example 39

2-({3'-[(3-chlorobenzyl)oxy]-1,1'-biphenyl-3-yl}methyl)-1,2,4-oxadiazolidine-3,5-dione 2-({3'-[(3-chlorobenzyl)oxy]-1,1'-biphenyl-3-yl}methyl)-1,2,4-oxadiazolidine-3,5-dione was synthesized using the procedure outlined for example 36 using 3-chlorobenzyl bromide in step 1.

Example 40

Synthesis of 2-{[3'-(benzyloxy)-1,1'-biphenyl-3-yl]methyl}-1,2,4-oxadiazolidine-3,5-dione 2-{[3'-(benzyloxy)-1,1'-biphenyl-3-yl]methyl}-1,2,4-oxadiazolidine-3,5-dione was synthesized using the procedure outlined for example 36 using benzyl bromide in step 1.

Example 41

Synthesis of 2-[(3'-{[3-(trifluoromethyl)benzyl]oxy}-1,1'-biphenyl-3-yl)methyl]-1,2,4-oxadiazolidine-3,5-dione 2-[(3'-{[3-(trifluoromethyl)benzyl]oxy}-1,1'-biphenyl-3-yl)methyl]-1,2,4-oxadiazolidine-3,5-dione was synthesized using the procedure outlined for example 36 using 3-(trifluoromethyl)benzyl bromide in step 1.

Example 42

Synthesis of 2-({3'-[(4-chlorobenzyl)oxy]-1,1'-biphenyl-3-yl}methyl)-1,2,4-oxadiazolidine-3,5-dione 2-({3'-[(4-chlorobenzyl)oxy]-1,1'-biphenyl-3-yl}methyl)-1,2,4-oxadiazolidine-3,5-dione was synthesized using the procedure outlined for example 36 using 4-chlorobenzyl bromide in step 1.

Example 43

Synthesis of 2-({3'-[(3,4-dichlorobenzyl)oxy]-1,1'-biphenyl-3-yl}methyl)-1,2,4-oxadiazolidine-3,5-dione 2-({3'-[(3,4-dichlorobenzyl)oxy]-1,1'-biphenyl-3-yl}methyl)-1,2,4-oxadiazolidine-3,5-dione was synthesized using the procedure outlined for example 36 using 3,4-dichlorobenzyl bromide in step 1.

Example 44

Synthesis of 2-{[3'-(2-naphthylmethoxy)-1,1'-biphenyl-3-yl]methyl}-1,2,4-oxadiazolidine-3,5-dione 2-{[3'-(2-naphthylmethoxy)-1,1'-biphenyl-3-yl]methyl}-1,2,4-oxadiazolidine-3,5-dione was synthesized using the procedure outlined for example 36 using 2-naphthylbenzyl bromide in step 1.

Example 45

Synthesis of 2-({3'-[(4-methylbenzyl)oxy]-1,1'-biphenyl-3-yl}methyl)-1,2,4-oxadiazolidine-3,5-dione 2-({3'-[(4-methylbenzyl)oxy]-1,1'-biphenyl-3-yl}methyl)-1,2,4-oxadiazolidine-3,5-dione was synthesized using the procedure outlined for example 36 using 4-methylbenzyl bromide in step 1.

Example 46

Synthesis of 2-({3'-[(3-methylbenzyl)oxy]-1,1'-biphenyl-3-yl}methyl)-1,2,4-oxadiazolidine-3,5-dione 2-({3'-[(3-methylbenzyl)oxy]-1,1'-biphenyl-3-yl}methyl)-1,2,4-oxadiazolidine-3,5-dione was synthesized using the procedure outlined for example 36 using 3-methylbenzyl bromide in step 1.

Example 47

Synthesis of 2-({3'-[(2,6-dichlorobenzyl)oxy]-1,1'-biphenyl-3-yl}methyl)-1,2,4-oxadiazolidine-3,5-dione 2-({3', [(2,6-dichlorobenzyl)oxy]-1,1'-biphenyl-3-yl}methyl)-1,2,4-oxadiazolidine-3,5-dione was synthesized using the procedure outlined for example 36 using 2,6-dichlorobenzyl bromide in step 1.

Example 48

Synthesis of 2-({4'-[(4-tert-butylbenzyl)oxy]-1,1'-biphenyl-3-yl}methyl)-1,2,4-oxadiazolidine-3,5-dione 2-({4'-[(4-tert-butylbenzyl)oxy]-1,1'-biphenyl-3-yl}methyl)-1,2,4-oxadiazolidine-3,5-dione was synthesized was synthesized using the procedure outlined for example 36 using 4-bromophenol and 4-t-butylbenzyl bromide in step 1. $^1$H NMR (DMSO $d_6$, 300 MHz) δ 1.29 (s, 9H), 4.86 (s, 2H), 5.25 (s, 2H), 7.11 (d, J=6.0 Hz, 2H), 7.28 (d, J=6.0 Hz, 1H), 7.37–7.47 (m, 9H), 12.45 (s, 1H); MS: (M−H) 451.3

Example 49

Synthesis of 2-[(4'-{[4-(trifluoromethyl)benzyl]oxy}-1,1'-biphenyl-3-yl)methyl]-1,2,4-oxadiazolidine-3,5-dione 2-[(4'-{[4-(trifluoromethyl)benzyl]oxy}-1,1'-biphenyl-3-yl)methyl]-1,2,4-oxadiazolidine-3,5-dione was synthesized using the procedure outlined for example 36 using 4-bromophenol and 4-(trifluoromethyl)benzyl bromide in step 1.

Example 50

Synthesis of 2-({4'-[(4-bromobenzyl)oxy]-1,1'-biphenyl-3-yl}methyl)-1,2,4-oxadiazolidine-3,5-dione 2-({4'-[(4-bromobenzyl)oxy]-1,1'-biphenyl-3-yl}methyl)-1,2,4-oxadiazolidine-3,5-dione was synthesized using the procedure outlined for example 36 using 4-bromobenzyl bromide in step 1.

Example 51

Synthesis of 2-[(4'-{[3,5-bis(trifluoromethyl)benzyl]oxy}-1,1'-biphenyl-3-yl)methyl]-1,2,4-oxadiazolidine-3,5-dione 2-[(4'-{[3,5-bis(trifluoromethyl)benzyl]oxy}-1,1'-biphenyl-3-yl)methyl]-1,2,4-oxadiazolidine-3,5-dione was synthesized using the procedure outlined for example 36 using 3,5-bis(trifluoromethyl)benzyl bromide in step 1.

Example 52

Synthesis of 2-({4'-[(3-bromobenzyl)oxy]-1,1'-biphenyl-3-yl}methyl)-1,2,4-oxadiazolidine-3,5-dione 2-({4'-[(3-bromobenzyl)oxy]-1,1'-biphenyl-3-yl}methyl)-1,2,4-oxadiazolidine-3,5-dione was synthesized using the procedure outlined for example 36 using 3-bromobenzyl bromide respectively in step 1.

Example 53

Synthesis of 2-({3'-[(4-tert-butylbenzyl)oxy]-1,1'-biphenyl-4-yl}methyl)-1,2,4-oxadiazolidine-3,5-dione 2-({3'-[(4-tert-butylbenzyl)oxy]-1,1'-biphenyl-4-yl}methyl)-1,2,4-oxadiazolidine-3,5-dione was synthesized by following the procedure as outlined for example 36 using 3-bromophenol and 4-t-butylbenzyl bromide in step 1 and 4-formylphenylboronic acid in step 2.

$^1$H NMR (DMSO $d_6$, 300 MHz) δ 1.29 (s, 9H), 4.85 (s, 2H), 5.14 (s, 2H), 6.92–7.71 (m, 12H), 12.51 (s, 1H); MS: (M−H) 451.3

Example 54

Synthesis of 2-({3'-[(4-bromobenzyl)oxy]-1,1'-biphenyl-4-yl}methyl)-1,2,4-oxadiazolidine-3,5-dione 2-({3'-[(4-bromobenzyl)oxy]-1,1'-biphenyl-4-yl}methyl)-1,2,4-oxadiazolidine-3,5-dione was synthesized using the procedure outlined for example 53 using 4-bromobenzyl bromide.

Example 55

Synthesis of 2-({4'-[(3-bromobenzyl)oxy]-1,1'-biphenyl-4-yl}methyl)-1,2,4-oxadiazolidine-3,5-dione 2-({4'-[(3-bromobenzyl)oxy]-1,1'-biphenyl-4-yl}methyl)-1,2,4-oxadiazolidine-3,5-dione was synthesized by following the procedure as outlined for example 36 using 4-bromophenol and 3-bromobenzyl bromide in step 1 and 4-formylphenylboronic acid in step 2. $^1$H NMR (DMSO $d_6$, 300 MHz) δ 4.85 (s, 2H), 5.18 (s, 2H), 7.02 (d, J=9.0 Hz, 2H), 7.43–7.52 (m, 6H), 7.62–7.83 (m, 4H), 12.64 (s, 1H); MS: (M−H) 337.0

Example 56

Synthesis of 2-[4-(phenylethynyl)benzyl]-1,2,4-oxadiazolidine-3,5-dione

Step 1. To a solution of 4-(phenylethynyl)benzaldehyde (0.5 mmol) (commercially available) dissolved in pyridine (0.5 ml) and EtOH (4.5 ml) was added hydroxylamine hydrochloride (17.4 mg, 0.25 mmol). The reaction was heated to 60 C for 2 hours. The solvent was evaporated in vacuo.

Step 2. To a solution of oxime (0.5 mmol) obtained from step 1 dissolved in MeOH (1 ml) was added 8M solution of borane/pyridine complex (0.313 ml, 2.5 mmol) and 10% HCl (0.5 ml). The reaction was shaken for 3 hours. The solvent was evaporated in vacuo. The residue was partitioned between EtOAc and water. The organic layer was dried with $MgSO_4$ and concentrated in vacuo.

Step 3. To a solution of hydroxylamine (0.5 mmol) obtained from step 2 in anhydrous THF (2 ml) was added N-(chlorocarbonyl) isocyanate (0.527 g, 5 mmol). The reaction was shaken at room temperature for 3 hours. To the reaction was added 10% HCl. The solvent was evaporated in vacuo. The crude product was purified by RP-HPLC. MS: (M−H) 291.

Example 57

Synthesis of 2-(4-hex-1-ynylbenzyl)-1,2,4-oxadiazolidine-3,5-dione 2-(4-hex-1-ynylbenzyl)-1,2,4-oxadiazolidine-3,5-dione was synthesized using the procedure outlined for example 56 starting from commercially available 4-hex-1-yn-1ylbenzaldehyde.

Example 58

Synthesis of 2-{[4-(phenylethynyl)thien-2-yl]methyl}-1,2,4-oxadiazolidine-3,5-dione 2-{[4-(phenylethynyl)thien-2-yl]methyl}-1,2,4-oxadiazolidine-3,5-dione was synthesized using the procedure outlined for example 56 starting from commercially available 5-(phenylethynyl)thiophene-2-carboxaldehyde.

Example 59

Synthesis of 2-{[5-(phenylethynyl)thien-2-yl]methyl}-1,2,4-oxadiazolidine-3,5-dione 2-{[5-(phenylethynyl)thien-2-yl]methyl}-1,2,4-oxadiazolidine-3,5-dione was synthesized using the procedure outlined for example 56 starting from commercially available 4-(phenylethynyl)thiophene-2-carboxaldehyde.

Example 60

Synthesis of 2-[3-(phenylethynyl)benzyl]-1,2,4-oxadiazolidine-3,5-dione

2-[3-(phenylethynyl)benzyl]-1,2,4-oxadiazolidine-3,5-dione was synthesized using the procedure outlined for example 56 starting from commercially available 3-(phenylethynyl)-benzaldehyde.

Example 61

Synthesis of 2-(4-{3-[3,5-bis(trifluoromethyl)phenoxy]prop-1-ynyl}benzyl)-1,2,4-oxadiazolidine-3,5-dione Step 1. 4-bromobenzaldehyde (20 mmole) was taken in 1:1 diemthoxyethane and water (50 mL). To it was added 50 mmole of potassium carbonate was added followed by triphenyl phosphine (1.6 mmole), 0.4 mmole of 10% Palladium on Carbon and 0.8 mmole of copper (I) iodide at room temperature. The mixture was stirred at room temperature for 1 hour. To it was added propargyl alcohol (50 mmole) and the reaction mixture was heated overnight. The reaction mixture was cooled to room temperature and filtered through a pad of celite anc concentrated. The residual oil was purified by flash column chromatography using 10% EtOAc in hexane.

Step 2. The alcohol (1 mmole) from step 1 was dissolved in THF and treated with triphenyl phosphine (1 mmole), diethylazodicarboxylate (1 mmole) and 3,5-bistrifluoromethyl phenol and stirred at room temperature overnight. The reaction mixture was concentrated and purified by flash column chromatography (20% EtOAc in hexane).

Step 3. To a solution of the aldehyde from step 2 (0.5 mmol) dissolved in pyridine (0.5 ml) and EtOH (4.5 ml) was added hydroxylamine hydrochloride (17.4 mg, 0.25 mmol). The reaction was heated to 60 C for 2 hours. The solvent was evaporated in vacuo.

Step 4. To a solution of oxime (0.5 mmol) obtained from step 3 dissolved in MeOH (1 ml) was added 8M solution of borane/pyridine complex (0.313 ml, 2.5 mmol) and 10% HCl (0.5 ml). The reaction was shaken for 3 hours. The solvent was evaporated in vacuo. The residue was partitioned between EtOAc and water. The organic layer was dried with $MgSO_4$ and concentrated in vacuo.

Step 5. To a solution of hydroxylamine (0.5 mmol) obtained from step 4 in anhydrous THF (2 ml) was added N-(chlorocarbonyl) isocyanate (0.527 g, 5 mmol). The reaction was shaken at room temperature for 3 hours. To the reaction was added 10% HCl. The solvent was evaporated in vacuo. The crude product was purified by RP-HPLC to give example 6. MS: (M−H) 457.

Example 62

Synthesis of 2-{4-[3-(3,5-dichlorophenoxy)prop-1-ynyl]benzyl}-1,2,4-oxadiazolidine-3,5-dione 2-{4-[3-(3,5-dichlorophenoxy)prop-1-ynyl]benzyl}-1,2,4-oxadiazolidine-3,5-dione was synthesized using the procedure outlined for example 61, but using 3,5-dichlorophenol for the Mitsunobu reaction in step 2.

Example 63

Synthesis of 2-{4-[3-(3-chlorophenoxy)prop-1-ynyl]benzyl}-1,2,4-oxadiazolidine-3,5-dione 2-{4-[3-(3-chlorophenoxy)prop-1-ynyl]benzyl}-1,2,4-oxadiazolidine-3,5-dione was synthesized using the procedure outlined for example 61, but using 3-chlorophenol for the Mitsunobu reaction in step 2.

Example 64

Synthesis of 2-{4-[3-(4-isobutylphenoxy)prop-1-ynyl]benzyl}-1,2,4-oxadiazolidine-3,5-dione 2-{4-[3-(4-isobutylphenoxy)prop-1-ynyl]benzyl}-1,2,4-oxadiazolidine-3,5-dione was synthesized using the procedure outlined for example 61, but using 4-sec-butyl phenol for the Mitsunobu reaction in step 2.

Example 65

Synthesis of 2-{3-[3-(4-tert-butylphenoxy)prop-1-ynyl]benzyl}-1,2,4-oxadiazolidine-3,5-dione 2-{3-[3-(4-tert-butylphenoxy)prop-1-ynyl]benzyl}-1,2,4-oxadiazolidine-3,5-dione was synthesized using the procedure outlined for example 61, but using 3-bromobenzaldehyde in step 1 and using 4-t-butyl phenol for the Mitsunobu reaction in step 2.

Example 66

Synthesis of 2-{3-[3-(4-bromophenoxy)prop-1-ynyl]benzyl}-1,2,4-oxadiazolidine-3,5-dione 2-{3-[3-(4-bromophenoxy)prop-1-ynyl]benzyl}-1,2,4-oxadiazolidine-3,5-dione was synthesized using the procedure outlined for example 61, but using 3-bromobenzaldehyde in step 1 and using 4-bromophenol for the Mitsunobu reaction in step 2.

Example 67

Synthesis of 2-(3-{3-[3,5-bis(trifluoromethyl)phenoxy]prop-1-ynyl}benzyl)-1,2,4-oxadiazolidine-3,5-dione 2-(3-{3-[3,5-bis(trifluoromethyl)phenoxy]prop-1-ynyl}benzyl)-1,2,4-oxadiazolidine-3,5-dione was synthesized using the procedure outlined for example 61, but using 3-bromobenzaldehyde in step 1 and using 3,5-bistrifluoromethyl phenol for the Mitsunobu reaction in step 2.

Example 68

Synthesis of 2-{3-[3-(3,5-dichlorophenoxy)prop-1-ynyl]benzyl}-1,2,4-oxadiazolidine-3,5-dione 2-{3-[3-(3,5-dichlorophenoxy)prop-1-ynyl]benzyl}-1,2,4-oxadiazolidine-3,5-dione was synthesized using the procedure outlined for example 61, but using 3-bromobenzaldehyde in step 1 and using 3,5-dichlorophenol for the Mitsunobu reaction in step 2.

Example 69

Synthesis of 2-{3-[3-(3-chlorophenoxy)prop-1-ynyl]benzyl}-1,2,4-oxadiazolidine-3,5-dione 2-{3-[3-(3-chlorophenoxy)prop-1-ynyl]benzyl}-1,2,4-oxadiazolidine-3,5-dione was synthesized using the procedure outlined for example 61, but using 3-chlorophenol for the Mitsunobu reaction in step 2.

Example 70

Synthesis of 2-{3-[3-(4-isobutylphenoxy)prop-1-ynyl]benzyl}-1,2,4-oxadiazolidine-3,5-dione 2-{3-[3-(4-isobutylphenoxy)prop-1-ynyl]benzyl}-1,2,4-oxadiazolidine-3,5-dione was synthesized using the procedure outlined for example 61, but using 3-bromobenzaldehyde in step 1 and using 4-sec-butyl phenol for the Mitsunobu reaction in step 2.

Example 71

Synthesis of 2-{3,5-bis[(3-chlorobenzyl)oxy]benzyl}-1,2,4-oxadiazolidine-3,5-dione Step 1. To a solution of 3,5-dihydroxybenzaldehyde (69 mg, 0.5 mmol) in acetone was added pottasium carbonate (276 mg, 2 mmol) and 3-chlorobenzyl bromide (0.203 mg, 1.0 mmol). The reaction mixture was shaken at 60° C. overnight. The mixture was filtered and washed. The solvent was evaporated in vacuo.

Step 2. To a solution of aldehyde (0.25 mmol) obtained from step 1 dissolved in pyridine (0.5 ml) and EtOH (4.5 ml) was added hydroxylamine hydrochloride (17.4 mg, 0.25 mmol). The reaction was heated to 60° C. for 2 hours. The solvent was evaporated in vacuo.

Step 3. To a solution of oxime (0.5 mmol) obtained from step 2 dissolved in MeOH (1 ml) was added borane pyridine complex (2.5 mmol) and 10% HCl (0.5 ml). The reaction was shaken for 3 hours. The solvent was evaporated in vacuo. The residue was partitioned between EtOAc and water. The organic layer was dried with $MgSO_4$ and concentrated in vacuo.

Step 4. To a solution of hydroxylamine (0.5 mmol) obtained from step 3 in anhydrous THF (2 ml) was added N-(chlorocarbonyl) isocyanate (527 mg, 5 mmol). The reaction was shaken at room temperature for 3 hours. To the reaction was added 10% HCl. The solvent was evaporated in vacuo. The crude product was purified by RP-HPLC. $^1$H NMR (DMSO $d_6$, 300 MHz) δ 4.81 (s, 2H), 4.98 (s, 2H), 5.16 (s, 2H), 6.97 (d, J=9.0 Hz, 1H), 7.14–7.20 (m, 3H), 7.35–7.45 (m, 6H), 7.57 (s, 1H); MS: (M–H) 471.0

Example 72

Synthesis of 2-(3,5-bis{[4-(trifluoromethyl)benzyl]oxy}benzyl)-1,2,4-oxadiazolidine-3,5-dione 2-(3,5-bis{[4-(trifluoromethyl)benzyl]oxy}benzyl)-1,2,4-oxadiazolidine-3,5-dione was synthesized using the procedure outlined for example 71 using 3,5-dihydroxybenzaldehyde and 4-(trifluoromethyl)benzyl bromide in step 1.

Example 73

Synthesis of 2-{3,5-bis[(3-methylbenzyl)oxy]benzyl}-1,2,4-oxadiazolidine-3,5-dione 2-{3,5-bis[(3-methylbenzyl)oxy]benzyl}-1,2,4-oxadiazolidine-3,5-dione was synthesized using the procedure outlined for example 71 using 3,5-dihydroxybenzaldehyde and 3-methylbenzyl bromide in step 1.

Example 74

Synthesis of 2-{3,5-bis[(3-bromobenzyl)oxy]benzyl}-1,2,4-oxadiazolidine-3,5-dione 2-{3,5-bis[(3-bromobenzyl)oxy]benzyl}-1,2,4-oxadiazolidine-3,5-dione was synthesized using the procedure outlined for example 71 using 3,5-dihydroxybenzaldehyde and 3-bromobenzyl bromide in step 1.

Example 75

Synthesis of 2-{3,5-bis[(2-bromobenzyl)oxy]benzyl}-1,2,4-oxadiazolidine-3,5-dione 2-{3,5-bis[(2-bromobenzyl)oxy]benzyl}-1,2,4-oxadiazolidine-3,5-dione was synthesized using the procedure outlined for example 71 using 3,5-dihydroxybenzaldehyde and 2-bromobenzyl bromide in step 1.

Example 76

Synthesis of 2-(3-methoxy-4,5-bis{[4-(trifluoromethyl)benzyl]oxy}benzyl)-1,2,4-oxadiazolidine-3,5-dione 2-(3-methoxy-4,5-bis{[4-(trifluoromethyl)benzyl]oxy}benzyl)-1,2,4-oxadiazolidine-3,5-dione was synthesized using the procedure outlined for example 71 using 4,5-dihydroxy-3-methoxybenzaldehyde and 4-(trifluoromethyl)benzyl bromide in step 1.

Example 77

Synthesis of 2-{3-methoxy-4,5-bis[(3-methylbenzyl)oxy]benzyl}-1,2,4-oxadiazolidine-3,5-dione 2-{3-methoxy-4,5-bis[(3-methylbenzyl)oxy]benzyl}-1,2,4-oxadiazolidine-3,5-dione was synthesized using the procedure outlined for example 71 using 4,5-dihydroxy-3-methoxybenzaldehyde and 3-methylbenzyl bromide in step 1.

Example 78

Synthesis of 2-{3,4-bis[(3-chlorobenzyl)oxy]-5-methoxybenzyl}-1,2,4-oxadiazolidine-3,5-dione 2-{3,4-bis[(3-chlorobenzyl)oxy]-5-methoxybenzyl}-1,2,4-oxadiazolidine-3,5-dione was synthesized using the procedure outlined for example 71 using 4,5-dihydroxy-3-methoxybenzaldehyde and 3-chlorobenzyl bromide in step 1.

Example 79

Synthesis of 2-{3,4-bis[(3-bromobenzyl)oxy]-5-methoxybenzyl}-1,2,4-oxadiazolidine-3,5-dione 2-{3,4-bis[(3-bromobenzyl)oxy]-5-methoxybenzyl}-1,2,4-oxadiazolidine-3,5-dione was synthesized using the procedure outlined for example 71 using 4,5-dihydroxy-3-methoxybenzaldehyde and 3-bromobenzyl bromide in step 1.

Example 80

Synthesis of 2-{3,4-bis[(2-bromobenzyl)oxy]-5-methoxybenzyl}-1,2,4-oxadiazolidine-3,5-dione 2-{3,4-bis[(2-bromobenzyl)oxy]-5-methoxybenzyl}-1,2,4-oxadiazolidine-3,5-dione was synthesized using the procedure outlined for example 71 using 4,5-dihydroxy-3-methoxybenzaldehyde and 2-bromobenzyl bromide in step 1.

Example 81

Synthesis of 2-(2,3-bis{[4-(trifluoromethyl)benzyl]oxy}benzyl)-1,2,4-oxadiazolidine-3,5-dione 2-(2,3-bis{[4-(trifluoromethyl)benzyl]oxy}benzyl)-1,2,4-oxadiazolidine-3,5-dione was synthesized using the procedure outlined for example 71 using 2,3-dihydroxybenzaldehyde and 4-(trifluoromethyl)benzyl bromide in step 1.

Example 82

Synthesis of 2-{2,3-bis[(3-methylbenzyl)oxy]benzyl}-1,2,4-oxadiazolidine-3,5-dione 2-{2,3-bis[(3-methylbenzyl)oxy]benzyl}-1,2,4-oxadiazolidine-3,5-dione was synthesized using the procedure outlined for example 71 using 2,3-dihydroxybenzaldehyde and 3-methylbenzyl bromide in step 1.

Example 83

Synthesis of 2-{2,3-bis[(3-chlorobenzyl)oxy]benzyl}-1,2,4-oxadiazolidine-3,5-dione 2-{2,3-bis[(3-chlorobenzyl)oxy]benzyl}-1,2,4-oxadiazolidine-3,5-dione was synthesized using the procedure outlined for example 71 using 2,3-dihydroxybenzaldehyde and 3-chlorobenzyl bromide in step 1.

Example 84

Synthesis of 2-{2,3-bis[(3-bromobenzyl)oxy]benzyl}-1,2,4-oxadiazolidine-3,5-dione 2-{2,3-bis[(3-bromobenzyl)oxy]benzyl}-1,2,4-oxadiazolidine-3,5-dione was synthesized using the procedure outlined for example 71 using 2,3-dihydroxybenzaldehyde and 3-bromobenzyl bromide in step 1.

Example 85

Synthesis of 2-{2,3-bis[(2-bromobenzyl)oxy]benzyl}-1,2,4-oxadiazolidine-3,5-dione 2-{2,3-bis[(2-bromobenzyl)oxy]benzyl}-1,2,4-oxadiazolidine-3,5-dione was synthesized using the procedure outlined for example 71 using 2,3-dihydroxybenzaldehyde and 2-bromobenzyl bromide in step 1.

Example 86

Synthesis of 2-(3,4-bis{[4-(trifluoromethyl)benzyl]oxy}benzyl)-1,2,4-oxadiazolidine-3,5-dione 2-(3,4-bis {[4-(trifluoromethyl)benzyl]oxy}benzyl)-1,2,4-oxadiazolidine-3,5-dione was synthesized using the procedure outlined for example 71 using 3,4-dihydroxybenzaldehyde and 4-(trifluoromethyl)benzyl bromide in step 1.

Example 87

Synthesis of 2-{3,4-bis[(3-methylbenzyl)oxy]benzyl}-1,2,4-oxadiazolidine-3,5-dione 2-{3,4-bis[(3-methylbenzyl)oxy]benzyl}-1,2,4-oxadiazolidine-3,5-dione was synthesized using the procedure outlined for example 71 using 3,4-dihydroxybenzaldehyde and 3-methylbenzyl bromide in step 1.

Example 88

Synthesis of 2-{3,4-bis[(3-chlorobenzyl)oxy]benzyl}-1,2,4-oxadiazolidine-3,5-dione 2-{3,4-bis[(3-chlorobenzyl)oxy]benzyl}-1,2,4-oxadiazolidine-3,5-dione was synthesized using the procedure outlined for example 71 using 3,4-dihydroxybenzaldehyde and 3-chlorobenzyl bromide in step 1.

Example 89

Synthesis of 2-{3,4-bis[(3-bromobenzyl)oxy]benzyl}-1,2,4-oxadiazolidine-3,5-dione 2-{3,4-bis[(3-bromobenzyl)oxy]benzyl}-1,2,4-oxadiazolidine-3,5-dione was synthesized using the procedure outlined for example 71 using 3,4-dihydroxybenzaldehyde and 3-bromobenzyl bromide in step 1.

Example 90

Synthesis of 2-{3,4-bis[(2-bromobenzyl)oxy]benzyl}-1,2,4-oxadiazolidine-3,5-dione 2-{3,4-bis[(2-bromobenzyl)oxy]benzyl}-1,2,4-oxadiazolidine-3,5-dione was synthesized using the procedure outlined for example 71 using 2-bromobenzyl bromide in step 1.

Example 91

Primary Screen for the PAI-1 Inhibition

Test compounds are dissolved in DMSO at a final concentration of 10 mM, then diluted 100× in physiologic buffer. The inhibitory assay is initiated by the addition of the substituted oxadiazolidinedione (1–100 μM final concentration, maximun DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of the substituted oxadiazolidinedione, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of the test compound and PAI-1. Control treatments include the complete inhibition of tPA by PAI-1 at the molar ratio employed (2:1), and the absence of any effect of the substituted oxadiazolidinedione on tPA alone.

Example 92

Assay for determining $IC_{50}$ of inhibition of PAI-1

This assay is based upon the non-SDS dissociable interaction between tPA and active PAI-1. Assay plates are initially coated with human tPA (10 μg/ml). Substituted oxadiazolidinediones of the present invention are dissolved in DMSO at 10 mM, then diluted with physiologic buffer (pH 7.5) to a final concentration of 1–50 μM. Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the substituted oxadiazolidinedione/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (*Molecular Innovations*, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405nm}$. The quantitation of active PAI-1 bound to tPA at varying concentrations of the substituted oxadiazolidinedione is used to determine the $IC_{50}$. Results are analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table 1.

TABLE 1

| Compound No. | % Inhibition @ 100 μM | $IC_{50}$ (μM) |
|---|---|---|
| 1 | 96 | 13.8 (K) |
| 2 | 100 | |
| 3 | 9 | |
| 4 | 96 | |
| 5 | 100 | |
| 6 | 28 | |
| 7 | 94 | |
| 8 | 94 | |
| 9 | 92 | 26.5 (K) |

TABLE 1-continued

| Compound No. | % Inhibition @ 100 μM | $IC_{50}$ (μM) |
|---|---|---|
| 10 | 92 | 9.36 (K) |
| 11 | 59 | |
| 12 | 100 | |
| 13 | 100 | |
| 14 | 100 | |
| 15 | 91 | |
| 16 | | |
| 17 | 49 | |
| 18 | 100 | |
| 19 | 79 | |
| 20 | 84 | |
| 21 | 98 | |
| 22 | 92 | |
| 23 | 91 | |
| 24 | 68 | |
| 25 | 64 | |
| 26 | 100 | |
| 27 | 100 | |
| 28 | 48 | |
| 29 | 79 | |
| 30 | | |
| 31 | | |
| 32 | | |
| 33 | 91 | |
| 34 | 87 | |
| 35 | | |
| 36 | 100 | |
| 37 | 3 | |
| 38 | 69 | |
| 39 | 99 | |
| 40 | 96 | |
| 41 | 81 | |
| 42 | 100 | |
| 43 | 100 | |
| 44 | 28 | |
| 45 | 94 | |
| 46 | 80 | |
| 47 | 88 | |
| 48 | 23 | |
| 49 | 28 | |
| 50 | 41 | |
| 51 | 65 | |
| 52 | 80 | |
| 53 | 60 | |
| 54 | 10 | |
| 55 | 41 | |
| 56 | 65 | |
| 57 | 56 | |
| 58 | 45 | |
| 59 | 60 | |
| 60 | 38 | |
| 61 | 87 | |
| 62 | 82 | |
| 63 | 85 | |
| 64 | 65 | |
| 65 | 77 | |
| 66 | 85 | |
| 67 | 84 | |
| 68 | 93 | |
| 69 | 85 | |
| 70 | 76 | |
| 71 | 85 | |
| 72 | 87 | |
| 73 | 81 | |
| 74 | 92 | |
| 75 | 91 | |
| 76 | 95 | |
| 77 | 88 | |
| 78 | 91 | |
| 79 | 87 | |
| 80 | 89 | |
| 81 | 92 | |
| 82 | 80 | |
| 83 | 95 | |
| 84 | 95 | |
| 85 | 93 | |

TABLE 1-continued

| Compound No. | % Inhibition @ 100 μM | IC$_{50}$ (μM) |
|---|---|---|
| 86 | 94 | |
| 87 | 92 | |
| 88 | 91 | |
| 89 | 88 | |
| 90 | 94 | |

Example 93

Representative Substituted Indolymethyl Oxadiazolidinediones.

TABLE 2

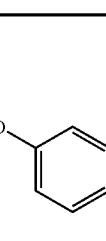

| Compound | R$_4$ | R$_{23}$ | LC$^1$ @ 254 (min) | MS (M − H) |
|---|---|---|---|---|
| 1 | Benzyl | 4-t-Bu | 4.647 | 482.1 |
| 2 | Allyl | 4-t-Bu | 4.510 | 432.1 |
| 3 | Ethyl | 4-t-Bu | 4.478 | 420.1 |
| 4 | Allyl | 4-CF$_3$ | 4.286 | 444.0 |
| 5 | Allyl | 3,5-bis CF3 | 4.488 | 512.0 |
| 6 | Ethyl | 3,5-bis CF$_3$ | 4.463 | 500.0 |
| 7 | Benzyl | 3,5-bis CF$_3$ | 4.614 | 562.0 |
| 8 | Benzyl | 3-Br | 4.412 | 506.0 |
| 9 | Benzyl | 3-Cl | 4.373 | 460.0 |
| 10 | Benzyl | 3-CF$_3$ | 4.402 | 494.1 |
| 11 | Benzyl | 3-Me | 4.327 | 440.0 |
| 12 | propargyl | 4-CF$_3$ | 4.134 | 442.0 |
| 13 | benzyl | 4-CF$_3$ | 4.420 | 494.1 |
| 14 | benzyl | 4-Br | 4.423 | 506.0 |
| 15 | Propargyl | 3,5-bis CF$_3$ | 4.350 | 510.0 |
| 16 | Me | 3,5-bis CF$_3$ | 4.355 | 486.0 |
| 17 | propargyl | 2-Cl | 4.035 | 408.0 |
| 18 | propargyl | 3,4-diCl | 4.250 | 442.0 |
| 19 | benzyl | 3,4-diCl | 4.544 | 494.0 |
| 20 | Propargyl | 2-naphthyl | 4.152 | 424.0 |
| 21 | Allyl | 2-naphthyl | 4.289 | 426.1 |
| 22 | benzyl | 2-naphthyl | 4.443 | 476.1 |
| 23 | propargyl | 4-t-Bu | 4.371 | 430.1 |
| 24 | Propargyl | 4-Br | 4.126 | 452.0 |
| 25 | Allyl | 4-Br | 4.278 | 454.0 |
| 26 | Propargyl | 3-Br | 4.111 | 452.0 |
| 27 | allyl | 3-Br | 4.253 | 454.0 |
| 28 | Propargyl | 3-Cl | 4.068 | 408.0 |
| 29 | allyl | 3-CF$_3$ | 4.255 | 444.1 |
| 30 | Propargyl | 4-Cl | 4.084 | 408.0 |
| 31 | Allyl | 4-Cl | 4.238 | 410.0 |

TABLE 2-continued

| Compound | R$_4$ | R$_{23}$ | LC$^1$ @ 254 (min) | MS (M − H) |
|---|---|---|---|---|
| 32 | benzyl | 4-Cl | 4.401 | 460.1 |
| 33 | Allyl | 2-Cl | 4.034 | 408.0 |
| 34 | Allyl | 3,4-diCl | 4.396 | 444.0 |
| 35 | Me | 3,4-diCl | 4.227 | 418.0 |

$^1$LC Conditions: HP 1100; 40° C.; 5 μL injected; Column: YMC AM, 2.1 × 50, 5□; Gradient A: 0.02% TFA/Water, B: 0.02% TFA/Acetonitrile; Time 0 min: 90% A & 10% B; 5 min: 90% A & 10% B; Post time 1 min; Flow Rate 1.3 ml/min; Detection: 220 and 254 DAD and MSD negative mode.

Example 94

Representative Substituted Biphenylmethyl oxadiazolidinediones

TABLE 3

| Compound No. | R | LC$^1$ @ 254 (min) | MS (M − H) |
|---|---|---|---|
| 36 | 2-Cl | 3.752 | 441.3 |
| 37 | 4-CF3 | 3.592 | 509.4 |
| 38 | 3,5-bis CF3 | 4.052 | 407.3 |
| 39 | 3-Cl | 3.770 | 373.3 |
| 40 | H | 3.560 | 441.4 |
| 41 | 3-CF3 | 3.783 | 407.3 |
| 42 | 4-Cl | 3.773 | 407.3 |
| 43 | 3,4-di Cl | 3.964 | 423.4 |
| 44 | 2-naphthyl | 3.857 | 387.4 |
| 45 | 4-Me | 3.724 | 387.4 |
| 46 | 3-Me | 3.724 | 441.2 |
| 47 | 2,6-di Cl | 3.802 | 441.4 |
| 48 | 4-t-Bu | 4.141 | 451.3 |
| 49 | 4-CF3 | 3.824 | 429.4 |
| 50 | 4-Br | 3.841 | 509.4 |
| 51 | 3,5-bis CF3 | 4.048 | 451.2 |
| 52 | 3-Br | 3.815 | 429.5 |
| 53 | 4-t-Bu | 4.141 | 451.3 |
| 54 | 4-Br | 3.838 | 451.3 |
| 55 | 4-Br | 3.838 | 451.3 |

$^1$LC Conditions: HP 1100; 40° C.; 5 μL injected; Column: Xterra, 4.6 × 30, 2.5 μ; Gradient A: 0.02% TFA/Water, B: 0.02% TFA/Acetonitrile; Time 0 min: 90% A & 10% B; 5 min: 90% A & 10% B; Post time 1 min; Flow Rate 1.5 ml/min; Detection: 220 and 254 DAD and MSD negative mode.

Example 95
Representative Substituted Acetylenic Oxadiazolidinediones.
TABLE 4
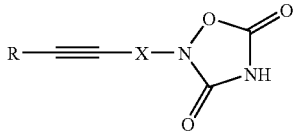
| Compound No. | R | X | LC @ 254 (min) | MS (M + H) |
|---|---|---|---|---|
| 56 | Ph | 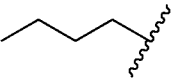 | 3.148 | 291 |
| 57 | 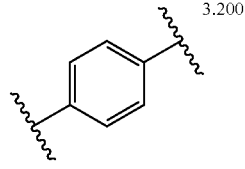 | 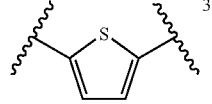 | 3.200 | 271 |
| 58 | Ph | 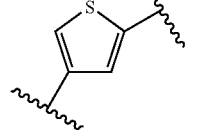 | 3.085 | 297 |
| 59 | Ph | 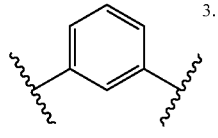 | 3.14 | 297 |
| 60 | Ph | 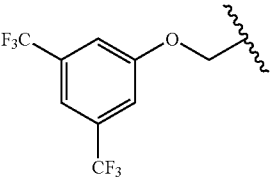 | 3.12 | 291 |
| 61 | 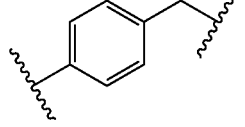 | 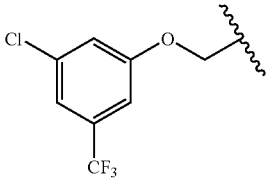 | 4.328 | 457 |
| 62 | 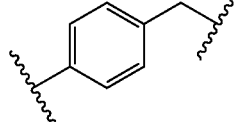 | | 4.318 | 389, 391 |

TABLE 4-continued
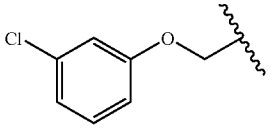
| Compound No. | R | X | LC @ 254 (min) | MS (M + H) |
|---|---|---|---|---|
| 63 | 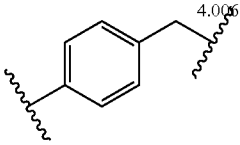 | 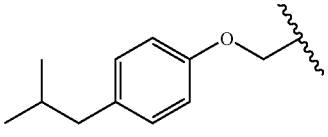 | 4.006 | 355, 357 |
| 64 | 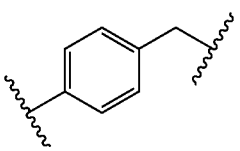 | | 4.420 | 377 |
| 65 | 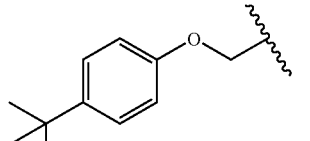 | 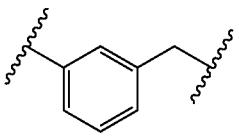 | 4.361 | 377 |
| 66 | 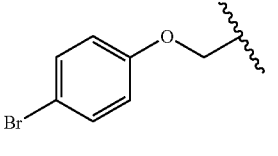 | 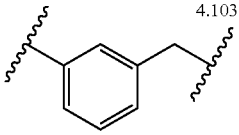 | 4.103 | 399, 401 |
| 67 | 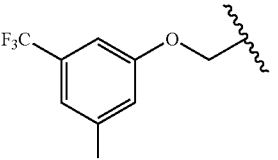 | 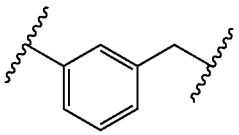 | 4.330 | 457 |
| 68 | 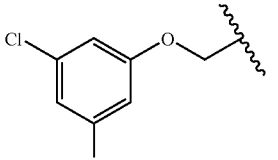 | 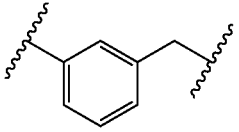 | 4.301 | 389, 391 |

TABLE 4-continued

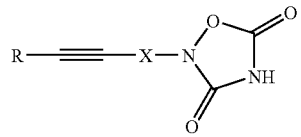

| Compound No. | R | X | LC @ 254 (min) | MS (M + H) |
|---|---|---|---|---|
| 69 | 3-Cl-phenyl-O-CH2- | 1,3-phenylene-CH2- | 4.059 | 355 |
| 70 | 4-isobutyl-phenyl-O-CH2- | 1,3-phenylene-CH2- | 4.414 | 377 |

[1]LC Conditions: HP 1100; 40° C.; 5 µL injected; Column: Xterra, 4.6 × 30, 2.5 µ; Gradient A: 0.02% TFA/Water, B: 0.02% TFA/Acetonitrile; Time 0 min: 90% A & 10% B; 5 min: 90% A & 10% B; Post time 1 min; Flow Rate 1.5 ml/min; Detection: 220 and 254 DAD and MSD negative mode.

Example 96

Representative Substituted Bisbenzyloxybenzyl Oxadiazolidinediones

TABLE 5

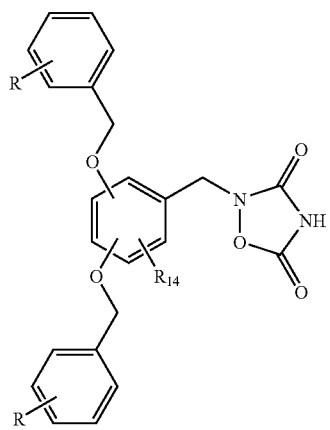

| Compound | BnO- substitution | R14 | R | LC @ 254 (min) | MS (M − H) |
|---|---|---|---|---|---|
| 71 | 3,5 | H | 3-Cl | 3.467 | 471 |
| 72 | 3,5 | H | 4-CF3 | 3.529 | 539 |
| 73 | 3,5 | H | 3-Me | 3.398 | 431 |
| 74 | 3,5 | H | 3-Br | 3.548 | 561 |
| 75 | 3,5 | H | 2-Br | 3.518 | 561 |
| 76 | 4,5 | 3-OMe | 4-CF3 | 3.504 | 569 |
| 77 | 4,5 | 3-OMe | 3-Me | 3.329 | 461 |
| 78 | 4,5 | 3-OMe | 3-Cl | 3.432 | 501 |
| 79 | 4,5 | 3-OMe | 3-Br | 3.506 | 593 |
| 80 | 4,5 | 3-OMe | 2-Br | 3.458 | 593 |
| 81 | 2,3 | H | 4-CF3 | 3.576 | 539 |
| 82 | 2,3 | H | 3-Me | 3.429 | 431 |
| 83 | 2,3 | H | 3-Cl | 3.527 | 471 |
| 84 | 2,3 | H | 3-Br | 3.601 | 561 |

TABLE 5-continued

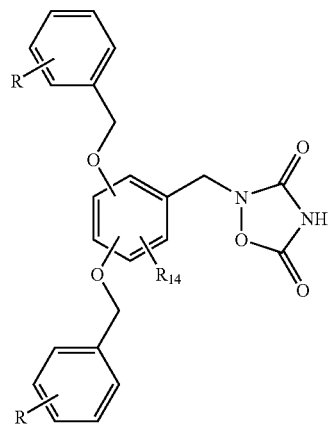

| Compound | BnO- substitution | R14 | R | LC @ 254 (min) | MS (M − H) |
|---|---|---|---|---|---|
| 85 | 2,3 | H | 2-Br | 3.558 | 561 |
| 86 | 3,4 | H | 4-CF3 | 3.501 | 539 |
| 87 | 3,4 | H | 3-Me | 3.323 | 431 |
| 88 | 3,4 | H | 3-Cl | 3.432 | 471 |
| 89 | 3,4 | H | 3-Br | 3.506 | 561 |
| 90 | 3,4 | H | 2-Br | 3.462 | 561 |

[1]LC Conditions: HP 1100; 40° C.; 5 µL injected; Column: Xterra, 4.6 × 30, 2.5 µ; Gradient A: 0.02% TFA/Water, B: 0.02% TFA/Acetonitrile; Time 0 min: 90% A & 10% B; 5 min: 90% A & 10% B; Post time 1 min; Flow Rate 1.5 ml/min; Detection: 220 and 254 DAD and MSD negative mode.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed is:

1. A compound of the formula:

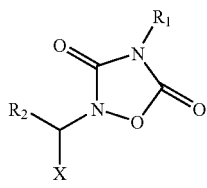

or a pharmaceutically acceptable salt or ester form thereof wherein:

$R_1$ is hydrogen or —$(CH_2)_n$COOH;

n is an integer from 1 to 3;

X is

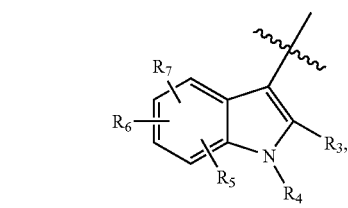
Formula A

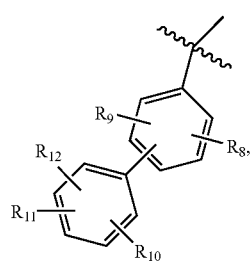
Formula B

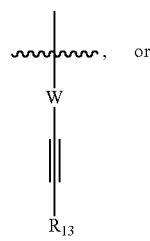
Formula C

, or

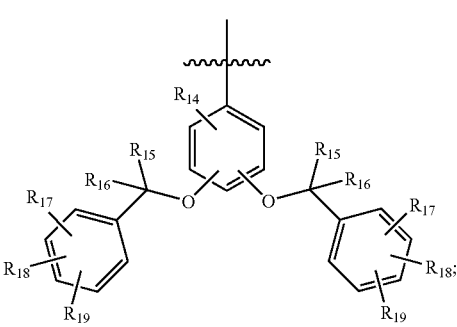
Formula D $R_2$ is hydrogen, $C_1$–$C_8$ alkyl, $C_3$–$C_6$ cycloalkyl, —$CH_2$—$C_3$–$C_6$ cycloalkyl, aryl, benzyl, heteroaryl or —$CH_2$-heteroaryl;

$R_3$ is hydrogen, $C_1$–$C_8$ alkyl, $C_3$–$C_6$ cycloalkyl, —$CH_2$—$C_3$–$C_6$ cycloalkyl, phenyl, benzyl, heteroaryl or —$CH_2$-heteroaryl;

$R_4$ is hydrogen, $C_1$–$C_8$ alkyl, —$(CH_2)_q$—CH=$CH_2$, —$(CH_2)_q$—CH=CH-alkyl, —$(CH_2)_q$C≡CH, —$(CH_2)_q$C≡C-alkyl, aryl, $(CH_2)_q$-aryl, heteroaryl, $(CH_2)_q$-heteroaryl, —CO-aryl, —CO-heteroaryl, —CO-alkyl, —$SO_2$-alkyl, —$SO_2$-aryl, or —$SO_2$-heteroaryl;

$R_5$, $R_6$, $R_7$, $R_8$, $R_9$, $R_{10}$, $R_{11}$, $R_{12}$, $R_{14}$, $R_{17}$, $R_{18}$ and $R_{19}$ are, independently, hydrogen, halogen, $C_1$–$C_6$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$, —$O(CH_2)_q$-aryl, —$O(CH_2)_q$-heteroaryl, aryl, or heteroaryl;

$R_{13}$ is hydrogen, $C_1$–$C_8$ alkyl, $C_2$–$C_8$ alkenyl, $C_2$–$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl;

q is an integer from 0 to 5;

m is an integer from 0 to 5;

$R_{15}$ and $R_{16}$ are, independently, hydrogen, $C_1$–$C_8$ alkyl, $C_3$–$C_6$ cycloalkyl, —$CH_2$—$C_3$–$C_6$ cycloalkyl, aryl, benzyl, heteroaryl or —$CH_2$-heteroaryl;

W is aryl or heteroaryl; and p is an integer from 1 to 5.

2. The compound of claim 1 wherein $R_2$ is hydrogen $C_1$–$C_8$ alkyl, $C_3$–$C_6$ cycloalkyl, —$CH_2$—$_3$–$C_6$cycloalkyl phenyl, benzyl, pyridinyl, or —$CH_2$-pyridinyl;

$R_3$ is hydrogen $C_1$–$C_8$ alkyl, $C_3$–$C_6$ cycloalkyl, —$C_2$—$C_3$–$C_6$cycloalkyl phenyl, benzyl, pyridinyl, or —$CH_2$-pyridinyl;

$R_{15}$ and $R_{16}$ are, independently, hydrogen, $C_1$–$C_8$ alkyl, $C_3$–$C_6$ cycloalkyl, —$CH_2$—$C_3$–$C_6$ cycloalkyl, phenyl, benzyl, pyridinyl, or —$CH_2$-pyridinyl, and wherein the rings of the cycloalkyl, pyridinyl, phenyl and benzyl groups are optionally substituted by 1 to 3 groups selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$.

3. The compound of claim 1, having the formula:

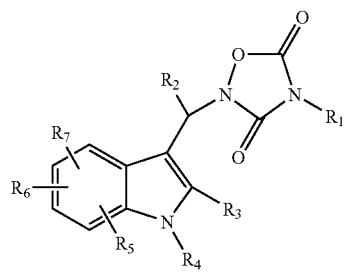

wherein $R^1$, $R^2$, $R^3$, $R^4$, $R^5$, $R^6$ and $R^7$ are as defined in claim 1, or a pharmaceutically acceptable salt or ester form thereof.

4. The compound of claim 3 wherein $R_2$ is hydrogen, $C_3$–$C_6$ cycloalkyl, —$CH_2$—$C_3$–$C_6$ cycloalkyl, aryl, benzyl, heteroaryl or —$CH_2$-heteroaryl.

5. The compound of claim 3 having the formula:

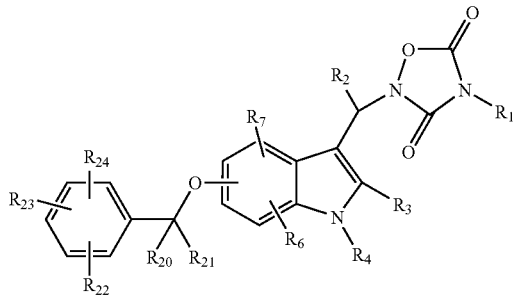

or a pharmaceutically acceptable salt or ester form thereof, wherein:

- $R_{20}$ and $R_{21}$ are, independently, hydrogen, $C_1$–$C_8$ alkyl, —$CH_2$—$C_3$–$C_6$ cycloalkyl, —$CH_2$-pyridinyl, phenyl, or benzyl;
- $R_{22}$, $R_{23}$ and $R_{24}$ are, independently, hydrogen, halogen, $C_1$–$C_6$ alkyl, $C_1$–$C_3$ perfluoroalkyl, —O—$C_1$–$C_3$ perfluoroalkyl, $C_1$–$C_6$ alkoxy, —OH, —$NH_2$, or —$NO_2$, —$O(CH_2)_q$-aryl, —$O(CH_2)_q$-heteroaryl, aryl, or heteroaryl; and
- q is an integer from 0 to 5.

6. The compound of claim 5 wherein $R_{22}$, $R_{23}$ and $R_{24}$ are, independently, hydrogen, halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$, —$O(CH_2)_q$-aryl, —$O(CH_2)_n$-heteroaryl, aryl, or heteroaryl.

7. The compound of claim 5 wherein $R_1$, $R_2$, $R_3$, $R_6$, $R_7$, $R_{20}$, $R_{21}$, $R_{22}$, and $R_{24}$ are hydrogen, $R_4$ is $C_1$–$C_6$ alkyl, —$(CH_2)_q$—CH=$CH_2$, —$(CH_2)_q$—CH=CH-alkyl, —$(CH_2)_q$C≡CH, —$(CH_2)_q$C≡C-alkyl, $(CH_2)_q$-aryl, or —$SO_2$-alkyl; and $R_{23}$ is halogen, $C_1$–$C_6$ alkyl, $C_1$–$C_3$ perfluoroalkyl, $C_1$–$C_6$ alkoxy, or naphthyl.

8. The compound of claim 5 having the formula:

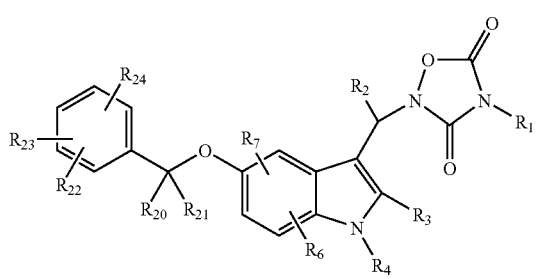

or a pharmaceutically acceptable salt or ester form thereof.

9. The compound of claim 5 having the formula:

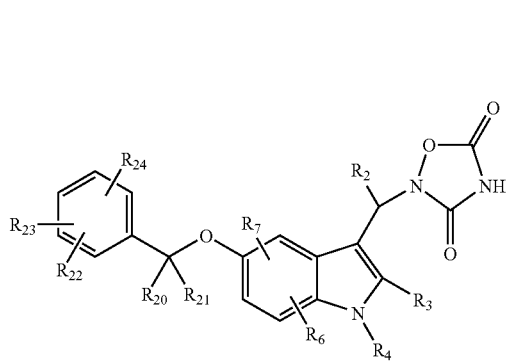

or a pharmaceutically acceptable salt or ester form thereof.

10. The compound of claim 3 that is 2-({1-benzyl-5-[(4-tert-butylbenzyl)oxy]-1H-indol-3-yl}methyl)-1,2,4-oxadiazolidine-3,5-dione, 2-({1-allyl-5-[(4-tert-butylbenzyl)oxy]-1H-indol-3-yl}methyl)-1,2,4-oxadiazolidine-3,5-dione, 2-({5-[(4-tert-butylbenzyl)oxy]-1-ethyl-1H-indol-3-yl}methyl)-1,2,4-oxadiazolidine-3,5-dione, 2-[(1-allyl-5-{[4-(trifluoromethyl)benzyl]oxy}-1H-indol-3-yl)methyl]-1,2,4-oxadiazolidine-3,5-dione, 2-[(1-allyl-5-{[3,5-bis(trifluoromethyl)benzyl]oxy}-1H-indol-3-yl)methyl]-1,2,4-oxadiazolidine-3,5-dione or a pharmaceutically acceptable salt or ester form thereof.

11. The compound of claim 3 that is 2-[(5-{[3,5-bis(trifluoromethyl)benzyl]oxy}-1-ethyl-1H-indol-3-yl)methyl]-1,2,4-oxadiazolidine-3,5-dione, 2-[(1-benzyl-5-{[3,5-bis(trifluoromethyl)benzyl]oxy}-1H-indol-3-yl)methyl]-1,2,4-oxadiazolidine-3,5-dione, 2-({1-benzyl-5-[(3-bromobenzyl)oxy]-1H-indol-3-yl}methyl)-1,2,4-oxadiazolidine-3,5-dione, 2-({1-benzyl-5-[(3-chlorobenzyl)oxy]-1H-indol-3-yl}methyl)-1,2,4-oxadiazolidine-3,5-dione, 2-[(1-benzyl-5-{[3-(trifluoromethyl)benzyl]oxy}-1H-indol-3-yl)methyl]-1,2,4-oxadiazolidine-3,5-dione or a pharmaceutically acceptable salt or ester form thereof.

12. The compound of claim 3 that is 2-({1-benzyl-5-[(3-methylbenzyl)oxy]-1H-indol-3-yl}methyl)-1,2,4-oxadiazolidine-3,5-dione, 2-[(1-(2-propynyl)-5-{[4-(trifluoromethyl)benzyl]oxy}-1H-indol-3-yl)methyl]-1,2,4-oxadiazolidine-3,5-dione, 2-[(1-benzyl-5-{[4-(trifluoromethyl)benzyl]oxy}-1H-indol-3-yl)methyl]-1,2,4-oxadiazolidine-3,5-dione, 2-({1-benzyl-5-[(4-bromobenzyl)oxy]-1H-indol-3-yl}methyl)-1,2,4-oxadiazolidine-3,5-dione, 2-{[5-{[3,5-bis(trifluoromethyl)benzyl]oxy}-1-(2-propynyl)-1H-indol-yl]methyl}-1,2,4-oxadiazolidine-3,5-dione or a pharmaceutically acceptable salt or ester form thereof.

13. The compound of claim 3 that is 2-[(5-{[3,5-bis(trifluoromethyl)benzyl]oxy}-1-methyl-1H-indol-3-yl)methyl]-1,2,4-oxadiazolidine-3,5-dione, 2-{[5-[(2-chlorobenzyl)oxy]-1-(2-propynyl)-1H-indol-3-yl]methyl}-1,2,4-oxadiazolidine-3,5-dione, 2-{[5-[(3,4-dichlorobenzyl)oxy]-1-(2-propynyl)-1H-indol-3-yl]methyl}-1,2,4-oxadiazolidine-3,5-dione, 2-({1-benzyl-5-[(3,4-dichlorobenzyl)oxy]-1H-indol-3yl}methyl)-1,2,4- oxadiazolidine-3,5-dione, 2-{[5-(2-naphthylmethoxy)-1-(2-propynyl)-1H-indol-3-yl]methyl}-1,2,4-oxadiazolidine-3,5-dione or a pharmaceutically acceptable salt or ester form thereof.

14. The compound of claim 3 that is 2-{[1-allyl-5-(2-naphthylmethoxy)-1H-indol-3-yl]methyl}-1,2,4-oxadiazolidine-3,5-dione, 2-{[1-benzyl-5-(2-naphthylmethoxy)-1H-indol-3-yl]methyl}-1,2,4-oxadiazolidine-3,5-dione, 2-{[5-[(4-tert-butylbenzyl)oxy]-1-(2-propynyl)-1H-indol-3-yl]methyl}-1,2,4-oxadiazolidine-3,5-dione, 2-{[5-[(4-bromobenzyl)oxy]-1-(2-propynyl)-1H-indol-3-yl]methyl}-1,2,4-oxadiazolidine-3,5-dione, 2-({1-allyl-5-[(4-bromobenzyl)oxy]-1H-indol-3-yl}methyl)-1,2,4-oxadiazolidine-3,5-dione or a pharmaceutically acceptable salt or ester form thereof.

15. The compound of claim 3 that is 2-{[5-[(3-bromobenzyl)oxy]-1-(2-propynyl)-1H-indol-3-yl]methyl}-1,2,4-oxadiazolidine-3,5-dione, 2-({1-allyl-5-[(3-bromobenzyl)oxy]-1H-indol-3-yl}methyl)-1,2,4-oxadiazolidine-3,5-dione, 2-{[5-[(3-chlorobenzyl)oxy]-1-(2-propynyl)-1H-indol-3-yl]methyl}-1,2,4-oxadiazolidine-3,5-dione, 2-[(1-allyl-5-{[3-(trifluoromethyl)benzyl]oxy}-1H-indol-3-yl)methyl]-1,2,4-oxadiazolidine-3,5-dione, 2- {[5-[(4-chlorobenzyl)oxy]-1-(2-propynyl)-1H-indol-3-yl]methyl}-1,2-oxadiazolidine-3,5-dione or a pharmaceutically acceptable salt or ester form thereof.

16. The compound of claim 3 that is 2-({1-allyl-5-[(4-chlorobenzyl)oxy]-1H-indol-3-yl}methyl)-1,2,4-oxadiazolidine-3,5-dione, 2-({1-benzyl-5-[(4-chlorobenzyl)oxy]-1H-indol-3-yl}methyl)-1,2,4-oxadiazolidine-3,5-dione, 2-({1-allyl-5-[(2-chlorobenzyl)oxy]-1H-indol-3-yl}methyl)-1,2,4-oxadiazolidine-3,5-dione, 2-({1-allyl-5-[(3,4-dichlorobenzyl)oxy]-1H-indol-3-yl}methyl)-1,2,4-oxadiazolidine-3,5-dione, 2-({5-[(3,4-dichlorobenzyl)oxy]-1-methyl-1H-indol-3-yl}methyl)-1,2,4-oxadiazolidine-3,5-dione or a pharmaceutically acceptable salt or ester form thereof.

17. The compound of claim 1 having the formula:

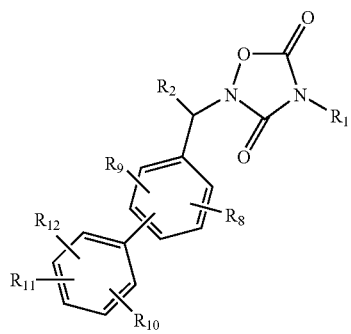

or a pharmaceutically acceptable salt or ester form thereof.

18. The compound of claim 17 having the formula:

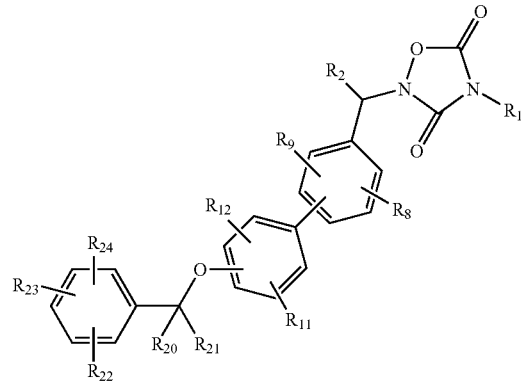

or a pharmaceutically acceptable salt or ester form thereof, wherein:

$R_{20}$ and $R_{21}$ are, independently, hydrogen, $C_1$–$C_8$ alkyl, —$CH_2$—$C_3$–$C_6$ cycloalkyl, —$CH_2$-pyridinyl, phenyl, or benzyl;

$R_{22}$, $R_{23}$ and $R_{24}$ are, independently, hydrogen, halogen, $C_1$–$C_6$ alkyl, $C_1$–$C_3$ perfluoroalkyl, —O—$C_1$–$C_3$ perfluoroalkyl, $C_1$–$C_6$ alkoxy, —OH, —$NH_2$, or —$NO_2$, —O($CH_2$)$_q$-aryl, —O ($CH_2$)$_q$heteroaryl, aryl, or heteroaryl; and q is an integer from 0 to 5.

19. The compound of claim 18 wherein $R_{22}$, $R_{23}$ and $R_{24}$ are, independently, hydrogen, halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$, —O($CH_2$)$_q$-aryl, —O($CH_2$)$_n$-heteroaryl, aryl, or heteroaryl.

20. The compound of claim 18 wherein $R_1$, $R_2$, $R_8$, $R_9$, $R_{11}$, $R_{12}$, $R_{20}$, $R_{21}$, $R_{22}$, and $R_{24}$ are hydrogen, $R_{23}$ is $C_1$–$C_6$ alkyl, $C_1$–$C_3$ perfluoroalkyl, O—$C_1$–$C_3$ perfluoroalkyl, $C_1$–$C_6$ alkoxy, or naphthyl.

21. The compound of claim 18 having the formula:

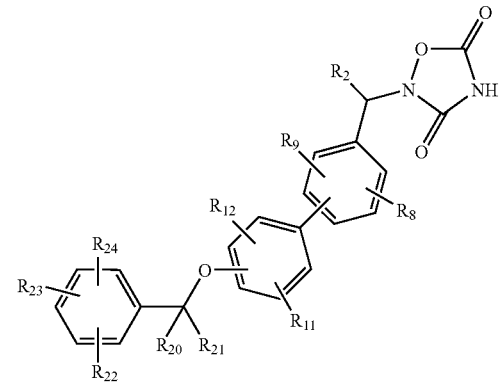

or a pharmaceutically acceptable salt or ester form thereof.

22. The compound of claim 17 that is 2-({3'-[(2-chlorobenzyl)oxy]-1,1'-biphenyl-3-yl}methyl)-1,2,4-oxadiazolidine-3,5-dione, 2-[(3'-{[4-(trifluoromethyl)benzyl]oxy}-1,1'-biphenyl-3-yl)methyl]-1,2,4-oxadiazolidine-3,5-dione, 2-[(3'-{[3,5-bis(trifluoromethyl)benzyl]oxy}-1,1'-biphenyl-3-yl)methyl]-1,2,4-oxadiazolidine-3,5-dione, 2-({3'-[(3- chlorobenzyl)oxy]-1,1'-biphenyl-3-yl}methyl)-1,2,4-oxadiazolidine-3,5-dione, 2-{[3'-(benzyloxy)-1,1'-biphenyl-3-yl]methyl}-1,2,4-oxadiazolidine-3,5-dione or a pharmaceutically acceptable salt or ester form thereof.

23. The compound of claim 17 that is 2-[(3'-{[3-(trifluoromethyl)benzyl]oxy}-1,1'-biphenyl-3-yl)methyl]-1,2,4-oxadiazolidine-3,5-dione, 2-({3'-[(4-chlorobenzyl)oxy]-1,1'-biphenyl-3-yl}methyl)-1,2,4-oxadiazolidine-3,5-dione, 2-({3'-[(3,4-dichlorobenzyl)oxy]-1,1'-biphenyl-3-yl}methyl)-1,2,4-oxadiazolidine-3,5-dione, 2-{[3'-(2-naphthylmethoxy)-1,1'-biphenyl-3-yl]methyl}-1,2,4-oxadiazolidine-3,5-dione, 2-({3'-[(4-methylbenzyl)oxy]-1,1'-biphenyl-3-yl}methyl)-1,2,4-oxadiazolidine-3,5-dione or a pharmaceutically acceptable salt or ester form thereof.

24. The compound of claim 17 that is 2-({3'-[(3-methylbenzyl)oxy]-1,1'-biphenyl-3-yl}methyl)-1,2,4-oxadiazolidine-3,5-dione, 2-({3'-[(2,6-dichlorobenzyl)oxy]-1,1'-biphenyl-3-yl}methyl)-1,2,4-oxadiazolidine-3,5-dione, 2-({4'-[(4-tert-butylbenzyl)oxy]-1,1'-biphenyl-3-yl}methyl)-1,2,4-oxadiazolidine-3,5-dione, 2-[(4'-{[4-(trifluoromethyl)benzyl]oxy}-1,1'-biphenyl-3-yl)methyl]-1,2,4-oxadiazolidine-3,5-dione, 2-({4'-[(4-bromobenzyl)oxy]-1,1'-biphenyl-3-yl}methyl)-1,2,4-oxadiazolidine-3,5-dione or a pharmaceutically acceptable salt or ester form thereof.

25. The compound of claim 17 that is 2-[(4'-{[3,5-dione, bis(trifluoromethyl)benzyl]oxy}-1,1'-biphenyl-3-yl)methyl]-1,2,4-oxadiazolidine-3,5-dione, 2-({4'-[(3-bromobenzyl)oxy]-1,1'-biphenyl-3-yl}methyl)-1,2,4-oxadiazolidine-3,5-dione, ({3'-[(4-tert-butylbenzyl)oxy]-1,1'-biphenyl-4-yl}methyl)-1,2,4-oxadiazolidine-3,5-dione, 2-({3'-[(4-bromobenzyl)oxy]-1,1'-biphenyl-4-yl}methyl)-1,2,4-oxadiazolidine-3,5-dione, 2-({4'-[(3-bromobenzyl)oxy]-1,1'-biphenyl-4-yl}methyl)-1,2,4-oxadiazolidine-3,5-dione or a pharmaceutically acceptable salt or ester form thereof.

26. The compound of claim 1 having the formula:

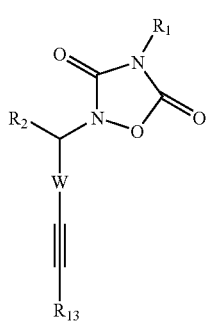

or a pharmaceutically acceptable salt or ester form thereof.

27. The compound of claim 26 having the formula:

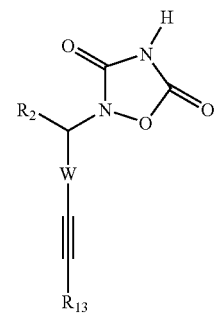

or a pharmaceutically acceptable salt or ester form thereof.

28. The compound of claim 26 wherein $R_1$ and $R_2$ are hydrogen, $R_{13}$ is $C_1$–$C_6$ alkyl, phenyl or —$(CH_2)$—O-aryl where the aryl group is optionally substituted with one or more groups selected from halogen, $C_1$–$C_6$ straight chain alkyl, $C_1$–$C_6$ branched alkyl, $C_1$–$C_3$ perfluoroalkyl, —O—$C_1$–$C_3$ perfluoroalkyl, $C_1$–$C_6$ alkoxy, or naphthyl; and W is aryl or heteroaryl.

29. The compound of claim 26 that is 2-[4-(phenylethynyl)benzyl]-1,2,4-oxadiazolidine-3,5-dione, 2-(4-hex-1-ynylbenzyl)-1,2,4-oxadiazolidine-3,5-dione, 2-{[4-(phenylethynyl)thien-2-yl]methyl}-1,2,4-oxadiazolidine-3,5-dione, 2-{[5-(phenylethynyl)thien-2-yl]methyl}-1,2,4-oxadiazolidine-3,5-dione, 2-[3-(phenylethynyl)benzyl]-1,2,4-oxadiazolidine-3,5-dione or a pharmaceutically acceptable salt or ester form thereof.

30. The compound of claim 26 that is 2-(4-{3-[3,5-bis(trifluoromethyl)phenoxy]prop-1-ynyl}benzyl)-1,2,4-oxadiazolidine-3,5-dione, 2-{4-[3-(3,5-dichlorophenoxy)prop-1-ynyl]benzyl}-1,2,4-oxadiazolidine-3,5-dione, 2-{4-[3-(3-chlorophenoxy)prop-1-ynyl]benzyl}-1,2,4-oxadiazolidine-3,5-dione, 2-{4-[3-(4-isobutylphenoxy)prop-1-ynyl]benzyl}-1,2,4-oxadiazolidine-3,5-dione, 2-{3-[3-(4-tert-butylphenoxy)prop-1-ynyl]benzyl}-1,2,4-oxadiazolidine-3,5-dione or a pharmaceutically acceptable salt or ester form thereof.

31. The compound of claim 26 that is 2-{3-[3-(4-bromophenoxy)prop-1-ynyl]benzyl}-1,2,4-oxadiazolidine-3,5-dione, 2-(3-{3-[3,5-bis(trifluoromethyl)phenoxy]prop-1-ynyl}benzyl)-1,2,4-oxadiazolidine-3,5-dione, 2-{3-[3-(3,5-dichlorophenoxy)prop-1-ynyl]benzyl}-1,2,4-oxadiazolidine-3,5-dione, 2-{3-[3-(3-chlorophenoxy)prop-1-ynyl]benzyl}-1,2,4-oxadiazolidine-3,5-dione, 2-{3-[3-(4-isobutylphenoxy)prop-1-ynyl]benzyl}-1,2,4-oxadiazolidine-3,5-dione or a pharmaceutically acceptable salt or ester form thereof.

32. The compound of claim 1 having the formula:

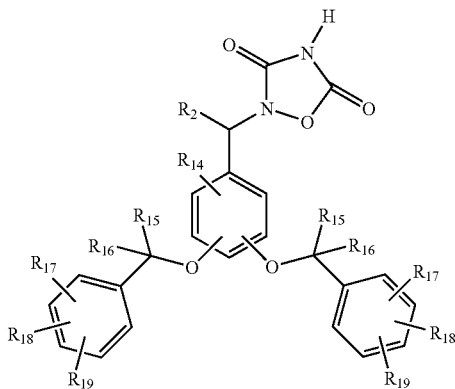

or a pharmaceutically acceptable salt or ester form thereof.

33. The compound of claim 32 wherein $R_1$, $R_2$, $R_{15}$, and $R_{16}$ are independently hydrogen;

$R_{14}$ is hydrogen or $C_1$–$C_3$ alkoxy; and $R_{17}$, $R_{18}$ and $R_{19}$ are independently hydrogen, halogen, $C_1$–$C_6$ alkyl, $C_1$–$C_3$ alkoxy, $C_1$–$C_3$ perfluoroalkyl, or —O—$C_1$–$C_3$ perfluoroalkyl.

34. The compound of claim 32 having the formula:

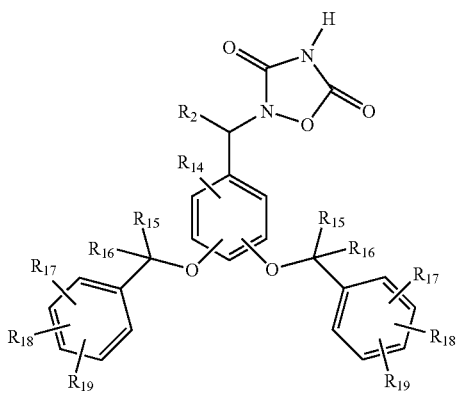

or a pharmaceutically acceptable salt or ester form thereof.

35. The compound of claim 32 that is 2-{3,5-bis[(3-chlorobenzyl)oxy]benzyl}-1,2,4-oxadiazolidine-3,5-dione, 2-(3,5-bis {[4-(trifluoromethyl)benzyl]oxy}benzyl)-1,2,4-oxadiazolidine-3,5-dione, 2-{3,5-bis[(3-methylbenzyl)oxy]benzyl}-1,2,4-oxadiazolidine-3,5-dione, 2-{3,5-bis[(3-bromobenzyl)oxy]benzyl}-1,2,4-oxadiazolidine-3,5-dione, 2-{3,5-bis[(2-bromobenzyl)oxy]benzyl}-1,2,4-oxadiazolidine-3,5-dione or a pharmaceutically acceptable salt or ester form thereof.

36. The compound of claim 32 that is 2-(3-methoxy-4,5-bis{[4-(trifluoromethyl)benzyl]oxy}benzyl)-1,2,4-oxadiazolidine-3,5-dione, 2-{3-methoxy-4,5-bis[(3-methylbenzyl)oxy]benzyl}-1,2,4-oxadiazolidine-3,5-dione, 2-{3,4-bis[(3-chlorobenzyl)oxy]-5-methoxybenzyl}-1,2,4-oxadiazolidine-3,5-dione, 2-{3,4-bis[(3-bromobenzyl)oxy]-5-methoxybenzyl}-1,2,4-oxadiazolidine-3,5-dione, 2-{3,4-bis[(2-bromobenzyl)oxy]-5-methoxybenzyl}-1,2,4-oxadiazolidine-3,5-dione or a pharmaceutically acceptable salt or ester form thereof.

37. The compound of claim 32 that is 2-(2,3-bis{[4-(trifluoromethyl)benzyl]oxy}benzyl)-1,2,4-oxadiazolidine-3,5-dione, 2-{2,3-bis[(3-methylbenzyl)oxy]benzyl}-1,2,4-oxadiazolidine-3,5-dione, 2-{2,3-bis[(3-chlorobenzyl)oxy]benzyl}-1,2,4-oxadiazolidine-3,5-dione, 2-{2,3-bis[(3-bromobenzyl)oxy]benzyl }-1,2,4-oxadiazolidine-3,5-dione, 2-{2,3-bis[(2-bromobenzyl)oxy]benzyl}-1,2,4-oxadiazolidine-3,5-dione or a pharmaceutically acceptable salt or ester form thereof.

38. The compound of claim 32 that is 2-(3,4-bis{[4-(trifluoromethyl)benzyl]oxy}benzyl)-1,2,4-oxadiazolidine-3,5-dione, 2-{3,4-bis[(3-methylbenzyl)oxy]benzyl}-1,2,4-oxadiazolidine-3,5-dione, 2-{3,4-bis[(3-chlorobenzyl)oxy]benzyl}-1,2,4-oxadiazolidine-3,5-dione, 2-{3,4-bis[(3-bromobenzyl)oxy]benzyl}-1,2,4-oxadiazolidine-3,5-dione, 2-{3,4-bis[(2-bromobenzyl)oxy]benzyl}-1,2,4-oxadiazolidine-3,5-dione or a pharmaceutically acceptable salt or ester form thereof.

39. A method of inhibiting PAI-1 activity for the treatment of a PAI-1 disorder selected from the group consisting of thrombosis, atrial fibrillation, myocardial ischemia, stroke, pulmonary fibrosis, thromboembolic complication of surgery, cardiovascular disease caused by noninsulin dependent diabetes mellitus, atherosclerotic plaque formation, chronic obstructive pulmonary disease, renal fibrosis, polycystic ovary syndrome, diabetes, or Alzheimer's disease, comprising administering to a subject in need thereof a therapeutically effective amount of the compound of claim 1.

40. The method of claim 39, wherein the therapeutically effective amount is from 25 mg/kg/day to 200 mg/kg/day.

41. The method of claim 39, wherein the thrombosis is selected from the group consisting of venous thrombosis, arterial thrombosis, cerebral thrombosis, and deep vein thrombosis.

42. A pharmaceutical composition comprising a therapeutically effective amount of a compound of claim 1, or a pharmaceutically acceptable salt or ester form thereof, and a pharmaceutically acceptable excipient or carrier.

* * * * *